United States Patent
Verma et al.

(10) Patent No.: US 6,670,363 B1
(45) Date of Patent: Dec. 30, 2003

(54) AZOLE COMPOUNDS AS THERAPEUTIC AGENTS FOR FUNGAL INFECTIONS

(75) Inventors: Ashwani Kumar Verma, New Delhi (IN); Sudershan K. Arora, Gurgaon (IN); Jasbir Singh Arora, New Delhi (IN); Ashok Rattan, New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/575,578

(22) Filed: May 22, 2000

(30) Foreign Application Priority Data

Mar. 7, 2000 (IN) ..................... 198/DEL/2000

(51) Int. Cl.$^7$ ................ A61K 31/497; A61P 31/10; C07D 279/10; C07D 413/00; C07D 249/08
(52) U.S. Cl. .................. 514/252.12; 514/254.01; 514/254.05; 514/227.8; 514/235.8; 514/252.11; 514/254.07; 544/58.5; 544/121; 544/357; 544/369; 544/370; 544/366; 548/267.8; 548/313.7
(58) Field of Search ............... 514/252.12, 254.01, 514/254.05, 227.8, 235.8, 252.11, 254.07; 544/366, 58.5, 121, 357, 369, 370; 548/267.8, 313.7

(56) References Cited

U.S. PATENT DOCUMENTS

| 4,404,216 A | 9/1983 | Richardson | 424/269 |
| 5,023,258 A | 6/1991 | Gymer et al. | 514/255 |
| 5,371,101 A | 12/1994 | Itoh et al. | 514/383 |
| 5,371,181 A | 12/1994 | Glaser et al. | 528/376 |
| 5,384,094 A | 1/1995 | Schacher | 422/64 |
| 5,466,820 A | 11/1995 | Itoh et al. | 548/263.2 |

OTHER PUBLICATIONS

Powderly, William G., Cryptooccal Meningitis and AIDS, Clinical Infectious Diseases, 1993; 17: 837–42; Eisai Co., Ltd. (JP), ER–30346 Triazole Antifungal, Drugs of the Future, 1996, 21(1): 20–24.

Itoh, K. et al., TAK–187, A New Antifungal Triazole: Synthesis and Antifungal Activity, Abst. F74, American Society for Microbiology; Sep. 1996.

Schell, Wiley, A. et al., In Vitro and In Vivo Efficacy of the Triazole TAK–187 against Cryptococcus neoformans, Antimicrobial Agents and Chemotherapy, Oct. 1998, pp. 2630–2632.

Perfect, John R., et al., In Vitro and In Vivo Efficacies of the Azole SCH56592 against Cryptococcus neoformans, Antimicrobial Agens and Chmotherapy, Aug. 1996, pp. 1910–1913.

*Primary Examiner*—Mukund J. Shah
*Assistant Examiner*—Tamthom N. Truong
(74) *Attorney, Agent, or Firm*—Jayadeep R. Deshmukh; George E. Heibel; William Hare

(57) ABSTRACT

The present invention relates to the derivatives of specially substituted azole compounds which have improved antifungal activity as compared to known compounds such as fluconazole and itraconazole and the processes for the preparation thereof. This invention also relates to pharmaceutical compositions containing the compounds of the present invention and their use in treating and/or preventing fungal infections in mammals, preferably humans.

12 Claims, No Drawings

AZOLE COMPOUNDS AS THERAPEUTIC AGENTS FOR FUNGAL INFECTIONS

FIELD OF THE INVENTION

The present invention relates to the derivatives of specially substituted azole compounds which have improved antifungal activity as compared to known compounds such as fluconazole and itraconazole and the processes for the preparation thereof. This invention also relates to pharmaceutical compositions containing the compounds of the present invention and their use in treating and/or preventing fungal infections in mammals, preferably humans.

BACKGROUND OF THE INVENTION

Life-threatening, systemic fungal infections continue to be a significant problem in health care today. In particular, patients who become "immuno-compromised: as a result of diabetes, cancer, prolonged steroid therapy, organ transplantation antirejection therapy, the acquired immune deficiency syndrome (AIDS) or other physiologically or immunologically compromising syndromes, are especially susceptible to opportunistic fungal infections. Most of these infections are caused by opportunistic pathogens, like species of Candida and Aspergillus and *Cryptococcus neoformans*. During the last 20 years, the incidence of sepsis fungal infection caused by candida species has increased significantly in debilitated and immuno-compromised patients. In addition, the more aggressive and frequently used broad spectrum antibiotic, antineoplastic and immunosuppressive chemotherapies have also augmented fungal infections.

Cryptococcosis is a leading cause of morbidity among AIDS patients. The incidence of life threatening cryptococcal infection among these patients have been estimated to vary from 10 to 30%. During initial therapy, 10 to 20% of these patients die and 30 to 60% patients succumb within a year. Amphoteracin B has changed disseminated cryptococcosis from uniformly fatal infection to curable infection but since Amphoteracin B penetrates the central nervous system poorly, interventricular AID injection may have to be administered for successful management of severe cases of patients with cryptococcal meningitis. Invasive aspergillosis has also become a leading cause of death, mainly among patients suffering from acute leukaemia or after allogenic bone marrow transfusion and after cytotoxic treatment of these conditions. It also occurs in patients with condition such as AIDS and chronic granulomatous disease. At present, only Amphoteracin B and itraconazole are available for treatment of aspergillosis. Inspite of their activity in-vitro, the effect of these drugs in-vivo against *Aspergillus fumigatus* remains low and as a consequence mortality from invasive aspergillosis remains high.

In addition, the emergence of fluconazole-resistant isolates of pathogenic yeasts, particularly in HIV-positive patients, and the general nature of treating fungal infections caused by Aspergillus species, are of growing concerns among infections disease specialists. The precise incidence of infections caused by Aspergillus species is difficult to determine due to lack of accurate, reliable diagnostic methodologies and poor diagnosis. The majority of Aspergillus infections in AIDS patients occur in late stage disease when immune cell functions are minimal. Impaired neutrophil and macrophage function is related to increased infection rates with Aspergillus species. The most common species of Aspergillus causing disease in AIDS patients are *A. fumigatus* (83%), *A. flavus* (9%), *A. niger* (5%) and *A. terreus* (3%).

Within the available drugs to treat fungal infections, the azole class appears to be most promising. This class of compounds inhibits the biosynthesis of ergosterol in fungi, which is the main constituent of fungal cell membrane. Of the various representative antifungals, early azoles used were miconazole, clotrimazole and tioconazole, which were potent against a wide range of fungi pathogenic to human. However, their in-vitro activity was not well exhibited in in-vivo models due to poor oral bioavailability and metabolic vulnerability. Ketoconazole was the first drug that could be used against systemic fungal infection and successfully delivered through oral route. However, it was still quite susceptible to metabolic inactivation and also caused impotence and gynacomastia probably due to its activity against human cytochrome P450 enzymes.

Fluconazole is the current drug of choice for treatment of severe infections caused by Candida species and *C. neoformans*. However, fluconazole has only weak activity against isolates of Aspergillus species [minimum inhibitory concentration (MIC) values of 400 µg/ml], since the drug has low potency ($IC_{50}$=4.8 µM) against lanosterol 14α—demethylase, the target enzyme in the fungus. Itraconazole, another triazole antifungal compound, generally is more active than fluconazole in the treatment of aspergillosis, but its activity in the clinic remains mixed as it showed variable oral availability, low solubility and caused ovarian cancer in animals. This may be due to its high protein binding properties.

Thus, the antifungals available in the market suffer with drawbacks such as, toxicity, narrow spectrum of activity and fungistatic profile rather fungicidal. Some of them also exhibit drug-drug interactions and, as a result, therapy becomes very complex. In view of the high incidence of fungal infections in immunocompromised patients and the recent trends for the steady increase of the populations of such patients, demands for new antifungal agents with broad spectrum of activity and good pharmacokinetic properties has increased. Thus, the continuing demand for safe and effective broad spectrum antifungal agent with favourable pharmacokinetic properties has spurred both the design and development of new systemically active antifungal triazoles. The development of earlier compounds which were referred to as second generation triazoles and which included SCH 39304 (Genaconazole), SCH42427 (Saperaconazole) and BAY R 8783 (Electrazole) had to be discontinued as a result of safety concerns. Another promising second generation triazole, D0870, a derivative of fluconazole, exhibited significant variations in plasma pharmacokinetics besides having weak antiaspergillus activity. Other fluconazole derivatives in different stages of development include voriconazole and ER 30346 (BMS 207147). Voriconazole also shows non-linear pharmacokinetics besides some concern regarding its ocular toxicity, while ER 30346's anti-aspergillus activity, both in vitro and in vivo, is at best, only equal to itraconazole's activity. SCH 56592, is a hydroxylated analogue of itraconazole with potent in-vitro and in-vivo activity, but is undetectable even when the serum drug concentration after several days of treatment are 25 to 100 times above the MIC for the most resistant *C. neoformans*. Thus, the potent activity of SCH 56592 for *C.neoformans* is partially negated by its low concentration at the site of infection to the central nervous system. The above azole candidates are discussed in the following publications: SCH 56592; *Antimicrob. Agents Chemother*, 40, 1910 (1996); 36th Interscience conference Antimicrob Agents Chemother, September, 1996, New Orleans, Abst. F87–F102; TAK-187; 36th Interscience conference *Antimicrob Aqents Chemother*, September, 1996, New Orleans, Abst. F74; EP 567892; ER-30346: *Drugs of the Future*, 21, 20 (1996).

Various compounds having thiol, sulphone, sulphonamides, N-di-substituted sulphonamides, triazoles and tetrazoles of the second asymmetric centre of fluconazole with various side chains have been covered in U.S. Pat. Nos. 5,466,820; 5,371,181 and 5,371,101 assigned to Takeda. But none of them satisfies the above-described medical needs completely, either being weak in spectrum, potency, safety or having undesired pharmacokinetics.

Despite the therapeutic success of fluconazole and itraconazole, there remains a significant need for improved, broad spectrum, better tolerated, less toxic, more potent antifungal compounds with minimal potential for development of resistance among target fungi.

SUMMARY OF THE INVENTION

The present invention relates to new substituted azole compounds which can be utilized to treat and/or prevent the fungal infections in mammals, preferably in humans.

The first aspect of the present invention provides compounds of Formula IA and its pharmaceutically acceptable salts, enantiomers, diastereomers, N-oxides, prodrugs or metabolites,

FORMULA IA

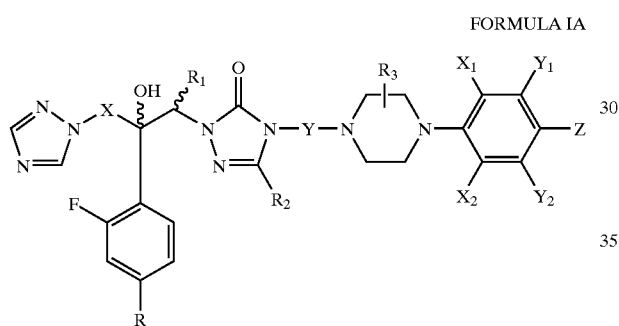

wherein X is selected from the group consisting of $CH_2$, CO, CS, $SO_2$ and —N=N—;

R is selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino (2) $C_1$–$C_4$ alkoxy, (3) halogen (4) formyl, (5) carboxyl (6) $C_1$–$C_4$ acyloxy, (7) phenyl or substituted phenyl, (8) hydroxy, (9) nitro (10) amino (11) furyl, (12) triazolyl, (13) thienyl, (14) piperazinyl (15) morpholinyl (16) thiomorpholinyl (17) imidazolyl (18) oxazolyl and (19) triazolone-yl;

$R_1$ and $R_2$ are each independently (1) hydrogen, (2) $C_1$–$C_4$ alkyl group which is unsubstituted or substituted by 1–3 substituents each independently selected from the group consisting of halogen, hydroxy, $C_1$–$C_4$ alkoxy and amino; (3) nitro, (4) amino (5) cyano, (6) carboxyl or protected carboxyl (7) $SO_2R'$ wherein R' is alkyl or aryl and (8) $C_1$–$C_4$ alkoxy;

Y is a phenyl group which is unsubstituted or substituted by substituents each independently selected from the group consisting of (1) halogen (2) nitro, (3) amino, (4) cyano (5) carboxyl or protected carboxyl (6) hydroxy (7) $C_1$–$C_4$ alkoxy and (8) $SO_2R'$ wherein R' is hydrogen alkyl or aryl;

$R_3$ is selected from the group consisting of hydrogen, $C_1$–$C_4$ alkyd group, halogen, hydroxy, $C_1$–$C_4$ alkoxy, nitro, amino, cyano, carboxyl and $SO_2R'$ wherein R' is hydrogen, alkyl or aryl; and $X_1$, $X_2$, $Y_1$, $Y_2$ and Z are independently selected from the group consisting of hydrogen, halogen, nitro, cyano, amino, sulphonyl, aryl or substituted aryl, $C_1$–$C_4$ alkyl, $C_1$–$C_4$ alkoxy, carboxyl or protected carboxyl.

When $R_1$ is other than hydrogen, Formula IA has two asymmetric centres and there are four possible enantiomers i.e. RR, RS, SR and SS. This invention relates to the mixture of enantiomers as well as individual isomers and the most preferred isomer in this situation is RR.

According to the second aspect of the present invention, there are provided compounds of Formula IB, and its pharmaceutically acceptable salts, enantiomers, diastereomers, N-oxides, prodrugs or metabolites,

FORMULA IB

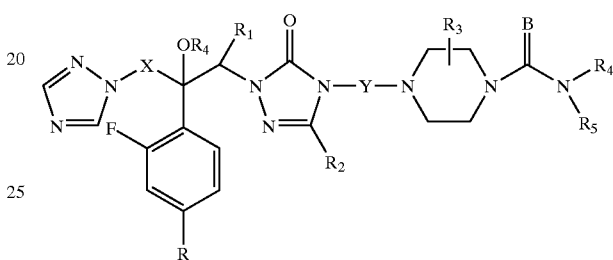

wherein X, R, $R_1$, $R_2$, Y and $R_3$ are the same as defined earlier, $R_4$ is selected from the group consisting of hydrogen, $C_1$–$C_4$ alkyl group which is unsubstituted or substituted, B is selected from oxygen and sulphur atoms; and $R_5$ is selected from the group, (1) hydrogen, (2) $C_1$–$C_4$ alkyl group which is unsubstituted or substituted by 1–3 substituents each independently selected from the group consisting of halogen, hydroxy, $C_1$–$C_4$ alkoxy and amino (3) phenyl which is unsubstituted or substituted with 1–3 substituents each independently selected from the group consisting of (a) $C_1$–$C_4$ alkyl which is unsubstituted or substituted with 1–3 substituted each independently selected from the group consisting of halogen, hydroxy, $C_1$–$C_4$ alkoxy and amino (b) $C_1$–$C_4$ alkoxy, (c) halogen, (d) formyl (e) carboxyl (f) $C_1$–$C_4$ alkoxy (g) $C_1$–$C_4$ alkoxycarboxyl amino (h) phenyl or naphthyl oxycarbonyl amino (i) semicarbazido (j) formamido (k) thioformamide (l) hydroxy (m) nitro (n) amino (o) furyl (p) triazolyl (q) thienyl (r) oxazolyl (s) imidazolyl (t) $CF_3$ and (u) $OCF_3$ (4) naphthyl or naphthyl ($C_1$–$C_4$ alkyl) which may be substituted with 1–6 substituents selected from (a) $C_1$–$C_5$ alkyl which is unsubstituted or substituted with 1–3 substituents each independently selected from the group consisting of halogen, hydroxy, $C_1$–$C_4$ alkoxy and amino (b) halogen, (c) ($C_1$–$C_4$ alkyl) halo (d) $C_1$–$C_4$ alkoxy (e) hydroxy (f) amino (g) carboxyl (h) trifluoromethoxyl (i) trifluoromethyl (j) tetrafluoroethyl (k) tetrafluoroethoxyl (l) tetrafluoropropyl and (m) tetrafluoropropoxyl.

When $R_1$ is other than hydrogen, Formula IA has two asymmetric centres and there are four possible enantiomers i.e. RR, RS, SR and SS. This invention relates to the mixture of enantiomers as well as individual isomers and the most preferred isomer in this situation is RR.

According to the third aspect of the present invention there are provided compounds of Formula II and its pharmaceutically acceptable salts, enantiomers, diastereomers, N-oxides, prodrugs or metabolites,

FORMULA II

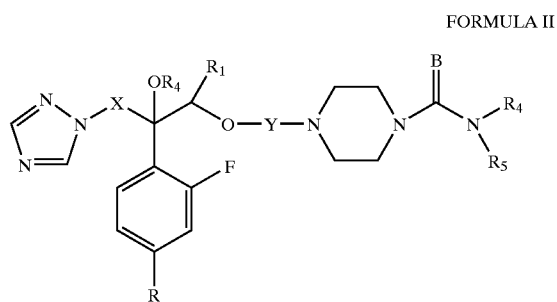

wherein X, R, $R_1$, $R_4$, $R_5$, B and Y have the same meanings as defined earlier.

When $R_1$ is other than hydrogen, Formula II has two asymmetric centres and there are four possible enantiomers i.e. RR, RS, SR and SS. This invention relates to the mixture of enantiomers as well as individual isomers and the most preferred isomer in this situation is RR.

The fourth aspect of the present invention provides compounds of Formula III and its pharmaceutically acceptable salts, enantiomers, diastereomers, N-oxides, prodrugs or metabolites,

FORMULA III

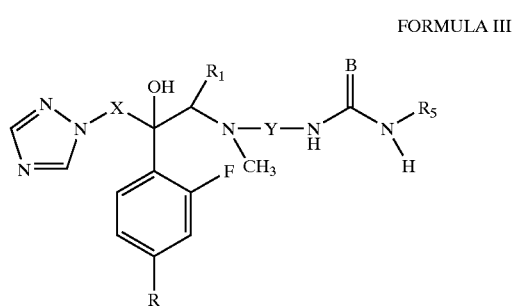

wherein X, R, $R_1$, Y, B and $R_5$ have the same meanings as defined above.

When $R_1$ is other than hydrogen, Formula III has two asymmetric centres and there are four possible enantiomers i.e. RR, RS, SR and SS. This invention relates to the mixture of enantiomers as well as individual isomers and the most preferred in this situation is RR.

Pharmaceutically acceptable, non-toxic, acid addition salts of the compounds of the present invention of Formulae IA, 1B, II and III may be formed with inorganic or organic acids, by methods well known in the art.

It is further object of the invention to provide compositions containing the novel compounds of the present invention in the treatment of fungal infections.

The present invention also includes within its scope prodrugs of the compounds of Formulae IA, IB, II and III. In general, such prodrugs will be functional derivatives of these compounds which readily get converted in vivo into defined compounds. Conventional procedures for the selection and preparation of suitable prodrugs are known.

The invention also includes pharmaceutically acceptable salts, enantiomers, diastereomers, N-oxides, prodrugs, metabolites of the above formulae in combination with pharmaceutically acceptable carriers and optional excipients.

Other advantages of the invention will be set forth in the description which follows, and in part will be apparent from the description, or may be learned by the practice of the invention.

DETAILED DESCRIPTION OF THE INVENTION

In order to achieve the above mentioned aspects and in accordance with the purpose of the invention as embodied and described herein, there are provided processes for the syntheses of compounds of Formulae IA, 1B, II and III, wherein R, $R_1$, $R_2$, $R_3$, $R_4$, $R_5$, X, Y, $X_1$, $Y_1$, $X_2$, $Y_2$, Z and B are the same as defined earlier. The compounds of Formulae IA, 1B, II and III of the present invention may be prepared by following the reaction sequences as depicted below in schemes IA, IB to IX.

SCHEME IA

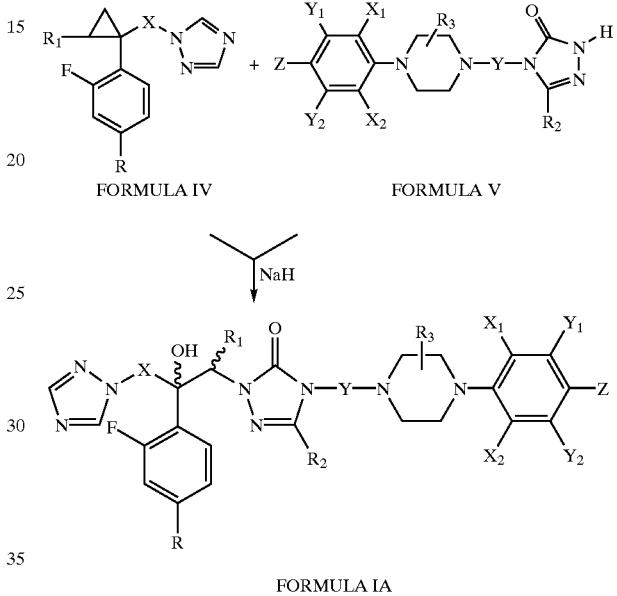

In Scheme IA there is provided a process for preparing a compound of Formula IA, as shown above, wherein X is selected from the group consisting $CH_2$, CO, CS, $SO_2$ and —N=N—, R is selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino (2) $C_1$–$C_4$ alkoxy, (3) halogen (4) formyl (5) carboxyl (6) $C_1$–$C_4$ acyloxy (7) phenyl or substituted phenyl (8) hydroxy (9) nitro (10) amino (11) furyl (12) triazolyl (13) thienyl (14) piperazinyl (15) morpholinyl (16) thiomorpholinyl (17) imidazolyl (18) oxazolyl and (19) triazolone-yl, $R_1$ and $R_2$ are each independently selected from the group consisting of (1) hydrogen, (2) $C_1$–$C_4$ alkyl group which is unsubstituted or substituted by 1–3 substituents each independently selected from the group consisting of halogen, hydroxy, $C_1$–$C_4$ alkoxy and amino (3) nitro (4) amino (5) cyano (6) carboxyl or protected carboxyl (7) $SO_2R'$ wherein R' is hydrogen, alkyl or aryl and (8) $C_1$–$C_4$ alkoxy, Y is a phenyl group which is unsubstituted or substituted by substituents each independently selected from the group consisting of (1) halogen (2) nitro (3) amino (4) cyano (5) carboxyl or protected carboxyl (6) hydroxy (7) $C_1$–$C_4$ alkoxy and (8) $SO_2R'$ wherein R' is hydrogen, alkyl or aryl, $R_3$ is selected from the group consisting of hydrogen. $C_1$–$C_4$ alkyl group, halogen, hydroxy, $C_1$–$C_4$ alkoxy, nitro, amino, cyano, carboxyl and SO$_2$R' wherein R' is hydrogen, alkyl or aryl; and $X_1$, $X_2$, $Y_1$, $Y_2$ and Z are independently selected from the group consisting of hydrogen, halogen, nitro, cyano, amino, sulphonyl, aryl or substituted aryl, $C_1$–$C_4$ alkyl, $C_1$–$C_4$ alkoxy, carboxyl or protected carboxyl.

Also, when $R_1$ is other than hydrogen, Formula I has two asymmetric centres and there are four possible enantiomers i.e. RR, RS, SR and SS, this invention relates to the mixture of enantiomers as well as individual isomers and the most preferred isomer in this situation is RR, which comprises reacting 1-[2-(2,4-disubstituted phenyl)-2,3-epoxy derivative of 1,2,4-triazole of Formula IV, wherein X, R and $R_1$, are the same as defined above, with triazol-3-one derivatives of Formula V, wherein $R_2$, $R_3$, $X_1$, $X_2$, Y, $Y_1$, $Y_2$ and Z have the same meanings, as defined above, in the presence of sodium hydride to afford the desired compound of Formula IA, wherein X, $X_1$, $X_2$, $Y_1$, $Y_2$, Z, R, $R_1$, $R_2$ and $R_3$ have the same meanings as defined above.

SCHEME IB

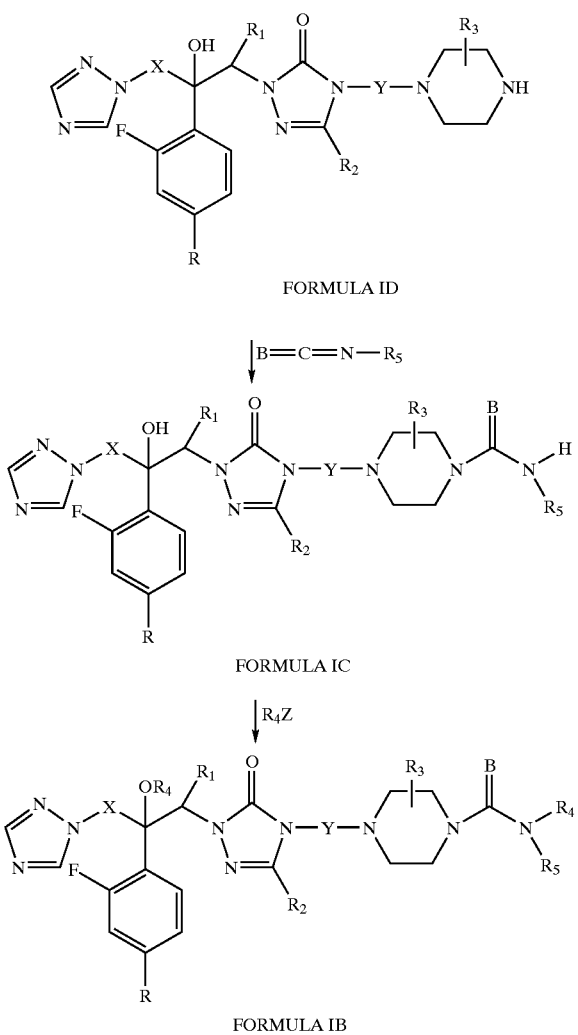

FORMULA ID

FORMULA IC

FORMULA IB

In Scheme IB there is provided a process for preparing a compound of Formula IB, wherein X, R, $R_1$, $R_2$, $R_3$ and Y are the same as defined above, $R_4$ is selected from the group hydrogen, $C_1$–$C_4$ alkyl group which is unsubstituted or substituted, B is selected from oxygen and sulphur atoms, $R_5$ is selected from the group (1) hydrogen, (2) $C_1$–$C_4$ alkyl group which is unsubstituted or substituted by 1–3 substituents each independently selected from the group consisting of halogen, hydroxy, $C_1$–$C_4$ alkoxy and amino, (3) phenyl which is unsubstituted or substituted with 1–3 substituents each independently selected from the group consisting of (a) $C_1$–$C_4$ alkyl which is unsubstituted or substituted with 1–3 substituents each independently selected from the group consisting of halogen, hydroxy, $C_1$–$C_4$ alkoxy and amino (b) $C_1$–$C_4$ alkoxy, (c) halogen, (d) formyl (e) carboxyl (f) $C_1$–$C_4$ acyloxy (g) $C_1$–$C_4$ alkoxycarbonyl amino (h) phenyl or naphthyl-oxy carbonylamino (i) semicarbazido (j) formamido (k) thioformamido (l) hydroxy (m) nitro (n) amino (o) furyl (p) triazolyl (q) thienyl (r) oxazolyl (s) imidazolyl (t) $CF_2$ and (u) $OCF_3$ (4) naphthyl or naphthyl ($C_1$–$C_4$ alkyl) which may be substituted with 1–6 substituents selected from (a) $C_1$–$C_5$ alkyl which is unsubstituted or substituted with 1–3 substituents each independently selected from the group consisting of halogen, hydroxy, $C_1$–$C_4$ alkoxy and amino, (b) halogen (c) ($C_1$–$C_4$ alkyl) halo, (d) $C_1$–$C_4$ alkoxy (e) hydroxy (f) amino (g) carboxyl (h) trifluoromethoxy (i) trifluoromethyl (j) tetrafluoroethyl (k) tetrafluoroethoxyl (l) tetrafluoropropyl and (m) tetrafluoropropoxyl.

Also, when $R_1$ is other than hydrogen, Formula I has two asymmetric centres and there are four possible enantiomers i.e. RR, RS, SR and SS, this invention relates to the mixture of enantiomers as well as individual isomers and the most preferred isomer in this situation is RR, which comprises reacting a compound of Formula ID wherein X, R, $R_1$, $R_2$, $R_3$ and Y have the same meanings as defined earlier, with a compound of Formula $R_5$—N=C=B wherein $R_5$ and B are the same as defined earlier to give a compound of Formula IC, which on reaction with $R_4$Z wherein $R_4$ is the same as defined above and Z is any halogen atom, gives a compound of Formula IB wherein X, R, $R_1$, $R_2$, $R_3$, $R_4$, $R_5$, Y and B have the same meanings as defined earlier.

SCHEME II

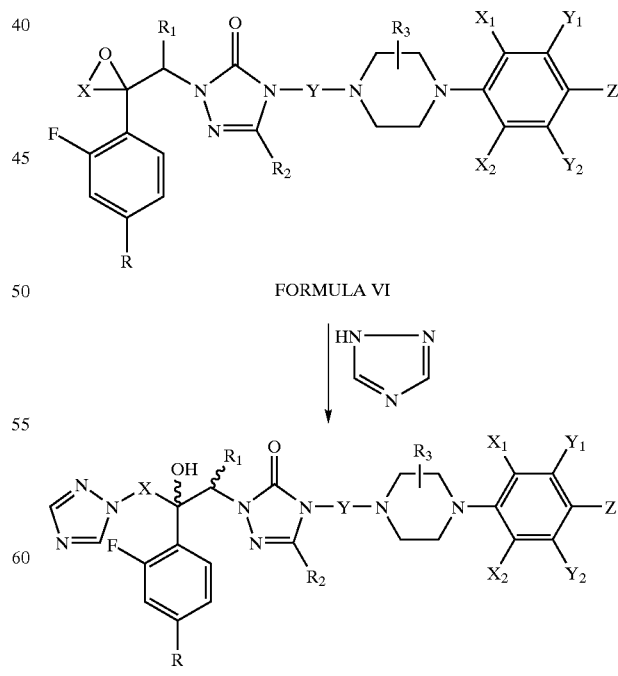

FORMULA VI

FORMULA IA

In Scheme II, there is provided a process for preparing a compound of Formula IA, wherein X, R, $R_1$, $R_2$, $R_3$, Y, $X_1$, $X_2$, $Y_1$, $Y_2$ and Z are the same as defined above, also when $R_1$ is other than hydrogen, Formula I has two asymmertric centres and there are four possible enantiomers i.e. RR, RS, SR and SS, this invention relates to the mixture of enantiomers as well as individual isomers and the most preferred isomer in this situation is RR, which comprises reacting epoxide derivative of Formula VI, wherein X, R, $R_1$, $R_2$, $R_3$, $X_1$, $X_2$, Y, $Y_1$, $Y_2$ and Z are the same as defined above with 1,2,4-triazole to afford a compound of Formula IA.

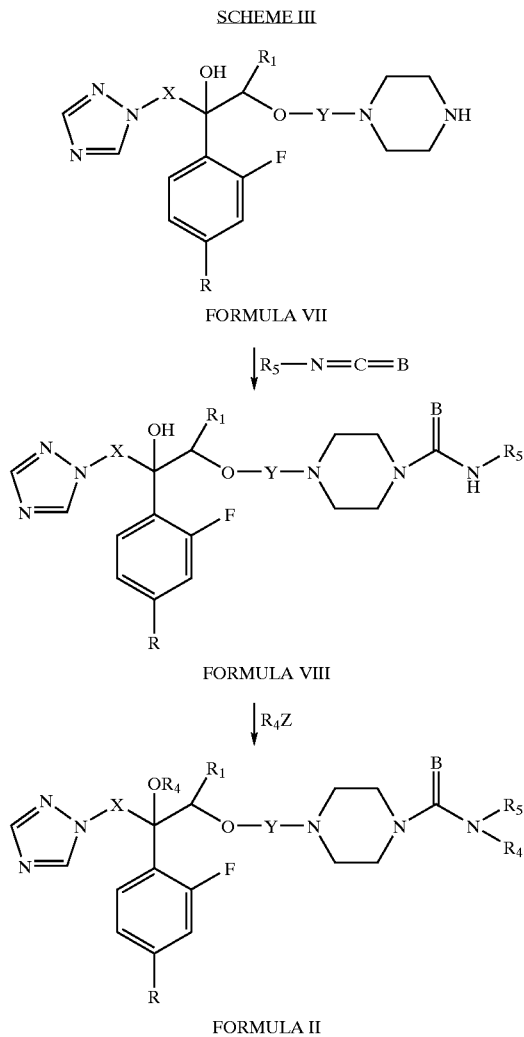

SCHEME III

FORMULA VII $\downarrow R_5—N=C=B$

FORMULA VIII $\downarrow R_4Z$

FORMULA II

There is provided a process for preparing a compound of Formula II, wherein X, R, $R_1$, $R_4$, $R_5$, Y and B have the same meanings as defined earlier, also when $R_1$ is other than hydrogen, Formula II has two asymmetric centres and there are four possible enantiomers i.e. RR, RS, SR and SS, this invention relates to the mixture of enantiomers as well as individual isomers and the most preferred isomer in this situation is RR, which comprises reacting a compound of Formula VII, wherein R, $R_1$, X and Y are same as defined earlier with a compound $R_5$—N=B=B, wherein $R_5$ and B are the same defined earlier to give a compound of Formula VIII, wherein R, $R_1$, $R_5$, X, Y and B have the same meanings as defined earlier. The compound of Formula VIII, on reaction with $R_4Z$, wherein $R_4$ is $C_1$–$C_4$ alkyl and Z is any halogen atom, gives a compound of Formula II, wherein R, $R_1$, $R_4$, $R_5$, X, Y and B are the same as defined earlier.

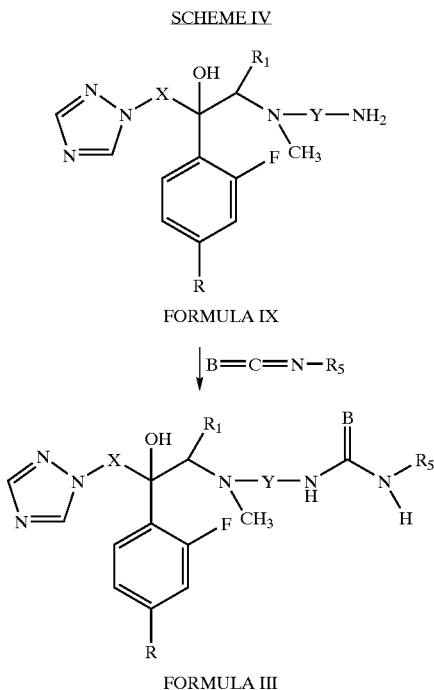

SCHEME IV

FORMULA IX $\downarrow B=C=N—R_5$

FORMULA III

In scheme IV there is provided a process for the preparation of a compound of Formula III, wherein R, $R_1$, $R_5$, X, Y and B are the same as defined above, also when $R_1$ is other than hydrogen, Formula III has two asymmetric centres and there are four possible enantiomers i.e. RR, RS, SR and SS, this invention relates to the mixture of enantiomers as well as individual isomers and the most preferred isomer in this situation is RR, which comprises reacting a compound of Formula IX with a compound of Formula B=C=N—$R_5$ wherein B and $R_5$ are the same as defined earlier, to give the desired compound of Formula III.

SCHEME V

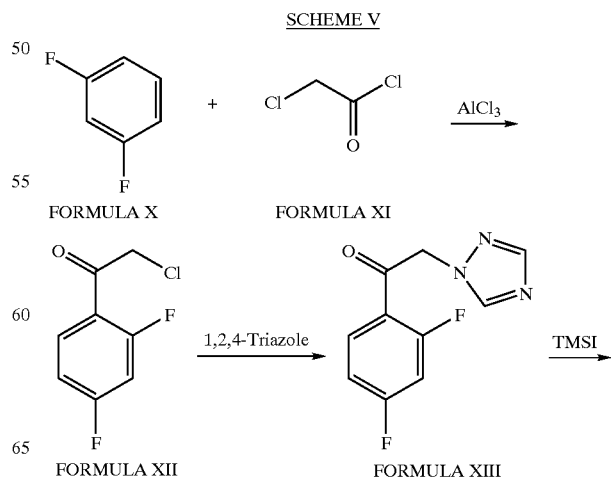

FORMULA X    FORMULA XI

FORMULA XII    1,2,4-Triazole    FORMULA XIII    TMSI

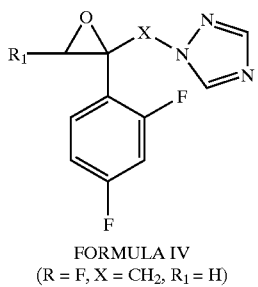

FORMULA IV
(R = F, X = CH₂, R₁ = H)

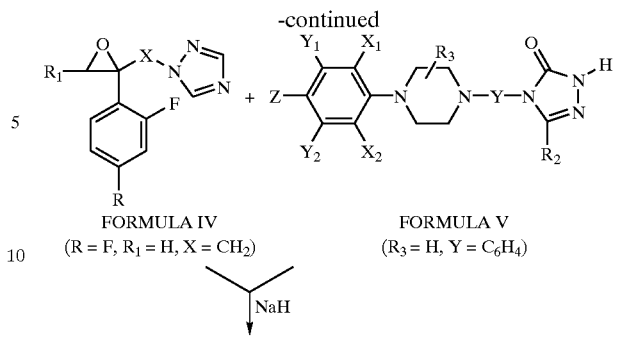

FORMULA IA
(X = CH₂, R = F, R₁ = H, Y = C₆H₄, R₃ = H)

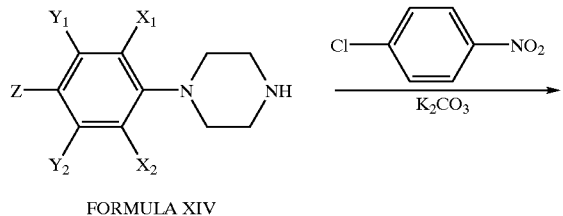

FORMULA XIV

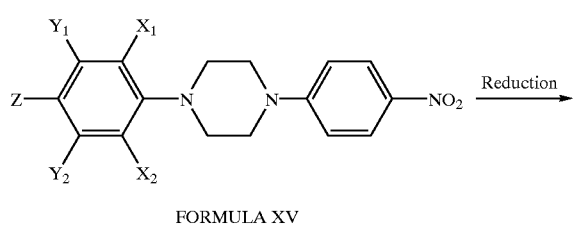

FORMULA XV

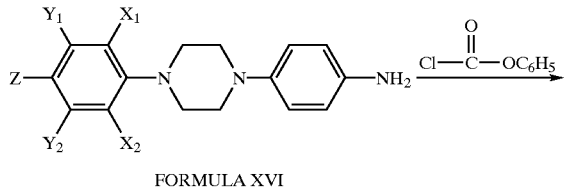

FORMULA XVI

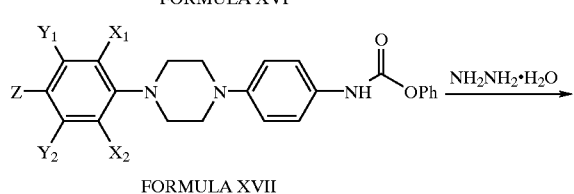

FORMULA XVII

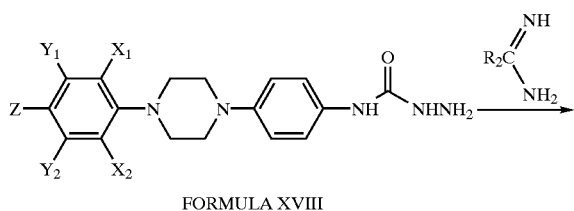

FORMULA XVIII

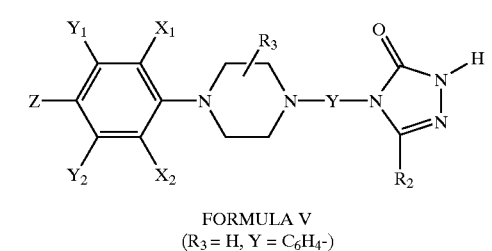

FORMULA V
(R₃ = H, Y = C₆H₄-)

In Scheme V 1,3-difluorobenzene of Formula X, on treatment with chloroacetyl chloride of Formula XI, in the presence of a Lewis acid catalyst such as aluminium trichloride gives α-chloro-2,4-difluoroacetophenone of Formula XII. This compound of Formula XII is further reacted with 1,2,4-triazole to obtain 2-(1H-1,2,4-triazol-1-yl)-2'-4'-difluoroacetophenone of Formula XIII. This compound of Formula XIII is further reacted with trimethyl sulphoxonium iodide (TMSI) to afford 1-[2-(2,4-difluorophenyl)-2,3-epoxypropyl]-1H-1,2,4-triazole of Formula IV (R=F, X=CH₂, R₁=H). The procedure as described in U.S. Pat. No. 4,404,216 is followed to prepare compound of Formula IV.

The triazol-3-one derivatives of Formula V (R₃=H, Y=C₆H₄—), wherein R₂, X₁, X₂, Y₁, Y₂ and Z are the same as defined earlier, are prepared by reacting substituted phenyl piperazine of Formula XIV, wherein X₁, X₂, Y₁, Y₂ and Z are the same as defined earlier, is reacted with 4-chloronitrobenzene to give the corresponding nitroaryl compound of Formula XV, which on catalytic reduction affords the anilino derivative of Formula XVI. The compound of Formula XVI, is acylated with phenyl chloroformate to afford phenyl carbamate derivatives of Formula XVII. Reaction of these carbamate derivative of Formula XVII, with hydrazine hydrate yields semicarbazide derivative of Formula XVIII, which on cyclization with formamidine derivatives gives the triazol-3-one derivatives of Formula V(R₃=H, Y=C₆H₄—). The reaction of compound of Formula V, with the compound of Formula IV (R=F, R₁=H, X=CH2) is carried out in the presence of sodium hydride to afford the desired compound of Formula IA (X=CH₂, R=F, $R_1$=H, Y=$C_6H_4$—, $R_3$=H), wherein $R_2$, $X_1$, $X_2$, $Y_1$, $Y_2$ and Z are the same as defined earlier.

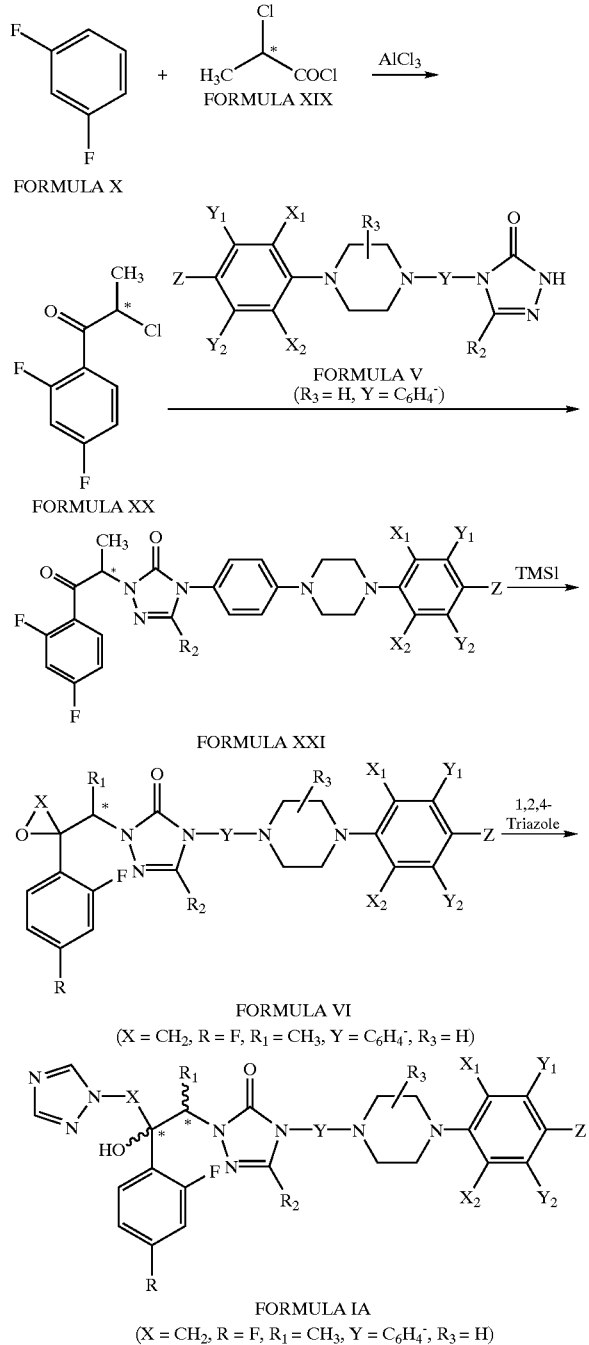

The compounds of Formula IA (X=$CH_2$, R=F, $R_1$=$CH_3$, Y=$C_6H_4$—, $R_3$=H) wherein $R_2$, $X_1$, $Y_1$, $X_2$, $Y_2$ and Z have the same meanings as defined earlier, are synthesized following the reaction sequence embodied in Scheme VI. Thus, 1,3-difluorobenzene of Formula X is reacted with racemic (±)2-chloropropionyl chloride of Formula XIX to give a compound (±)2-chloro-2-methyl-2',4'-difluoroacetophenone of Formula XX. The intermediate of Formula V which in turn is prepared by following the reaction sequence as described in Scheme V wherein $R_2$, $X_1$, $X_2$, $Y_1$, $Y_2$ and Z have the same usual meanings, is condensed with (±)2-chloro-2-methyl-2',4'-difluoroacetophenone of Formula XX in the presence of sodium hydride to afford compound of Formula XXI, wherein $R_2$, $X_1$, $X_2$, $Y_1$, $Y_2$ and Z have the same meanings as defined earlier. The compound of Formula XXI is epoxidized with trimethyl-sulphoxonium iodide (TMSI) in dimethylsulfoxide (DMSO) to give an epoxide derivative of Formula VI (X=$CH_2$, R=F, $R_1$=$CH_3$, Y=$C_6H_4$—, $R_3$=H), which is then condensed with 1,2,4-triazole to give a compound of Formula IA (X=$CH_2$, R=F, $R_1$=$CH_3$, Y=$C_6H_4$—, $R_3$=H), wherein $R_2$, $X_1$, $Y_1$, $X_2$, $Y_2$ and Z are the same as defined earlier.

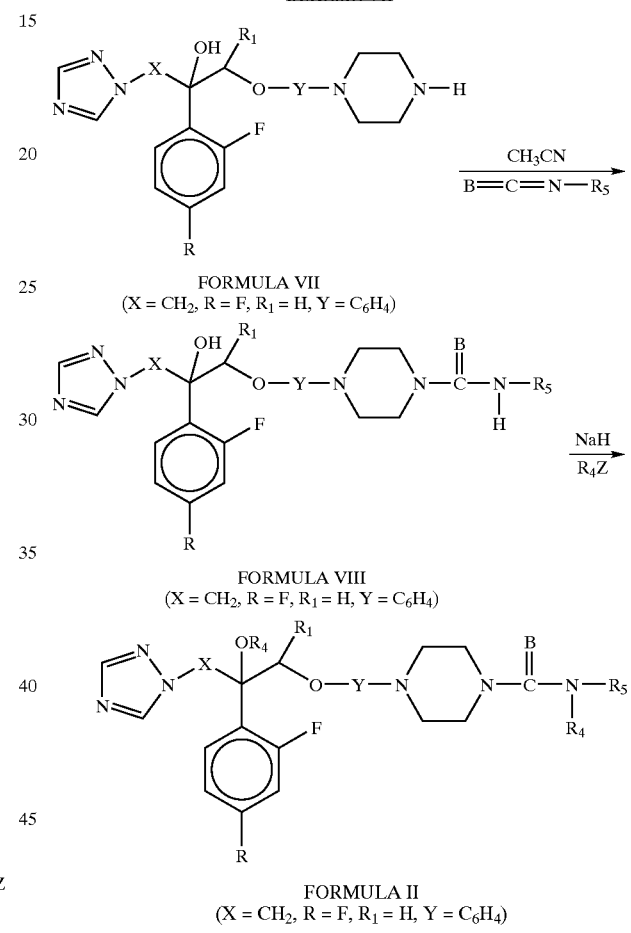

The compounds of Formula II (X=$CH_2$, R=F, $R_1$=H, Y=$C_6H_4$— wherein $R_4$, $R_5$, and B have the same meanings as defined earlier, are synthesized by following the reaction sequence as depicted above in Scheme VII. Thus, 2-(2,4-difluorophenyl)-3-(1H-1,2,4-triazolyl)-1-[4-(piprazinyl) phenoxy]-propan-2-ol of Formula VII (X=$CH_2$, R=F, $R_1$=H, Y=$C_6H_4$—) (prepared by the process as disclosed in U.S. Pat. No. 5,023,258, assigned to Pfizer) on treatment with the compound of Formula B=C=N—$R_5$, wherein B and $R_5$ are the same as defined earlier gives a compound of Formula VII (X=$CH_2$, R=F, $R_1$=H, Y=$C_6H_4$—) wherein $R_5$ and B are the same as defined earlier. This compound of Formula VII (X=$CH_2$, R=F, $R_1$=H, Y=$C_6H_4$—) is further reacted with $R_4Z$ in the presence of sodium hydride gives the required compound of Formula II (X=$CH_2$, R=F, $R_1$=H, Y=$C_6H_4$—, wherein $R_4$, $R_5$ and B are the same as defined earlier.

SCHEME VIII

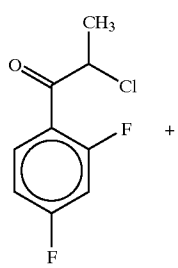

FORMULA XXII

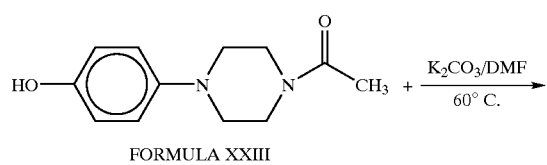

FORMULA XXIII

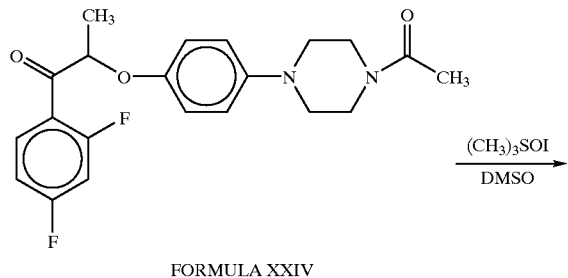

FORMULA XXIV

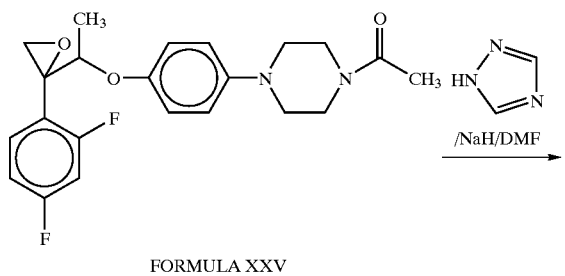

FORMULA XXV

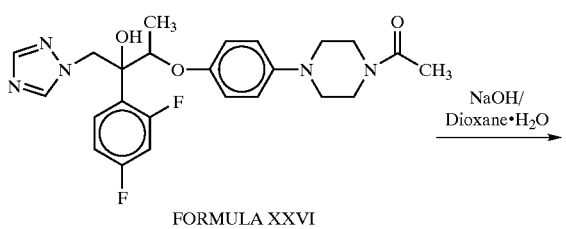

FORMULA XXVI

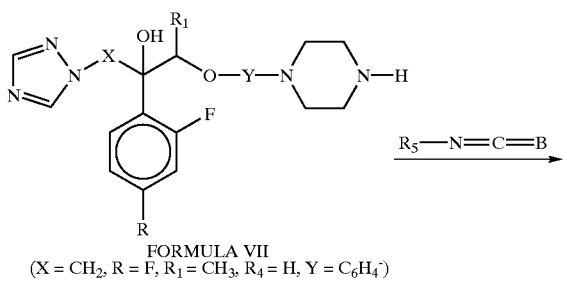

FORMULA VII
(X = CH$_2$, R = F, R$_1$ = CH$_3$, R$_4$ = H, Y = C$_6$H$_4^-$)

-continued

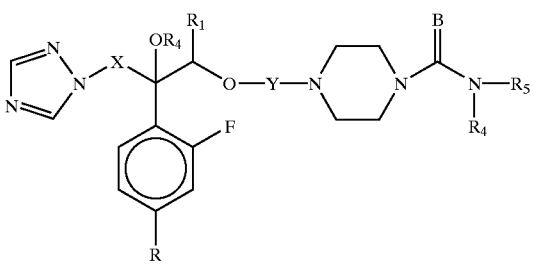

FORMULA II
(X = CH$_2$, R = F, R$_1$ = CH$_3$, R$_4$ = H, Y = C$_6$H$_4^-$)

In Scheme VII, 2-chloro-methyl-2',4'-difluoroacetophenone of Formula XXII, on treatment with 1-acetyl-4-hydroxyphenylpiperazine of Formula XXIII, gives 2-[4-(4-acetylpiperazine)phenoxy]-2-methyl-2',4'-difluoroacetophenone of Formula XXIV in the presence of potassium carbonate in dimethylformamide, which on treatment with trimethyl sulphoxonium iodide (TMSI) in DMSO gives the corresponding epoxide of Formula XXV. This compound of Formula XXV is reacted with 1,2,4-triazole to yield a compound of Formula XXVI, which in turn on hydrolysis with sodium hydroxide in dioxane gives a compound of Formula VII (X=CH$_2$, R=F, R$_1$=CH$_3$, Y=C$_6$H$_4$—). The compound of Formula VII on reaction with R$_5$—N=B=B gives a compound of Formula II (X=CH$_2$, R=F, R$_1$=CH$_3$, R$_4$=H) wherein R$_5$ and B have the same meanings as defined earlier.

SCHEME IX

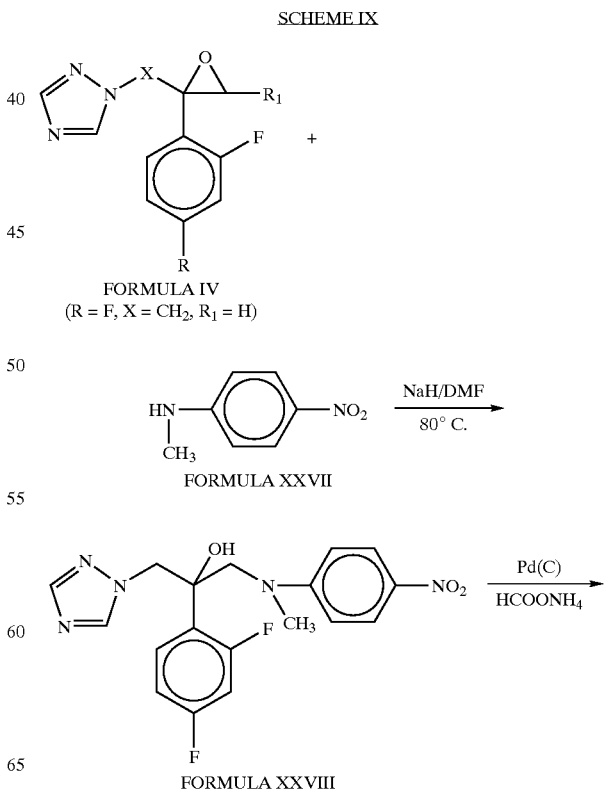

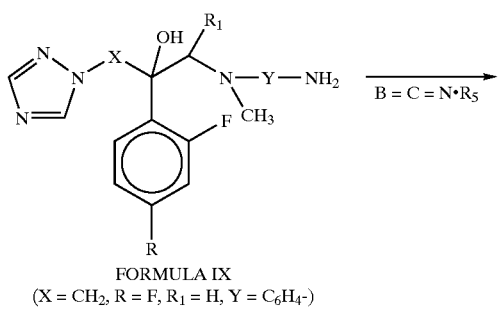

FORMULA IX
(X = CH$_2$, R = F, R$_1$ = H, Y = C$_6$H$_4$-)

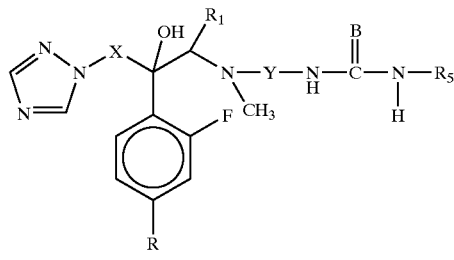

FORMULA III
(X = CH$_2$, R = F, R$_1$ = H, Y = C$_6$H$_4$-)

In Scheme IX 1-[2-(2,4-difluorophenyl)-2,3-epoxypropyl]-1H-1,2,4-triazole of Formula IV (R=F, X=CH$_2$, R$_1$=H) on treatment with N-methyl-4-nitroaniline of Formula XXVII gives 3-[N-Methyl-N-(4-nitrophenyl)]-2-(2,4-difluorophenyl)-1-(1H-1,2,4-triazolyl)-propan-3-amino-2-ol of Formula XXVIII which on reduction with palladium on charcoal gives 3-[N-Methyl-N-(4-aminophenyl)]-2-(2,4-difluorophenyl)-1-(1H-1,2,4-triazolyl)-propane-3-amino-2-ol of Formula IX, (X=CH$_2$, R=F, R$_1$=H, Y=C$_6$H$_4$—) which on reaction with B=C=N—R$_5$ gives a compound of Formula III (X=CH$_2$, R=F, R$_1$=H, Y=C$_6$H$_4$—) wherein B and R$_5$ are the same as defined earlier.

In the above schemes where specific acids, bases, solvents, catalysts, oxidising agents, reducing agents etc. are mentioned, it is to be understood that the other acids, bases, solvents, catalysts, oxidising agents, reducing agents etc. may be used. Similarly, the reaction temperature and duration of the reaction may be adjusted according to the need.

An illustrative list of particular compounds according to the invention and capable of being produced by Schemes IA, IB to IX include:

| Compound No. | Chemical Name |
|---|---|
| 1. | 2-{[1R2R/1S2S]-2-(2,4-Difluorophenyl)-2-hydroxy-1-methyl-3-(1H-1,2,4-triazol-1-yl)propyl}-4-{4-[4-(4-chlorophenyl)-1-piperazinyl]phenyl}-3-(2H,4H)-1,2,4-triazolone |
| 2. | 2-{[1R2S/1S2R]-2-(2,4-Difluorophenyl)-2-hydroxy-1-methyl-3-(1H-1,2,4-triazol-1-yl)propyl}-4-{4-[4-(4-chlorophenyl)-1-piperazinyl]phenyl}-3-(2H,4H)-1,2,4-triazolone |
| 3. | 2-{[1R2R/1S2S]-2-(2,4-Difluorophenyl)-2-hydroxy-1-methyl-3-(1H-1,2,4-triazol-1-yl)propyl}-4-{4-[4-(2,4-dinitrophenyl)-1-piperazinyl]phenyl}-3-(2H,4H)-1,2,4-triazolone |
| 4. | 2-{[1R2S/1S2R]-2-(2,4-Difluorophenyl)-2-hydroxy-1-methyl-3-(1H-1,2,4-triazol-1-yl)propyl}-4-{4-[4-(2,4-dinitrophenyl)-1-piperazinyl]phenyl}-3-(2H,4H)-1,2,4-triazolone |
| 5. | 2-{[1R2R/1S2S]-2-(2,4-Difluorophenyl)-2-hydroxy-1-methyl-3-(1H-1,2,4-triazol-1-yl)propyl}-4-[4-1-phenylpiperazinyl)phenyl]-3-(2H,4H)-1,2,4-triazolone |
| 6. | 2-{[1R2S/1S2R]-2-(2,4-Difluorophenyl)-2-hydroxy-1-methyl-3-(1H-1,2,4-triazol-1-yl)propyl}-4-[4-(1-phenylpiperazinyl)phenyl]-3-(2H,4H)-1,2,4-triazolone |
| 7. | 2-{[1R2R/1S2S]-2-(2,4-Difluorophenyl)-2-hydroxy-1-methyl-3-(1H-1,2,4-triazol-1-yl)propyl}-4-{4-[4-(3,4-dichlorophenyl)-1-piperzinyl]phenyl}-3-(2H,4H)-1,2,4-triazolone |
| 8. | 2-{[1R2S/1S2R]-2-(2,4-Difluorophenyl)-2-hydroxy-1-methyl-3-(1H-1,2,4-triazol-1-yl)propyl}-4-{4-[4-(3,4-dichlorophenyl)-1-piperazinyl]phenyl}-3-(2H,4H)-1,2,4-triazolone |
| 9. | 2-{[1R2R/1S2S]-2-(2,4-Difluorophenyl)-2-hydroxy-1-methyl-3-(1H-1,2,4-triazol-1-yl)propyl}-4-{4-[4-(3-trifluoromethylphenyl)-1-piperazinyl]phenyl}-3-(2H,4H)-1,2,4-triazolone |
| 10. | 2-{[1R2S/1S2R]-2-(2,4-Difluorophenyl)-2-hydroxy-1-methyl-3-(1H-1,2,4-triazol-1-yl)propyl}-4-{4-[4-(3-trifluoromethylphenyl)-1-piperazinyl]phenyl}-3-(2H,4H)-1,2,4-triazolone |
| 11. | 2-{[1R2R/1S2S]-2-(2,4-Difluorophenyl)-2-hydroxy-1-methyl-3-(1H-1,2,4-triazol-1-yl)propyl}-4-{4-[4-(4-fluorophenyl)-1-piperazinyl]phenyl}-3-(2H,4H)-1,2,4-triazolone |
| 12. | 2-{[1R2S/1S2R]-2-(2,4-Difluorophenyl)-2-hydroxy-1-methyl-3-(1H-1,2,4-triazol-1-yl)propyl}-4-{4-[4-(4-fluorophenyl)-1-piperazinyl]phenyl}-3-(2H,4H)-1,2,4-triazolone |
| 13. | 2-{[1R2R/1S2S]-2-(2,4-Difluorophenyl)-2-hydroxy-1-methyl-3-(1H-1,2,4-triazol-1-yl)propyl}-4-{4-[4-(4-methoxyphenyl)-1-piperazinyl]phenyl}-3-(2H,4H)-1,2,4-triazolone |
| 14. | 2-{[1R2S/1S2R]-2-(2,4-Difluorophenyl)-2-hydroxy-1-methyl-3-(1H-1,2,4-triazol-1-yl)propyl}-4-{4-[4-(4-methoxyphenyl)-1-piperazinyl]phenyl}-3-(2H,4H)-1,2,4-triazolone |
| 15. | 2-{[1R2R/1S2S]-2-(2,4-Difluorophenyl)-2-hydroxy-1-methyl-3-(1H-1,2,4-triazol-1-yl)propyl}-4-{4-[4-(3-chloro-4-fluorophenyl)-1-piperazinyl]phenyl}-3-(2H,4H)-1,2,4-triazolone |
| 16. | 2-{[1R2S/1S2R]-2-(2,4-Difluorophenyl)-2-hydroxy-1-methyl-3-(1H-1,2,4-triazol-1-yl)propyl}-4-{4-[4-(3-chloro-4-fluorophenyl)-1-piperazinyl]phenyl}-3-(2H,4H)-1,2,4-triazolone |
| 17. | 2-{[1R2R/1S2S]-2-(2,4-Difluorophenyl)-2-hydroxy-1-methyl-3-(1H-1,2,4-triazol-1-yl)propyl}-4-{4-[4-(3-chloro-4-methylphenyl)-1-piperazinyl]phenyl}-3-(2H,4H)-1,2,4-triazolone |
| 18. | 2-{[1R2S/1S2R]-2-(2,4-Difluorophenyl)-2-hydroxy-1-methyl-3-(1H-1,2,4-triazol-1-yl)propyl}-4-{4-[4-(3-chloro-4-methylphenyl)-1-piperazinyl]phenyl}-3-(2H,4H)-1,2,4-triazolone |
| 19. | 2-{[1R2R/1S2S]-2-(2,4-Difluorophenyl)-2-hydroxy-1-methyl-3-(1H-1,2,4-triazol-1-yl)propyl}-4-{4-[4-(2,4-dimethylphenyl)-1-piperazinyl]phenyl}-3-(2H,4H)-1,2,4-triazolone |
| 20. | 2-{[1R2S/1S2R]-2-(2,4-Difluorophenyl)-2-hydroxy-1-methyl-3-(1H-1,2,4-triazol-1-yl)propyl}-4-{4-[4-(2,4-dimethylphenyl)-1-piperazinyl]phenyl}-3-(2H,4H)-1,2,4-triazolone |
| 21. | 2-{[1R2R/1S2S]-2-(2,4-Difluorophenyl)-2-hydroxy-1-methyl-3-(1H-1,2,4-triazol-1-yl)propyl}-4-{4-[4-(5-chloro-2-methylphenyl)-1-piperazinyl]phenyl}-3-(2H,4H)-1,2,4-triazolone |

-continued

| Compound No. | Chemical Name |
|---|---|
| 22. | 2-{[1R2S/1S2R]-2-(2,4-Difluorophenyl)-2-hydroxy-1-methyl-3-(1H-1,2,4-triazol-1-yl)propyl}-4-{4-[4-(5-chloro-2-methylphenyl)-1-piperazinyl]phenyl}-3-(2H,4H)-1,2,4-triazolone |
| 23. | 2-{[1R2R/1S2S]-2-(2,4-Difluorophenyl)-2-hydroxy-1-methyl-3-(1H-1,2,4-triazol-1-yl)propyl}-4-{4-[4-(3,4-dimethylphenyl)-1-piperazinyl]phenyl}-3-(2H,4H)-1,2,4-triazolone |
| 24. | 2-{[1R2S/1S2R]-2-(2,4-Difluorophenyl)-2-hydroxy-1-methyl-3-(1H-1,2,4-triazol-1-yl)propyl}-4-{4-[4-(3,4-dimethylphenyl)-1-piperazinyl]phenyl}-3-(2H,4H)-1,2,4-triazolone |
| 25. | 2-{[1R2R/1S2S]-2-(2,4-Difluorophenyl)-2-hydroxy-1-methyl-3-(1H-1,2,4-triazol-1-yl)propyl}-4-{4-[4-(2-fluorophenyl)-1-piperazinyl]phenyl}-3-(2H,4H)-1,2,4-triazolone |
| 26. | 2-{[1R2S/1S2R]-2-(2,4-Difluorophenyl)-2-hydroxy-1-methyl-3-(1H-1,2,4-triazol-1-yl)propyl}-4-{4-[4-(2-fluorophenyl)-1-piperazinyl]phenyl}-3-(2H,4H)-5-methyl-1,2,4-triazolone |
| 27. | 2-{[1R2R/1S2S]-2-(2,4-Difluorophenyl)-2-hydroxy-1-methyl-3-(1H-1,2,4-triazol-1-yl)propyl}-4-{4-[4-(2-methoxy-5-fluorophenyl)-1-piperazinyl]phenyl}-3-(2H,4H)-5-methyl-1,2,4-triazolone |
| 28. | 2-{[1R2S/1S2R]-2-(2,4-Difluorophenyl)-2-hydroxy-1-methyl-3-(1H-1,2,4-triazol-1-yl)propyl}-4-{4-[4-(2-methoxy-5-fluorophenyl)-1-piperazinyl]phenyl}-3-(2H,4H)-5-methyl-1,2,4-triazolone |
| 29. | 2-{[1R2R/1S2S]-2-(2,4-Difluorophenyl)-2-hydroxy-1-methyl-3-(1H-1,2,4-triazol-1-yl)propyl}-4-{4-[4-(3,5-dichlorophenyl)-1-piperazinyl]phenyl}-3-(2H,4H)-5-methyl-1,2,4-triazolone |
| 30. | 2-{[1R2S/1S2R]-2-(2,4-Difluorophenyl)-2-hydroxy-1-methyl-3-(1H-1,2,4-triazol-1-yl)propyl}-4-{4-[4-(3,5-dichlorophenyl)-1-piperazinyl]phenyl}-3-(2H,4H)-5-methyl-1,2,4-triazolone |
| 31. | 2-{[1R2R/1S2S]-2-(2,4-Difluorophenyl)-2-hydroxy-1-methyl-3-(1H-1,2,4-triazol-1-yl)propyl}-4-{4-[4-(2-ethylphenyl)-1-piperazinyl]phenyl}-3-(2H,4H)-5-methyl-1,2,4-triazolone |
| 32. | 2-{[1R2S/1S2R]-2-(2,4-Difluorophenyl)-2-hydroxy-1-methyl-3-(1H-1,2,4-triazol-1-yl)propyl}-4-{4-[4-(2-ethylphenyl)-1-piperazinyl]phenyl}-3-(2H,4H)-5-methyl-1,2,4-triazolone |
| 33. | 2-{[1R2R/1S2S]-2-(2,4-Difluorophenyl)-2-hydroxy-1-methyl-3-(1H-1,2,4-triazol-1-yl)propyl}-4-{4-[4-(2,4-dichlorophenyl)-1-piperazinyl]phenyl}-3-(2H,4H)-5-methyl-1,2,4-triazolone |
| 34. | 2-{[1R2S/1S2R]-2-(2,4-Difluorophenyl)-2-hydroxy-1-methyl-3-(1H-1,2,4-triazol-1-yl)propyl}-4-{4-[4-(2,4-dichlorophenyl)-1-piperazinyl]phenyl}-3-(2H,4H)-5-methyl-1,2,4-triazolone |
| 35. | 2-[2-(2,4-Difluorophenyl)-2-hydroxy-3-(1H-1,2,4-triazol-1-yl)propyl]-4-{4-[4-(2-methoxyphenyl)-1-piperazinyl]phenyl}-3-(2H,4H)-5-methyl-1,2,4-triazolone |
| 36. | 2-[2-(2,4-Difluorophenyl)-2-hydroxy-3-(1H-1,2,4-triazol-1-yl)propyl]-4-{4-[4-(4-fluorophenyl)-1-piperazinyl]phenyl}-3-(2H,4H)-5-methyl-1,2,4-triazolone |
| 37. | 2-[2-(2,4-Difluorophenyl)-2-hydroxy-3-(1H-1,2,4-triazol-1-yl)propyl]-4-{4-[4-(3,4-dichlorophenyl)-1-piperazinyl]phenyl}-3-(2H,4H)-1,2,4-triazolone |
| 38. | 2-[2-(2,4-Difluorophenyl)-2-hydroxy-3-(1H-1,2,4-triazol-1-yl)propyl]-4-{4-[4-(2,4-diaminophenyl)-1-piperazinyl]phenyl}-3-(2H,4H)-1,2,4-triazolone |
| 39. | 2-[2-(2,4-Difluorophenyl)-2-hydroxy-3-(1H-1,2,4-triazol-1-yl)propyl]-4-{4-[4-(4-methylphenyl)-1-piperazinyl]phenyl}-3-(2H,4H)-1,2,4-triazolone |
| 40. | 2-[2-(2,4-Difluorophenyl)-2-hydroxy-3-(1H-1,2,4-triazol-1-yl)propyl]-4-{4-[4-(2,4-dinitrophenyl)-1-piperazinyl]phenyl}-3-(2H,4H)-1,2,4-triazolone |
| 41. | 2-[2-(2,4-Difluorophenyl)-2-hydroxy-3-(1H-1,2,4-triazol-1-yl)propyl]-4-{4-[4-(4-methoxyphenyl)-1-piperazinyl]phenyl}-3-(2H,4H)-1,2,4-triazolone |
| 42. | 2-[2-(2,4-Difluorophenyl)-2-hydroxy-3-(1H-1,2,4-triazol-1-yl)propyl]-4-{4-[4-(2-methoxyphenyl)-1-piperazinyl]phenyl}-3-(2H,4H)-1,2,4-triazolone |
| 43. | 2-[2-(2,4-Difluorophenyl)-2-hydroxy-3-(1H-1,2,4-triazol-1-yl)propyl]-4-{4-[4-(4-fluorophenyl)-1-piperazinyl]phenyl}-3-(2H,4H)-1,2,4-triazolone |
| 44. | 2-[2-(2,4-Difluorophenyl)-2-hydroxy-3-(1H-1,2,4-triazol-1-yl)propyl]-4-{4-[4-(4-hydroxyphenyl)-1-piperazinyl]phenyl}-3-(2H,4H)-1,2,4-triazolone |
| 45. | 2-[2-(2,4-Difluorophenyl)-2-hydroxy-3-(1H-1,2,4-triazol-1-yl)propyl]-4-{4-[1-phenyl-1-piperazinyl]phenyl}-3-(2H,4H)-1,2,4-triazolone |
| 46. | 2-[2-(2,4-Difluorophenyl)-2-hydroxy-3-(1H-1,2,4-triazol-1-yl)propyl]-4-{4-[4-(4-chlorophenyl)-1-piperazinyl]phenyl}-3-(2H,4H)-5-methyl-1,2,4-triazolone |
| 47. | 2-[2-(2,4-Difluorophenyl)-2-hydroxy-3-(1H-1,2,4-triazol-1-yl)propyl]-4-{4-[4-(4-chlorophenyl)-1-piperazinyl]phenyl}-3-(2H,4H)-1,2,4-triazolone |
| 48. | 2-[2-(2,4-Difluorophenyl)-2-hydroxy-3-(1H-1,2,4-triazol-1-yl)propyl]-4-{4-[4-(5-chloro-2-methylphenyl)-1-piperazinyl]phenyl}-3-(2H,4H)-1,2,4-triazolone |
| 49. | 2-[2-(2,4-Difluorophenyl)-2-hydroxy-3-(1H-1,2,4-triazol-1-yl)propyl]-4-{4-[4-(3-chloro-4-methylphenyl)-1-piperazinyl]phenyl}-3-(2H,4H)-1,2,4-triazolone |
| 50. | 2-[2-(2,4-Difluorophenyl)-2-hydroxy-3-(1H-1,2,4-triazol-1-yl)propyl]-4-{4-[4-(2,4-dichlorophenyl)-1-piperazinyl]phenyl}-3-(2H,4H)-1,2,4-triazolone |
| 51. | 2-[2-(2,4-Difluorophenyl)-2-hydroxy-3-(1H-1,2,4-triazol-1-yl)propyl]-4-{4-[4-(3-trifluoromethylphenyl)-1-piperazinyl]phenyl}-3-(2H,4H)-1,2,4-triazolone |
| 52. | 2-[2-(2,4-Difluorophenyl)-2-hydroxy-3-(1H-1,2,4-triazol-1-yl)propyl]-4-{4-[4-(2,4-difluorophenyl)-1-piperazinyl]phenyl}-3-(2H,4H)-1,2,4-triazolone |
| 53. | 2-[2-(2,4-Difluorophenyl)-2-hydroxy-3-(1H-1,2,4-triazol-1-yl)propyl]-4-{4-[4-(3-chloro-4-fluorophenyl)-1-piperazinyl]phenyl}-3-(2H,4H)-1,2,4-triazolone |
| 54. | 2-[2-(2,4-Difluorophenyl)-2-hydroxy-3-(1H-1,2,4-triazol-1-yl)propyl]-4-{4-[4-(2,4-dimethylphenyl)-1-piperazinyl]phenyl}-3-(2H,4H)-1,2,4-triazolone |
| 55. | 2-[2-(2,4-Difluorophenyl)-2-hydroxy-3-(1H-1,2,4-triazol-1-yl)propyl]-4-{4-[4-(3,4-difluorophenyl)-1-piperazinyl]phenyl}-3-(2H,4H)-1,2,4-triazolone |
| 56. | 2-[2-(2,4-Difluorophenyl)-2-hydroxy-3-(1H-1,2,4-triazol-1-yl)propyl]-4-{4-[4-(3,4-dimethylphenyl)-1-piperazinyl]phenyl}-3-(2H,4H)-1,2,4-triazolone |
| 57. | 2-[2-(2,4-Difluorophenyl)-2-hydroxy-3-(1H-1,2,4-triazol-1-yl)propyl]-4-{4-[4-(3-chlorophenyl)-1-piperazinyl]phenyl}-3-(2H,4H)-1,2,4-triazolone |
| 58. | 2-[2-(2,4-Difluorophenyl)-2-hydroxy-3-(1H-1,2,4-triazol-1-yl)propyl]-4-{4-[4-(2-chloro-4-fluorophenyl)-1-piperazinyl]phenyl}-3-(2H,4H)-1,2,4-triazolone |
| 59. | 2-[2-(2,4-Difluorophenyl)-2-hydroxy-3-(1H-1,2,4-triazol-1-yl)propyl]-4-{4-[4-(2-methoxy-5-fluorophenyl)-1-piperazinyl]phenyl}-3-(2H,4H)-1,2,4-triazolone |

-continued

| Compound No. | Chemical Name |
|---|---|
| 60. | 2-[2-(2,4-Difluorophenyl)-2-hydroxy-3-(1H-1,2,4-triazol-1-yl)propyl]-4-{4-[4-(2-ethylphenyl)-1-piperazinyl]phenyl}-3-(2H,4H)-1,2,4-triazolone |
| 61. | 2-[2-(2,4-Difluorophenyl)-2-hydroxy-3-(1H-1,2,4-triazol-1-yl)propyl]-4-{4-[4-(3,5-dichlorophenyl)-1-piperazinyl]phenyl}-3-(2H,4H)-1,2,4-triazolone |
| 62. | 2-[2-(2,4-Difluorophenyl)-2-hydroxy-3-(1H-1,2,4-triazol-1-yl)propyl]-4-{4-[4-(2-fluorophenyl)-1-piperazinyl]phenyl}-3-(2H,4H)-1,2,4-triazolone |
| 63. | 2-[2-(2,4-Difluorophenyl)-2-hydroxy-3-(1H-1,2,4-triazol-1-yl)propyl]-4-{4-[4-(2,3,4-trifluorophenyl)-1-piperazinyl]phenyl}-3-(2H,4H)-1,2,4-triazolone |
| 64. | 3-{4-[4-(p-Tolylthioureido)piperazinyl]phenoxy}-2-(2,4-difluorophenyl)-1-(1H-1,2,4-trizol-1-yl)-propan-2-ol. |
| 65. | 3-{4-[4-(Isopropylaminothiocarbonylamino)piperazinyl]phenoxy}-2-(2,4-difluorophenyl)-1-(1H-1,2,4-triazol-1-yl)-propan-2-ol. |
| 66. | 3-{4-[4-(4-Chlorophenylthioureido)piperazinyl]phenoxy}-2-(2,4-difluorophenyl)-1-(1H-1,2,4-triazol-1-yl)-propan-2-ol. |
| 67. | 3-{4-[4-(4-Chlorophenylureido)piperazinyl]phenoxy}-2-(2,4-difluorophenyl)-1-(1H-1,2,4-triazol-1-yl)-propan-2-ol. |
| 68. | 3-{4-[4-(1-Napthylthioureido)piperazinyl]phenoxy}-2-(2,4-difluorophenyl)-1-(1H-1,2,4-triazol-1-yl)-propan-2-ol. |
| 69. | 3-{4-[4-(1-Napthylureido)piperazinyl]phenoxy}-2-(2,4-difluorophenyl)-1-(1H-1,2,4-triazol-1-yl)-propan-2-ol. |
| 70. | 3-{4-[4-(4-Trifluoromethylphenylthioureido)piperazinyl]phenoxy}-2-(2,4-difluorophenyl)-1-(1H-1,2,4-triazol-1-yl)-propan-2-ol. |
| 71. | 3-{4-[4-(4-Methoxyphenylureido)piperazinyl]phenoxy}-2-(2,4-difluorophenyl)-1-(1H-1,2,4-triazol-1-yl)-propan-2-ol. |
| 72. | 3-{4-[4-(2,4-Dichlorophenylureido)piperazinyl]phenoxy}-2-(2,4-difluorophenyl)-1-(1H-1,2,4-triazol-1-yl)-propan-2-ol. |
| 73. | 3-{4-[4-(4-chlorophenyl-N-ethylureido)-piperazinyl]-phenoxy}-2-(2,4-difluorophenyl)-1-(1H-1,2,4-triazolyl)-propan-3-amino-2-ol |
| 74. | 3-{4-[4-(4-chlorophenyl-N-ethylureido)-piperazinyl]-phenoxy}-2-(2,4-difluorophenyl)-1-(1H-1,2,4-triazolyl)-2-ethoxy-3-propylamine |
| 75. | 3-{4-[4-N-(4-Chlorophenyl)-N-(methylureido)-piperazinyl]-phenoxy}-2-(2,4-difluorophenyl)-1-(1H-1,2,4-triazolyl)-2-methoxypropane. |
| 76. | 3-{4-[4-(4-Aminophenylureido)piperazinyl]phenoxy}-2-(2,4-difluorophenyl)-1-(1H-1,2,4-triazol-1-yl)-propan-2-ol. |
| 77. | [1R2R/1S2S] 1-{4-[4-(4-Chlorophenylureido)-piperazinyl]-phenoxy}-2-(2,4-difluorophenyl)-1-methyl-3-(1H-1,2,4-triazolyl)-propan-2-ol |
| 78. | [1R2S/1S2R] 1-{4-[4-(4-Chlorophenylureido)-piperazinyl]-phenoxy}2-(2,4-difluorophenyl)-1-methyl-3-(1H-1,2,4-triazolyl)-propan-2-ol |
| 79. | 1-{4-[4-(4-Trifluoromethylphenylureido)piperazinyl]phenoxy}-2-(2,4-difluorophenyl)-1-methyl-3-(1H-1,2,4-triazol-1-yl)-propan-2-ol. |
| 80. | 3-{4-[4-(Phenylureido)-piperazinyl]phenoxy}-2-(2,4-difluorophenyl)-1-(1H-1,2,4-triazol-1-yl)-propan-2-ol. |
| 81. | 3-{N-[4-(Phenylthioureido)-phenyl]-N-methyl}-2-(2,4-Difluorophenyl)-1-(1H-1,2,4-triazolyl)-propan-3-amino-2-ol |
| 82. | 3-{N-[4-(Isopropylthioureido)-phenyl]-N-methyl}-2-(2,4-difluorophenyl)-1-(1H-1,2,4-triazolyl)-propan-3-amino-2-ol |
| 83. | 3-{N-[4-(p-Tolylthioureido)-phenyl]-N-methyl}-2-(2,4-difluorophenyl)-1-(1H-1,2,4-triazolyl)-propan-3-amino-2-ol |
| 84. | 3-{N-[4-(p-Fluorophenylureido)-phenyl]-N-methyl}-2-(2,4-difluorophenyl)-1-(1H-1,2,4-triazolyl)-propan-3-amino-2-ol |
| 85. | 3-{N-[4-(p-nitrophenylureido)-phenyl]-N-methyl}-2-(2,4-Difluorophenyl)-1-(1H-1,2,4-triazolyl)-propan-3-amino-2-ol |
| 86. | 3-{N-[4-(p-Chlorophenylureido)-phenyl]-N-methyl}-2-(2,4-difluorophenyl)-1-(1H-1,2,4-triazolyl)-propan-3-amino-2-ol |
| 87. | 3-{N-[4-(Carboxymethyl)-phenylureido)-phenyl]-N-methyl}-2-(2,4-difluorophenyl)-1-(1H-1,2,4-triazolyl)-propan-3-amino-2-ol |
| 88. | 3-{N-[4-((2-Methoxy-2-oxoethyl)-phenylureido)-phenyl]-N-methyl}-2-(2,4-difluorophenyl)-1-(1H-1,2,4-triazolyl)-propan-3-amino-2-ol |
| 89. | 3-{N-[4-((p-Chlorophenylthioureido)-phenylureido)-phenyl]-N-methyl}-2-(2,4-difluorophenyl)-1-(1H-1,2,4-triazolyl)-propan-3-amino-2-ol |
| 90. | 2-[2-(2,4-Difluorophenyl)-2-hydroxy-3-(1H-1,2,4-triazol-1-yl)propyl]-4-{4-[4-(isopropylthiouredio)-1-piperazinyl]phenyl}-3-(2H,4H)-1,2,4-triazolone |
| 91. | 2-[2-(2,4-Difluorophenyl)-2-hydroxy-3-(1H-1,2,4-triazol-1-yl)propyl]-4-{4-[4-(4-chlorophenyluredio)-1-piperazinyl]phenyl}-3-(2H,4H)-1,2,4-triazolone |
| 92. | 2-[2-(2,4-Difluorophenyl)-2-hydroxy-3-(1H-1,2,4-triazol-1-yl)propyl]-4-{4-[4-(4-chlorophenylthiouredio)-1-piperazinyl]phenyl}-3-(2H,4H)-1,2,4-triazolone |
| 93. | 2-[2-(2,4-Difluorophenyl)-2-hydroxy-3-(1H-1,2,4-triazol-1-yl)propyl]-4-{4-[4-(4-(2-methoxy-2-oxoethyl)phenyl)-1-piperazinyl]phenyl}-3-(2H,4H)-1,2,4-triazolone |
| 94. | 2-[2-(2,4-Difluorophenyl)-2-hydroxy-3-(1H-1,2,4-triazol-1-yl)propyl]-4-{4-[4-(4-(carboxyethyl)-phenyl)-1-piperazinyl]phenyl}-3-(2H,4H)-1,2,4-triazolone |
| 95. | 2-[2-(2,4-Difluorophenyl)-2-hydroxy-3-(1H-1,2,4-triazol-1-yl)propyl]-4-{4-[4-(4-(2-hydroxyethyl)phenyl)-1-piperazinyl]phenyl}-3-(2H,4H)-1,2,4-triazolone |

Preferred group of compounds belonging to the compounds of Formulae IA, IB, II and III of the present invention are exemplified in Table I to Table IV though the present invention is not limited to the compounds given there.

TABLE I

FORMULA IA (X = CH$_2$, R = F, Y = C$_6$H$_4$-, R$_3$ = H)

A. LIST OF α-METHYL ANALOGUES

| Compound No. | R$_1$ | R$_2$ | X$_1$ | Y$_1$ | Z | Y$_2$ | X$_2$ | Comments (*) | m.p (° C.) |
|---|---|---|---|---|---|---|---|---|---|
| 1 | CH$_3$ | H | H | H | Cl | H | H | (RR, SS) | 192–196 |
| 2 | CH$_3$ | H | H | H | Cl | H | H | (RS, SR) | 220–222 |
| 3 | CH$_3$ | H | NO$_2$ | H | NO$_2$ | H | H | (RR, SS) | 155–160 |
| 4 | CH$_3$ | H | NO$_2$ | H | NO$_2$ | H | H | (RS, SR) | 153–155 |
| 5 | CH$_3$ | H | H | H | H | H | H | (RR, SS) | 212–214 |
| 6 | CH$_3$ | H | H | H | H | H | H | (RS, SR) | 205–207 |
| 7 | CH$_3$ | H | H | Cl | Cl | H | H | (RR, SS) | 102–105 |
| 8 | CH$_3$ | H | H | Cl | Cl | H | H | (RS, SR) | 233–240 |
| 9 | CH$_3$ | H | H | CF$_3$ | H | H | H | (RR, SS) | 182–186 |
| 10 | CH$_3$ | H | H | CF$_3$ | H | H | H | (RS, SR) | 170–172 |
| 11 | CH$_3$ | H | H | H | F | H | H | (RR, SS) | 174–177 |
| 12 | CH$_3$ | H | H | H | F | H | H | (RS, SR) | 218–219 |
| 13 | CH$_3$ | H | H | H | OCH$_3$ | H | H | (RR, SS) | 180–185 |
| 14 | CH$_3$ | H | H | H | OCH$_3$ | H | H | (RS, SR) | 106–111 |
| 15 | CH$_3$ | H | H | Cl | F | H | H | (RR, SS) | 148–150 |
| 16 | CH$_3$ | H | H | Cl | F | H | H | (RS, SR) | 194–197 |
| 17 | CH$_3$ | H | H | Cl | CH$_3$ | H | H | (RR, SS) | 156–158 |
| 18 | CH$_3$ | H | H | Cl | CH$_3$ | H | H | (RS, SR) | 148–150 |
| 19 | CH$_3$ | H | CH$_3$ | H | CH$_3$ | H | H | (RR, SS) | 201–202 |
| 20 | CH$_3$ | H | CH$_3$ | H | CH$_3$ | H | H | (RS, SR) | 92–94 |
| 21 | CH$_3$ | H | CH$_3$ | H | H | Cl | H | (RR, SS) | Foam |
| 22 | CH$_3$ | H | CH$_3$ | H | H | Cl | H | (RS, SR) | Foam |
| 23 | CH$_3$ | H | H | CH$_3$ | CH$_3$ | H | H | (RR, SS) | Gummy |
| 24 | CH$_3$ | H | H | CH$_3$ | CH$_3$ | H | H | (RS, SR) | Gummy |
| 25 | CH$_3$ | H | F | H | H | H | H | (RR, SS) | Gummy |
| 26 | CH$_3$ | H | F | H | H | H | H | (RS, SR) | 179–181 |
| 27 | CH$_3$ | H | OCH$_3$ | H | H | F | H | (RR, SS) | 83–85 |
| 28 | CH$_3$ | H | OCH$_3$ | H | H | F | H | (RS, SR) | 90–93 |
| 29 | CH$_3$ | H | H | Cl | H | Cl | H | (RR, SS) | 188–191 |
| 30 | CH$_3$ | H | H | Cl | H | Cl | H | (RS, SR) | 207–210 |
| 31 | CH$_3$ | H | C$_2$H$_5$ | H | H | H | H | (RR, SS) | 142–145 |
| 32 | CH$_3$ | H | C$_2$H$_5$ | H | H | H | H | (RS, SR) | 177–178 |
| 33 | CH$_3$ | H | Cl | H | Cl | H | H | (RR, SS) | Foam |
| 34 | CH$_3$ | H | Cl | H | Cl | H | H | (RS, SR) | Foam |

B. LIST OF non-α-METHYL ANALOGUES

| Compound No. | R$_1$ | R$_2$ | X$_1$ | Y$_1$ | Z | Y$_2$ | X$_1$ | m.p (° C.) |
|---|---|---|---|---|---|---|---|---|
| 35 | H | CH$_3$ | OCH$_3$ | H | H | H | H | 144–149 |
| 36 | H | CH$_3$ | H | H | F | H | H | 188–189 |
| 37 | H | H | H | Cl | Cl | H | H | 194–196 |
| 38 | H | H | NH$_2$ | H | NH$_2$ | H | H | 215–222 |
| 39 | H | H | H | H | CH$_3$ | H | H | 146–148 |
| 40 | H | H | NO$_2$ | H | NO$_2$ | H | H | 120–123 |
| 41 | H | H | H | H | OCH$_3$ | H | H | 183–186 |
| 42 | H | H | OCH$_3$ | H | H | H | H | 95–97 |
| 43 | H | H | H | H | F | H | H | 173–177 |
| 44 | H | H | H | H | OH | H | H | 246–248 |
| 45 | H | H | H | H | H | H | H | 170–172 |
| 46 | H | CH$_3$ | H | H | Cl | H | H | 88–94 |
| 47 | H | H | H | H | Cl | H | H | 207–208 |
| 48 | H | H | CH$_3$ | H | H | Cl | H | 82–87 |
| 49 | H | H | H | H | CH$_3$ | Cl | H | 189–201 |
| 50 | H | H | Cl | H | Cl | H | H | 97–99 |
| 51 | H | H | H | CF$_3$ | H | H | H | 166–168 |
| 52 | H | H | F | H | F | H | H | 157–158 |
| 53 | H | H | H | Cl | F | H | H | 182–85 |
| 54 | H | H | CH$_3$ | H | CH$_3$ | H | H | 76–77 |
| 55 | H | H | H | F | F | H | H | 117–118 |
| 56 | H | H | H | CH$_3$ | CH$_3$ | H | H | 136–137 |
| 57 | H | H | H | Cl | H | H | H | 177–78 |
| 58 | H | H | Cl | H | F | H | H | Oil |
| 59 | H | H | OCH$_3$ | H | H | F | H | Gummy |

TABLE I-continued
FORMULA IA (X = CH₂, R = F, Y = C₆H₄-, R₃ = H)
| 60 | H | H | C₂H₅ | H | H | H | H | 148–150 |
| 61 | H | H | H | Cl | H | Cl | H | 222–225 |
| 62 | H | H | F | H | H | H | H | 74–76 |
| 63 | H | H | F | F | F | H | H | 186–187 |
TABLE II
(FORMULA II)
(X = CH₂, R = F, Y = C₆H₄—)
| Compound No. | $R_4$ | B | $R_1$ | $R_4$ | $R_5$ | m.p. °C. | MIC (υg/ml) (*A. fumigatus* s 1008) |
|---|---|---|---|---|---|---|---|
| 64 | H | S | H | H | 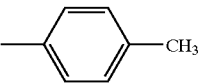 | 192–194 | 3.12 |
| 65 | H | S | H | H | —CH(CH₃)₂ | 75–78 | >12.5 |
| 66 | H | S | H | H |  | 138 | >12.5 |
| 67 | H | O | H | H | 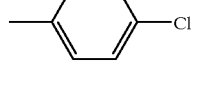 | 136–137 | 6.25 |
| 68 | H | S | H | H | 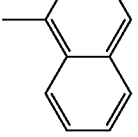 | 109–111 | >12.5 |
| 69 | H | O | H | H | 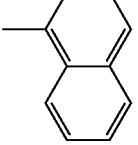 | 138–139 | >12.5 |
| 70 | H | S | H | H | 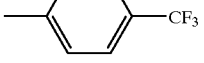 | 150–151 | >12.5 |
| 71 | H | O | H | H | 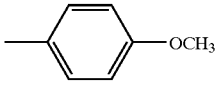 | Gummy | >12.5 |
| 72 | H | O | H | H | 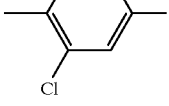 | Gummy | >12.5 |
| 73 | H | O | H | C₂H₅ | 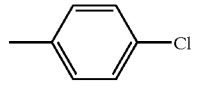 | Gummy | >12.5 |
| 74 | C₂H₅ | O | H | C₂H₅ | 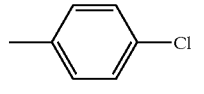 | Gummy | >12.5 |

TABLE II-continued (FORMULA II)
(X = CH$_2$, R = F, Y = C$_6$H$_4$—)

| Compound No. | R$_4$ | B | R$_1$ | R$_4$ | R$_5$ | m.p. ° C. | MIC (υg/ml) (*A. fumigatus* s 1008) |
|---|---|---|---|---|---|---|---|
| 75 | CH$_3$ | O | H | CH$_3$ | 4-Cl-C$_6$H$_4$— | Gummy | >12.5 |
| 76 | H | O | H | H | 4-NH$_2$-C$_6$H$_4$— | Gummy | >12.5 |
| 77 | H | O | CH$_3$ | H | 4-Cl-C$_6$H$_4$— | 106–108 | 2 |
| 78 | H | O | CH$_3$ | H | 4-Cl-C$_6$H$_4$— | 105–107 | 0.5 |
| 79 | H | O | CH$_3$ | H | 3-CF$_3$-C$_6$H$_4$— | Gummy | 8 |
| 80 | H | S | H | H | C$_6$H$_5$— | 154–156 | >12.5 |

TABLE III (FORMULA III)
(X = CH$_2$, R = F, Y = C$_6$H$_4$—)

| Compound No. | B | R$_1$ | R$_5$ | m.p. ° C. | MIC (υg/ml) (*A. fumigatus* s 1008) |
|---|---|---|---|---|---|
| 81 | S | H | C$_6$H$_5$— | 147–150 | >12.5 |
| 82 | S | H | —CH(CH$_3$)$_2$ | 76 | >12.5 |
| 83 | S | H | 4-CH$_3$-C$_6$H$_4$— | 174 | >12.5 |
| 84 | O | H | 4-F-C$_6$H$_4$— | 160–164 | >12.5 |
| 85 | O | H | 4-NO$_2$-C$_6$H$_4$— | 87–88 | >12.5 |
| 86 | O | H | 4-Cl-C$_6$H$_4$— | 174–176 | >12.5 |
| 87 | O | H | 4-CH$_3$COOH-C$_6$H$_4$— | Gummy | >12.5 |

TABLE III-continued (FORMULA III)
(X = CH$_2$, R = F, Y = C$_6$H$_4$—)

| Compound No. | B | R$_1$ | R$_5$ | m.p. ° C. | MIC (υg/ml) (A. fumigatus s 1008) |
|---|---|---|---|---|---|
| 88 | O | H | —C$_6$H$_4$—CH$_2$COOCH$_3$ | Gummy | >12.5 |
| 89 | S | H | —C$_6$H$_4$—Cl | 162–164 | >12.5 |

TABLE IV (FORMULA IB)
(X = CH$_2$, R = F, Y = C$_6$H$_4$—, R$_1$, R$_2$, R$_3$ and R$_4$ = H)

| Compound No. | B | R$_1$ | R$_5$ | m.p. ° C. | MIC (υg/ml) (A. fumigatus s 1008) |
|---|---|---|---|---|---|
| 90 | S | H | —CH(CH$_3$)$_2$ | Gummy solid | >12.5 |
| 91 | O | H | —C$_6$H$_4$—Cl | 149–153 | >12.5 |
| 92 | S | H | —C$_6$H$_4$—Cl | 142–144 | >12.5 |
| 93 | O | H | —C$_6$H$_4$—CH$_2$COOCH$_3$ | 66–69 | >12.5 |
| 94 | O | H | —C$_6$H$_4$—CH$_3$COOH | 235–239 | >12.5 |
| 95 | O | H | —C$_6$H$_4$—CH$_2$—CH$_2$—OH | 114–115 | >12.5 |

All compounds mentioned in the above list as well as the compounds mentioned in formulae IA, IB, II and III with a variety of substituents were prepared using the methods described earlier depending upon whether they are mixtures of α-methylated isomers, mixtures of non α-methylated isomers or pure RR isomers.

The examples mentioned below demonstrate the general synthetic procedure as well as the specific preparation for the preferred compound. The examples are given to illustrate the details of the invention and should not be constrained to limit the scope of the present invention.

Most of the compounds were characterized using NMR, IR and were purified by chromatography. Crude products were subjected to column chromatographic purification using silica gel (100–200 or 60–120 mesh) as stationary phase.

EXAMPLE 1

Preparation of 2-{2-[(2,4-Difluorophenyl)-2-hydroxy-3-(1H-1,2,4-triazol-1-yl)propyl]}-4-{[4-[4-(substituted/unsubstituted phenyl)-1-piperazinyl]phenyl]}-3-(2H,4H)-1,2,-substituted Triazol-4-one Step 1: Preparation of 2-Chloro-2',4'-difluoro Acetophenone.

Into the solution of 1,3-difluorobenzene in 1,2-dicholoroethane (DCE) was added anhydrous aluminium chloride (1.2 molar equivalent of 1,3-difluorobenzene) at 25–30° C. and stirred for 30 minutes. The reaction mixture was then cooled to 0° C. and chloroacetyl chloride (1.1 molar equivalent of 1,3-difluorobenzene), in DCE, was then added into it over a period of 30–60 min keeping the reaction temperature below 20° C. After the addition was over, the reaction mixture was stirred at 25–30° C. for 5–7 hours. The reaction mixture was then diluted with DCE and poured into dil. hydrochloric acid (5%) at 0–5° C. The mixture was then extracted with DCE. The combined organic layer was washed successively with 5% aq. sodium bicarbonate solution and water. Evaporating DCE from the organic layer under reduced pressure gave an oil which on triturating with n-Hexane gave the title compound as white crystalline material (Yield 75% of theory).

Step 2: Preparation of 2-(1H,2,4-Triazol-1-yl)-2',4'-difluoro Acetophenone

The product obtained in Step-1 was reacted with 1,2,4-triazole (1.2 molar equivalent) in the presence of sodium bicarbonate as base and toluene as solvent under refluxing condition. After the reaction was over, the reaction mixture was poured into crushed ice and extracted with toluene. The combined organic layer was then washed with water and concentrated under reduced pressure to give brown semisolid compound which was recrystallized from ethyl acetate—hexane mixture to give light yellow solid compound which was then used as such in the next step.

Step 3: Preparation of 1-[2-(2,4-Difluorophenyl)-2,3-epoxypropyl]-1H-1,2,4-triazole Step 2 product was dissolved in toluene, followed by the addition of trimethylsulfoxonium iodide (TMSI), cetramide and 20% aq. sodium hydroxide solution. This mixture was then heated at 60° C. for 4 hrs. After the reaction was over, it was diluted with toluene and poured into chilled water. The organic layer was washed with water and concentrated under reduced pressure to give light brown oil which was used after column chromatographic purification (silica gel) in the next step.

Step 4: Preparation of 1-(Substituted phenyl)-4-(4-nitrophenyl)piperazine.

Substituted phenyl piperazine was reacted with 4-chloronitrobenzene (1.1 molar equivalent of phenyl piperazine) in dimethylsulphoxide [DMSO] (5 times) using anhydrous potassium carbonate (1.5 molar equivalent) at a temperature 135–140° C. for 6 to 8 hrs. The reaction mixture was poured into crushed ice and the compound was isolated either as a solid or by extracting with chlorinated organic solvent. After drying under vacuum at 30–35° C. for 6–8 hrs, the compound was used as such for next step.

Step 5: Preparation of 1-(Substituted Phenyl)-4-(4-aminophenyl)piperazine

The nitro compound was then reduced to amine by two methods:

Method 1: The compound of Step 4 was dissolved in methanol and Palladium on charcoal (wet, 10% w/w) was added under nitrogen followed by the addition of ammonium formate (5 molar equivalent). The reaction mixture was then stirred at a temperature ranging from 45 to 70° C. until the reaction went to completion. After the reaction was over, the reaction mixture was then cooled to 25–30° C. and filtered. The filtrate was then concentrated under reduced pressure to give a residue which was again dissolved in dichloroethane and washed with water. The organic layer on concentration gave the desired product.

Method 2: The compound of Step 4 was refluxed in ethyl acetate in the presence of 5.0 molar equivalent stannous chloride dihydrate for 6–8 hrs. After completion of the reaction, the reaction mixture was poured into 10% aq. sodium bicarbonate and extracted with ethyl acetate. The combined organic layer was then washed with water dried over anhydrous sodium sulfate and concentrated under reduced pressure to give the desired product.

Step 6: Preparation of [4-(4-(Substituted/unsubstituted Phenyl)-1-piperazinyl]phenyl Carbamate The amine obtained from Step 5 was dissolved in a mixture of dichloroethane (DCE) and pyridine and cooled to 5° C. A solution of phenylchloroformate (1.4 molar equivalent) in DCE was added into the solution of amine at such a rate that reaction temperature remained below 35° C. After the addition was over, reaction mixture was stirred at 25–30° C. for 3–5 hours. Solvent was evaporated off under reduced pressure to give brownish residue which on triturating with n-hexane gave brown solid. It was then obtained was washed with 5% aq. solution of sodium bicarbonate and water. It was then dried under vacuum at 40° C. for 3 to 5 hrs to give the corresponding carbamate.

Step 7: Preparation of N-[4-[(4-Substituted Phenyl) 1-Piperazinyl]phenyl]hydrazine Carboxamide.

The carbamate obtained in Step 6 was stirred in 1,4-dioxane followed by the addition of hydrazine hydrate (2.5 molar equivalent 98%) at room temperature. After refluxing the reaction mixture for 4 to 6 hrs, solvent was evaporated off to give solid residue which was triturated with 10% methanol in diethyl ether, filtered the separated solid and dried under vacuum at 35–40° C. for 4 to 6 hrs to give corresponding semicarbazide.

Step 8: 4-(4-Substituted Phenyl)-1-piperazinlphenyl-3H-1,2,4-triazol-3-ones.

The semicarbazide so obtained was dissolved in dry dimethylformamide (DMF) followed by the addition of formamidine acetate (4.5 molar equivalent). After heating at 120–130° C. for 3 to 5 hrs, reaction mixture was poured into chilled saturated aq. solution of sodium bicarbonate with stirring. Solid so obtained was filtered, washed with water and dried under vacuum at 40° C. for 7 hrs. to give corresponding triazolone.

Step 9: Preparation of 2-[(2,4-Difluorophenyl)-2-hydroxy-3-(1H-1,2,4-triazol-1-yl)-propyl]-4-[4-[4-substitutedphenyl-1-piperazinyl]phenyl]-3-(2H,4H)-1,2,3-substituted Triazol-4-one.

Hexane washed sodium hydride (0.015 mg, 1.0 mmol) was added into a stirred solution of compound obtained from Step-8 (0.4 g, 1.12 mmol) in dimethyl formamide (DMF) (10 ml) maintaining nitrogen atmosphere. After stirring at 25–30° C., a solution of the compound obtained from Step 3 (1.68 mmol) in DMF was added drop-wise into the reaction mixture at 40° C., temperature was raised to 80° C. and maintained at this temperature for about 4 hr. After the reaction was over, reaction mixture was cooled to 35–40° C., poured it into chilled water (50 ml) and extracted with ethyl acetate (3×100 ml). The combined organic layer was washed with water (4×50 ml), dried over anhydrous sodium sulphate and concentrated under vacuum to give an oily residue (0.3 gm). The oil was purified by column chromatography (silica gel 100–200 mesh) using hexane-ethyl acetate (1:1) followed by ethyl acetate or by crystallisation from suitable solvent to give the required compound.

EXAMPLE 2

Preparation of 2-{[1R,2R/1S,2S/1R,2S/1S,2R]2[(2,4-Difluorophenyl)-2-hydroxy-1-methyl-3-(1H-1,2,4-triazol-1-yl)propyl]}-4-{[4-[4-substituted/unsubstituted)phenyl-1-piperazinyl]phenyl]}-3-(2H,4H)-1,2,3-substituted Triazol-4-one Step 1: Preparation of 2-Chloro-2-methyl-2',4'-difluoro Acetophenone Into the solution of 1,3-Difluorobenzene in 1,2-dichoroethane (DCE) was added anhydrous aluminium chloride (1.2 mol eqnt.) at 25–30° C. and stirred for 30 minutes. The reaction mixture was then cooled to 0° C. and (±)2-chloropropionyl chloride (1.1 molar equivalent), diluted in DCE, was then added into it over a period of 30–60 min keeping the reaction temperature below 20° C. After the addition was over, reaction mixture was stirred at room temperature for 5–7 hours. For workup, reaction mixture was diluted with DCE and poured into chilled aq. hydrochloric acid solution (5%). The mixture was extracted with DCE and the combined organic layer was washed with 5% aq. sodium bicarbonate solution and water. The solvent was evaporated off under reduced pressure to afford an oil.

Step 2: Preparation of 2-{[4-[4-[4-(Substituted/unsubstituted Phenyl)piperazin-yl]phenyl-(2H,4H)-1,2,4-triazol-3-one-2-yl]}-2(R/S)-methyl-2',4'-difluoroacetophenone Hexane washed sodium hydride (1.2 molar equivalent) was added into a stirred solution of compound of Formula XII (1.0 molar equivalent) in dimethylsulphoxide (DMSO) maintained under nitrogen atmosphere. After stirring at 25–30° C. for 1 hr, a solution of the compound of Formula XIV (2 molar equivalent) in DMSO was added dropwise into the reaction mixture at about 152° C. The reaction mixture was then stirred at 25–30° C. for 2 hrs and slowly the temperature was raised to 60° C. and maintained this temperature for 3–4 hrs. After the reaction was over, reaction mixture was cooled to 25–30° C., poured into chilled water and extracted with ethyl acetate. The combined organic layer was washed with water, dried over anhydrous sodium sulphate and concentrated to give an oily residue under vacuum. The crude product was purified by column chromatography (silica gel 100–200 mesh) using hexane-ethyl acetate (1:1) followed by using ethyl acetate to give the required compound.

Step 3: Preparation of 2-{[1(R/S)-Methyl-2-(2',4'-difluorophenyl)-2,3-epoxypropyl]-4-[4-(substituted Phenyl)piperazinyl]phenyl]}-3-(2H,4H)-1,2,4-substituted Thiazolone.

Hexane washed sodium hydride was stirred in DMSO followed by the addition of trimethylsulfoxonium iodide (TMSI) at 15° C. The reaction mixture was stirred at 25–30° C. under nitrogen atmosphere for 1–2 hrs. A solution of the compound obtained in Step 2 in DMSO was added into the above mixture at 25–30° C. and then heated to 80 to 90° C. for 1–2 hrs. Due to the generation of second chiral center in the molecules two pairs of diasteromers were formed which were detected both by TLC as well as by HPLC methods. After the reaction was over the reaction mixture was cooled to 25–30° C., poured into chilled brine and extracted with ethyl acetate. The combined organic layer was washed with water, dried over sodium sulfate and concentrated under vacuum to give either an oil or a fluffy solid which was then used as such for the next step.

Step 4: Preparation of 2-{[1R,2R/1S,2S/1R,2S/1S,2R]2-[(2,4-Difluoro Phenyl)-2-hydroxy-3-methyl-3-(1-H-1,2,4-triazol-1-yl)propyl]}-4-{4-[4-(substituted/unsubstituted Phenyl)-1-piperazinyl]phenyl]}-3-(2H,4H)-1,2,3-substituted Triazol-4-one].

1,2,4-Triazole was stirred with sodium hydride in dimethylformamide (DMF) at 25–30° C. for about 1 hr. The solution of epoxide obtained from step-3 in DMF was then added into this reaction mixture at 25–30° C. and stirred the reaction mixture at 100° C. After the reaction was over the reaction mixture was cooled to 25–30° C., poured into chilled brine and extracted with ethyl acetate. The combined organic layer was washed with water, dried over anhydrous sodium sulfate and concentrated under vacuum to give either an oil or a fluffy solid. Compound so obtained was actually a mixture of four isomers showing two spots on TLC. The mixtures of diastereomers was then separated by preparative HPLC.

EXAMPLE 3

Preparation of 2-[2-(2,4-Difluorophenyl)-2-hydroxy-3-(1H-1,2,4-triazol-1-yl)propyl]-4-{4-[4-(5-chloro-2-methylphenyl)-1-piperazinyl]phenyl}-3-(2H,4H)-1,2,4-triazolone 5-Chloro-2-methyl-phenylpiperazine (20.0 g) was reacted with 4-chloronitrobenzene (16.0 g) in dimethylsulphoxide (DMSO) (110 ml) in the presence of anhydrous potassium carbonate (19.9 g) at a temperature of 135–140° C. for 8 hours. After the reaction was over (TLC monitoring), the reaction mixture was poured into crushed ice and the compound was isolated as an orange solid. After drying under vacuum at 25–30° C. for 6–8 hours, the nitro compound (29.0 g, orange solid; m.p. 146–150° C.) was used as such for the next step.

The nitro compound (18.0 g) was refluxed in ethyl acetate (150 ml) in the presence of stannous chloride dihydrate (55.5 g) for 8 hours. After completion of the reaction, the reaction mixture was poured into 10% aqueous sodium bicarbonate (500 ml) and extracted with ethyl acetate (3×150 ml). The combined organic layer was washed with water (3×100 ml) and then dried over anhydrous sodium sulfate. The organic layer was concentrated under vacuum to give the desired amine (15.3 g, brown oil; yield: 93%).

The amine (15.0 g) was dissolved in a mixture of dichloroethane (DCE) (80 ml) and pyridine (30 ml). The reaction mixture was cooled to about 152° C. A solution of phenylchloroformate (11.67 g) in DCE (10 ml) was added into the solution of amine at such a rate that reaction temperature remained below 20° C. After the addition was over, reaction mixture was stirred at 25–30° C. for about 3 hours. Solvent was evaporated off under reduced pressure to give brownish residue which on triturating with n-hexane (150 ml) gave brown solid. Solid was washed with n-hexane (2×100 ml), 5% aq. solution of sodium bicarbonate (2×100 ml) and distilled water (2×150 ml) followed by drying under vacuum at 40° C. for 5 hours to give 10 gm of corresponding carbamate (Yield 86%) m.p. 201–205° C.

The carbamate (18.0 g) was stirred in 1,4-dioxane (130 ml) followed by the addition of hydrazine hydrate (98%) (5.32 g) at 25–30° C. After refluxing the reaction mixture for 4 hours, solvent was evaporated off to give solid residue which was triturated with 10% methanol in diethyl ether (150 ml). The separated solid was filtered, washed and dried under vacuum at 35° C. for 4 to 6 hours to give corresponding semicarbazide (15.5 g) mp 177–182° C.

The semicarbazide (5.0 g) was stirred in dry DMF (25 ml) followed by the addition of formamidine acetate (6.5 g). After heating at 120° C. for 3 to 5 hours, the reaction mixture was poured into a chilled saturated aq. solution of sodium bicarbonate (100 ml) with stirring. Solid so obtained was filtered, washed with water (3×50 ml) and dried under vacuum at 40° C. for 5 hours to give corresponding triazolone derivative (4.3 g, 84%) as a brown amorphous solid; mp 258–262° C.

Hexane washed sodium hydride (0.057 g, 60% suspension in oil) was added into a stirred suspension of the above triazolone intermediate (0.5 g) in DMF (10 ml) maintained under nitrogen atmophere. After stirring at 25–30° C., a solution of the epoxide interemdiate (0.481 gm) in DMF (5 ml) was added dropwise into the reaction mixture at 40° C. Temperature was then raised to 80° C. and maintained for about 4 hr. Reaction mixture then was cooled to 25–30° C., poured into chilled water (50 ml) and extracted with ethyl acetate (3×100 ml). The combined organic layer was washed with water (4×50 ml), dried over anhydrous sodium sulphate and concentrated under vacuum to give an oily residue (0.3 gm). The oily residue was subjected to column chromatography (silica gel 100–200 mesh) using hexane-ethyl acetate (1:1,300 ml) followed by ethyl acetate (500 ml) to give the required compound. (0.481 gm, 57%) mp 82–91° C.

EXAMPLE 4

2-{[1R2R/1S2S]-2-(2,4-Difluorophenyl)-2-hydroxy-1-methyl-3-(1H-1,2,4-triazol-1-yl)propyl}-4-{4-[4-(5-chloro-2-methylphenyl)-1-piperazinyl]phenyl}-3-(2H,4H)-1,2,4-triazolone (Compound No. 21)

2-{[1R2S/1S2R]-2-(2,4-Difluorophenyl)-2-hydroxy-1-methyl-3-(1H-1,2,4-triazol-1-yl)propyl}-4-{4-[4-(5-chloro-2-methylphenyl)-1-piperazinyl]phenyl}-3-(2H,4H)-1,2,4-triazolone (Compound No. 22)

Step 1: Preparation of 2-{4-[4-[4-(2-Methyl-5-chlorophenyl)piperazinyl]phenyl}-(2H,4H)-1,2,4-triazol-3-one-2-yl}-2(R/S)-methyl-2,4-difluoroacetophenone.

Hexane washed sodium hydride (0.311 g) was added into a stirred solution of triazolone intermediate (4-[4-(2-methyl-5-chlorophenyl)-1-piperazinyl]phenyl-1-(3-(2H,4H)-1,2,4 triazolone (2.5 g) in DMSO (25 ml) maintained under nitrogen atmosphere. After stirring at 25–30° C. for 1 hour, a solution of the intermediate of Formula XIV (2.77 g) in DMSO (5 ml) was added dropwise into the above reaction mixture at 15° C. The reaction mixture was then stirred at 25–30° C. for 2 hours, slowly the temperature was raised to 60° C. and maintained for 3–4 hours. Reaction mixture was cooled to 25–30° C., poured into chilled brine (150 ml) and extracted with ethyl acetate (3×100 ml). The combined organic layer was washed with water (4×50 ml), dried over anhydrous sodium sulphate and concentrated to an oily residue under vacuum. The crude oil was subjected to column chromatography (silica gel 100–200 mesh) using hexane-ethyl acetate (1:1) followed by ethyl acetate to give required compound in pure form (2.6 gm; 71%) mp 125–128° C.

Step 2: Preparation of 2-[1-(R/S)-Methyl-2-(2'-4'-difluorophenyl)-2,3-epoxypropyl]-4-{4-[4-(5-chloro-2-methylphenyl)piperazinyl]phenyl]}-3-(2H,4H)-1,2,4-triazolone.

Hexane washed sodium hydride (0.128 g) was stirred in DMSO (15 ml) followed by the addition of trimethylsulfoxonium iodide (TMSI) (0.736 g) at 15° C. The reaction mixture was stirred at 25–30° C. under nitrogen atmosphere for 1 hr. A solution of Step 1 product (0.9 g) in DMSO (5 ml) was added into the above reaction mixture at 25–30° C. and then heated to 80 to 90° C. for about 1 hr. Due to generation of second chiral centre in the molecule, two pairs of diastereomers were formed which were detected by the TLC and by HPLC analyses. After the reaction was over, the reaction mixture was cooled to 25–30° C., poured into chilled brine and extracted with ethyl acetate (3×75 ml). The combined organic layer was the washed with water (2×50 ml), dried over sodium sulfate and concentrated under vacuum to give an oil (0.93 gm, 100%) which was then used as such immediately for next step.

Step 3: 2-{[1R2R/1S2S]-2-(2,4-Difluorophenyl)-2-hydroxy-1-methyl-3-(1H-1,2,4-triazol-1-yl)propyl}-4-{4-[4-(5-chloro-2-methylphenyl)-1-piperazinyl]phenyl}-3-(2H,4H)-1,2,4-triazolone (Compound No. 21)

2-{[1R2S/1S2R]-2-(2,4-Difluorophenyl)-2-hydroxy-1-methyl-3-(1H-1,2,4-triazol-1-yl)propyl}-4-{4-[4-(5-chloro-2-methylphenyl)-1-piperazinyl]phenyl}-3-(2H,4H)-1,2,4-triazolone (Compound No. 22)

1,2,4-Triazole (0.232 g) was stirred with anhydrous potassium carbonate (0.465 g) in DMF (10 ml) at 25–30° C. for 1–2 hours. A solution of epoxide obtained from Step-2 (0.925 g) in DMF (3.0 ml) was then added into the above mixture at 25–30° C. followed by heating the reaction mixture at 90 to 100° C. for 1 hr. After the reaction was over, reaction mixture was cooled to 25–302° C., poured into chilled brine (70.0 ml) and extracted with ethyl acetate (3×75 ml). The combined organic layer was washed with water (2×250 ml), dried over sodium sulfate and concentrated under vacuum to give an oil. Compound obtained actually was a mixture of two pairs of diastereomers showing two spots on TLC (Ethyl acetate). The mixture of diastereomers (0.613 g, 59%) was then separated by column chromatography to get compound no.21) (faster moving spot on TLC) (35 mg), compound no.22 (slower moving spot on TLC) and 550 mg of mixture of the two spots.

EXAMPLE 5

Preparation of 3-[4-(4-Chlorophenylthioureido)N-methyl-N-phenyl]-2-(2,4-difluorophenyl)-1-(1H-1,2,4-triazolyl)-propan-3-amino-2-ol (Compound No. 89)

Step 1: Preparation of 3-[N-Methyl-N-(4-nitrophenyl)]-2-(2,4-difluorophenyl)-1-(1H-1,2,4-triazolyl)-propan-3-amino-2-ol.

Into a stirred suspension of sodium hydride (42 mg) in dry dimethylformamide (DMF) (5.0 ml) was added N-methyl-p-nitroaniline (1.5 gm) at 5–10° C. The resulting suspension was stirred at 30° C. for 1 hour followed by the addition of a solution of epoxide (Formula IV) in DMF (2.0 ml) at 5–10° C. Reaction mixture was then stirred at 30° C. for 30 min, heated to 60–65° C. for 12 hrs and was cooled to 30° C. Poured the reaction mixture into ice-water mixture and extracted with dichloromethane (3×100 ml). The combined organic layer was washed with DM water (2×70 ml), dried over sodium sulphate and concentrated under reduced pressure to give a yellow solid (2.1 g, m.p. 248–50° C.).

Step 2: Preparation of 3-[N-Methyl-N-(4-aminophenyl)]-2-(2,4-difluorophenyl)-1-(1H-1,2,4-triazolyl)-propane-3-amino-2-ol.

Into a stirred solution of Step 1 product in methanol was added palladium on carbon (10%) (50% w/w) (0.5 g) under nitrogen atmosphere. The suspension was then cooled to 10° C. followed by the addition of ammonium formate (1.2 g) in portions over a period of 15 min. The reaction mixture was then heated to reflux and stirred at reflux for 5 hours. Reaction mixture was cooled to 30° C. and filtered through a celite pad. The combined filtrate was concentrated under vacuum to give a yellow semi-solid which was redissolved in dichloromethane (200 ml). The organic layer was washed with DM water (3×100 ml), dried over sodium sulfate and concentrated under reduced pressure to give semi-solid amine which was subjected to next step without further purification.

Step 3: Preparation of 3-[4-(4-Chlorophenylthioureido)N-methyl-N-phenyl]-2-(2,4-difluorophenyl)-1-(1H-1,2,4-triazolyl)-propan-3-amino-2-ol (Compound No. 89)

Dissolved the amine (Step-II product) (400 mg) in anhydrous acetonitrile (5 ml) and added p-chlorophenyl isothiocyanate (227 mg, 1.2 eqm) to it. Stirred for 4 hours at 25–30° C. and the solvent was evaporated off to afford residue which was purified using column chromatography (Yield: 200 mg, 34%).

EXAMPLE 6

Preparation of 3-{4-[4-N-(4-Chlorophenyl)-N-(methylureido)-piperazinyl]-phenoxy}-2-(2,4-difluorophenyl)-1-(1H-1,2,4-triazolyl)-2-methoxypropane (Compound No. 75)

Dissolved the amine of Formula VII (prepared by following the process as described in U.S. Pat. No. 5,023,258) (9 g) in anhydrous acetonitrile (50 ml) and added p-chlorophenyl isocyanate (4 g) to it. Stirred the reaction mixture for 1 hr at 25–30° C. and evaporated the solvent to afford crude oil which was purified using column chromatography (Yield: 8.3 g, 75%).

EXAMPLE 7

Preparation of [1R2R/1S2S]1-{4-[4-(4-Chlorophenylureido)-piperazinyl]-phenoxy}-2-(2,4-difluorophenyl)-1-methyl -3-(1H-1,2,4-triazolyl)-propan-2-ol (Compound No. 77) and [1R2S/1S2R] 1-{4-[4-(4-Chlorophenylureido)-piperazinyl]-phenoxy}-2-(2,4-difluorophenyl)-1-methyl-3-(1H-1, 2,4-triazolyl)-propan-2-ol (Compound No. 78)

Step 1: Preparation of 2-{4-[4-Acetyl-1-piperazinyl]-phenyl]-2(R/S)-methyl-2,4-difluoroacetophenone A solution of 2-chloro-2(R/S)-methyl-2,4-difluoroacetophenone(10.5 g) (1.5 molar equivalent) in dry dimethylformamide (DMF) was added into a stirred suspension of 1-acetyl-4-hydroxyphenylpiperazine (8.0 g) and potassium carbonate (12.16 g) in dimethylformamide (DMF) at 5–100° C. Reaction mixture was then stirred at 30° C. for 20 min, heated to 60° C. and stirred at 60° C. for about 5 hrs. Reaction mixture then was cooled to 25–30° C., poured into ice-water mixture and extracted with ethyl acetate (3×200 ml). The combined organic layer was washed with water (3×100 ml), dried over sodium sulfate and concentrated under reduced pressure to get foamy product (8.0 g; 71%).

Step 2: Preparation of 1-(R/S)-Methyl-2,3-epoxypropyl-2-{4-[(4-acetylpiperazinyl)]phenoxy}-2-(2',4'-difluorobenzene)

Into a stirred suspension of sodium hydride (1.97 g) in dry dimethylsulphoxide (DMSO) under nitrogen atmosphere was added trimethylsulfoxomium iodide (9.075 g) at 10–15° C. The foaming suspension was stirred at 30° C. for 1 hr followed by the addition of a solution of Step-I product (8.0 g) in DMSO at 10–15° C. over a period of 10 min. Reaction mixture was then heated to 90° C. and stirred at 90° C. for about 4 hours. Cooled the reaction mixture, poured it into ice-water mixture and extracted with ethyl acetate (3×200 ml). The combined organic layer was then washed with water (3×150 ml), dried over sodium sulphate and concentrated under reduced pressure to give foamy product (7.0 g; 85%).

Step 3: Preparation of 1-{4-[4-Acetylpiperazinyl)-phenyl]-2-(2,4-difluorophenyl)-1(R/S)-methyl-3-(1H-1,2,4-triazolyl)-propane-2-ol)]

Into a stirred suspension of sodium hydride(1.67 g) in dry dimethylformamide (DMF), was added 1,2,4-triazole (2.4 g) under nitrogen atmosphere and stirred at 30° C. for 1 hour. A solution of Step 2 product (7.0 g) in DMF was then added into the above suspension at 30° C. followed by heating to 80–850° C. and stirred at 80–85° C. for 8 hrs. Reaction mixture was then cooled to 30° C., poured into ice-water mixture and the suspension was extracted with ethyl acetate (3×200 ml). The combined organic extract was washed with DM water (3×150 ml), dried over sodium sulfate and concentrated under reduced pressure to give semisolid compound (6.0 g, 73%).

Step 4: Preparation of 1-[4-(4-(Piperazinyl)phenoxy]-2-(2, 4-difluorophenyl)-1(R/S)-methyl-3-(1H-1,2,4-triazolyl)-propan-2-ol Step 3 product (6.0 g) was dissolved in 1,4-dioxane (50 ml) followed by the addition of a solution of sodium hydroxide (1.0 g) in water (50 ml). Heated the reaction mixture to reflux, stirred it at reflux for about 5 hrs and concentrated under reduced pressure to give a brown semi-solid residue. This brown semi solid was redissolved in ethyl acetate (200 ml), washed with DM water (2×100 ml), dried over sodium sulphate and concentrated to get a pure brown semi-solid (4.5 g; 81%).

Step 5: Preparation of [1R2R/1S2S)1-{4-[4-(4-Chlorophenylureido)-piperaziny]-phenoxy}-2-(2,4-difluorophenyl)-1-methyl-3-(1H-1,2,4-triazolyl)-propan-2-ol. (Compound No. 77) and

[1R2R/1S2S]-1-{4-[4-(4-Chlorophenylureido)-piperazinyl]-phenoxy}-2-(2,4-difluorophenyl)-1-methyl-3-(1H-1,2,4-triazolyl)propane-2-ol. (Compound No. 78).

Dissolved the amine obtained as Step 4 product (Formula VII) (800 mg) in anhydrous acetonitrile (5 ml) followed by the addition of p-chlorophenyl isocyanate (3.44 mg). The reaction mixture so obtained was stirred for 1 hour at room temperature and after the reaction was over, the solvent was evaporated off to give brown semi solid residue which was purified using column chromatography. The two spots observed on TLC were separated by preparative HPLC (Upper spot, 50 mg, 30%, compound No. 77; Lower spot, 25 mg, 20%, Compound No. 78)

EXAMPLE 8

Preparation of 2-[2-(2,4-Difluorophenyl)-2-hydroxy-3-(1H-1,2,4-triazol-1-yl)propyl]-4-{4-[4-(4-chlorophenyluredio)-1-piperazinyl]phenyl}-3-(2H, 4H)-1,2,4-triazolone (Compound No. 91)

Dissolved the starting amine of Formula VII (following the method as described in U.S. Pat. No. 5,371,101) in anhydrous acetonitrile and added p-chlorophenyl isocyanate (1.2 moler equivalent) to it and stirred for 1 hr at 25–30° C. After completion of the reaction, the solvent was evaporated off to obtain a crude product which was purified using column chromatography.

Assignment of RR/SS was done on the basis of $^1$HNMR analysis.

An illustrative list of some of the compounds of the invention which were synthesized by one or more of the above described methods is given below along with their $^1$HNMR data. All $^1$HNMR spectra were recorded on Brucker AMX 300 NMR machines (300 MHZ) using $CDCl_3$ as a solvent and TMS as an internal standard unless otherwise specified. All values are given in ppm.

Symbols in the examples have the following meanings. Thus, s singlet; d:doublet; t:triplet; q:quartet; dd: double doublet; m:multiplet; br:broad; J: coupling constant:

Compound No. 1:
2-{[1R2R/1S2S]-2-(2,4-Difluorophenyl)-2-hydroxy-1-methyl-3-(1H-1,2,4-triazol-1-yl)propyl}-4-{4-[4-(4-chlorophenyl)-1-piperazinyl]phenyl}-3-(2H,4H)-1,2,4-triazolone NMR($CDCl_3$):-δ 7.96 (s, 1H; Ar—H), 7.72–7.67 (d, 2H; J=14.7 Hz; Ar—H), 7.60–7.52 (q, 1H; Ar—H), 7.45–7.42 (d, 2H; J=9.0 Hz; Ar—H), 7.26–7.23 (d, 2H; J=9.0 Hz; Ar—H), 7.06–7.03 (d, 2H; J=9.0 Hz; Ar—H), 6.91–6.88 (d, 2H; J=9.0 Hz; Ar—H), 6.83–6.77 (m, 2H; Ar—H), 5.56 (s, 1H; OH, $D_2O$ ex.), 5.12–5.05 (q, 1H; —CH.$CH_3$), 5.03–4.98 (d, 1H; J=15.0 Hz; triazole-$CH_2$), 4.38–4.33 (d, 1H; J=15.0 Hz; triazole-$CH_2$), 3.39–3.37 (d, 8H; piperazine-$CH_2$—) & 1.31–1.28 (d, 3H; J=7.2 Hz; —CH.$CH_3$)ppm.

Compound No. 2:
2-{[1R2S/1S2R]-2-(2,4-Difluorophenyl)-2-hydroxy-1-methyl-3-(1H-1,2,4-triazol-1-yl)propyl}-4-{4-[4-(4- chlorophenyl)-1-piperazinyl]phenyl}-3-(2H,4H)-1,2,4-triazolone NMR(CDCl$_3$):-δ 8.09 (s, 1H; Ar—H), 7.68 (s, 1H; Ar—H), 7.39 (s, 1H; Ar—H), 7.36–7.30 (m, 1H; Ar—H), 7.26–7.22 (m, 3H; Ar—H), 7.16–7.13 (d, 2H; J=9.0 Hz; Ar—H), 6.97–6.94 (d, 2H; J=9.0 Hz; Ar—H), 6.89–6.87 (d, 2H; J=9.0 Hz; Ar—H), 6.77–6.63 (m, 2H; Ar—H),6.04 (s, 1H; Ar—H), 5.29 (s, 1H; OH, D$_2$O ex.), 5.11–5.04 (q, 1H; —CH.CH$_3$), 4.92–4.88 (d, 1H; J=15.0 Hz; triazole-CH$_2$), 4.63–4.59 (d, 1H; J=15.0 Hz; triazole-CH$_2$), 3.34–3.28 (q, 8H; piperazine-CH$_2$—) & 1.64–1.61 (d, 3H; J=7.2 Hz; —CH.CH$_3$)ppm.

Compound No. 3:

2-{[1R2R/1S2S]-2-(2,4-Difluorophenyl)-2-hydroxy-1-methyl-3 (1H-1,2,4triazol-1-yl)propyl}-4-{4-[4-(2,4-dinitrophenyl)-1-piperazinyl]phenyl}-3-(2H,4H)-1,2,4-triazolone NMR(CDCl$_3$):-δ 8.81–8.80 (d, 1H; Ar—H), 8.40–8.36 (dd, 1H; Ar—H),8.03 (s, 1H; Ar—H), 7.79–7.75 (d, 2H; Ar—H), 7.65–7.62 (q, 1H; Ar—H), 7.54–7.51 (d, 2H; Ar—H), 7.25–7.22 (d, 1H; Ar—H), 7.09–7.07 (d, 2H; J=9.0 Hz; Ar—H), 6.91–6.85 (m, 2H; Ar—H), 5.60 (s, 1H; OH, D$_2$O ex.), 5.17–5.05 (qd, 2H; —CH.CH$_3$ & triazole-CH$_2$), 4.46–4.41 (d, 1H; J=15.0 Hz; triazole-CH$_2$), 3.54–3.53 (d, 8H; piperazine-CH$_2$—) & 1.37–1.35 (d, 3H; J=7.2 Hz; —CH.CH$_3$)ppm.

Compound No. 4:

2-{[1R2S/1S2R]-2-(2,4-Difluorophenyl)-2-hydroxy-1-methyl-3-(1H-1,2,4-triazol-1-yl)propyl}-4-{4-[4-(2,4-dinitrophenyl)-1-piperazinyl]phenyl}-3-(2H,4H)-1,2,4-triazolone NMR(CDCl$_3$):-δ 8.73–8.72 (d, 1H; Ar—H), 8.32–8.28 (dd, 1H; Ar—H), 8.08 (s, 1H; Ar—H), 7.68 (s, 1H; Ar—H), 7.41 (s, 1H; Ar—H), 7.35–7.32 (m, 1H; Ar—H), 7.18–7.13 (m, 3H; Ar—H), 6.76–6.74 (d, 2H; J=9.0 Hz; Ar—H), 6.73–6.63 (m, 2H; Ar—H), 5.99 (s, 1H; OH, D$_2$O ex.), 5.09–5.07 (q, 1H; —CH.CH$_3$), 4.93–4.88 (d, 1H; J=15.0 Hz; triazole-CH$_2$), 4.64–4.59 (d, 1H; J=15.0 Hz; triazole-CH$_2$), 3.46–3.39 (q, 8H; piperazine-CH$_2$—) & 1.64–1.61 (d, 3H; J=7.2 Hz; —CH.CH$_3$)ppm.

Compound No. 5:

2-{[1R2R/1S2S]-2-(2,4-Difluorophenyl)-2-hydroxy-1-methyl-3-(1H-1,2,4-triazol-1-yl)propyl}-4-[4-(1-phenylpiperazinyl)phenyl]-3-(2H,4H)-1,2,4-triazolone NMR(CDCl$_3$):-δ 7.96 (s, 1H; Ar—H), 7.72–7.67 (d, 2H; J=13.5 Hz; Ar—H), 7.60–7.52 (q, 1H; Ar—H), 7.44–7.41 (d, 2H; J=9.0 Hz; Ar—H), 7.33–7.26 (m, 3H; Ar—H), 7.07–6.97 (m, 4H; Ar—H), 6.93–6.88 (m, 1H; Ar—H), 6.84–6.77 (m, 2H; Ar—H), 5.56 (s, 1H; OH, D$_2$O ex.), 5.12–4.98 (qd, 2H; —CH.CH$_3$triazole-CH$_2$), 4.38–4.33 (d, 1H; J=15.0 Hz; triazole-CH$_2$), 3.38–3.37 (d, 8H; piperazine-CH$_2$—) & 1.30–1.28 (d, 3H; J=6.9 Hz; —CH.CH$_3$)ppm.

Compound No. 6:

2-{[1R2S/1S2R]-2-(2,4-Difluorophenyl)-2-hydroxy-1-methyl-3-(1H-1,2,4-triazol-1-yl)propyl}-4-[4-(1-phenylpiperazinyl)phenyl]-3-(2H,4H)-1,2,4-triazolone NMR(CDCl$_3$):-δ 8.09 (s, 1H; Ar—H), 7.68 (s, 1H; Ar—H), 7.39 (s, 1H; Ar—H), 7.36–7.26 (m, 3H; Ar—H), 7.15–7.12 (d, 2H; J=9.0 Hz; Ar—H), 6.97–6.87 (m, 5H; Ar—H), 6.77–6.64 (m, 2H; Ar—H), 6.05 (s, 1H; OH, D$_2$O ex.), 5.09–5.07 (q, 2H; —CH.CH$_3$triazole-CH$_2$), 4.91–4.87 (d, 1H; J=15.0 Hz; triazole-CH$_2$), 4.63–4.58 (d, 1H; J=15.0 Hz; triazole-CH$_2$), 3.34 (s, 8H; piperazine-CH$_2$—) & 1.63–1.61 (d, 3H; J=6.9 Hz; —CH.CH$_3$) ppm.

Compound No. 7:

2-{[1R2R/1S2S]-2-(2,4-Difluorophenyl)-2-hydroxy-1-methyl-3-(1H-1,2,4-triazol-1-yl)propyl}-4-{4-[4-(3,4-dichlorophenyl)-1-piperzinyl]phenyl}-3-(2H,4H)-1,2,4-triazolone NMR(CDCl$_3$):-δ 7.96 (s, 1H; Ar—H), 7.71–7.67 (d, 2H; J=13.5 Hz; Ar—H), 7.61–7.52 (q, 1H; Ar—H), 7.45–7.42 (d, 2H; J=9.0 Hz; Ar—H), 7.33–7.30 (d, 1H; J=8.7 Hz; Ar—H), 7.06–7.01 (m, 3H; Ar—H), 6.84–6.77 (m, 3H; Ar—H), 5.56 (s, 1H; OH, D$_2$O ex.), 5.12–5.05 (q, 1H; —CH.CH$_3$), 5.03–4.98 (d, 1H; J=15.0 Hz; triazole-CH$_2$), 4.38–4.34 (d, 1H; J=15.0 Hz; triazole-CH$_2$), 3.39–3.37 (d, 8H; piperazine-CH$_2$—) & 1.30–1.28 (d, 3H; J=7.2 Hz; —CH.CH$_3$)ppm.

Compound No. 8:

2-{[1R2S/1S2R]-2-(2,4-Difluorophenyl)-2-hydroxy-1-methyl-3-(1H-1,2,4-triazol-1-yl)propyl}-4-{4-[4-(3,4-dichlorophenyl)-1-piperazinyl]phenyl}-3-(2H,4H)-1,2,4-triazolone NMR(CDCl$_3$):-δ 8.08 (s, 1H; Ar—H), 7.67 (s, 1H; Ar—H), 7.39–7.25 (m, 3H; Ar—H), 7.15–7.12 (d, 2H; J=9.0 Hz; Ar—H), 6.99–6.93 (m, 3H; Ar—H), 6.79–6.65 (m, 3H; Ar—H), 6.01 (s, 1H; OH, D$_2$O ex.), 5.10–5.05 (q, 1H; —CH.CH$_3$), 4.91–4.87 (d, 1H; J=15.0 Hz; triazole-CH$_2$), 4.62–4.58 (d, 1H; J=15.0 Hz; triazole-CH$_2$), 3.31 (s, 8H; piperazine-CH$_2$—) & 1.63–1.60 (d, 3H; J=7.2 Hz; —CH.CH$_3$)ppm.

Compound No. 9:

2-{[1R2R/1S2S]-2-(2,4-Difluorophenyl)-2-hydroxy-1-methyl-3-(1H-1,2,4-triazol-1-yl)propyl}-4-{4-[4-(3-trifluoromethylphenyl)-1-piperazinyl]phenyl}-3-(2H,4H)-1,2,4-triazolone NMR(CDCl$_3$):- . . . 7.99 (s, 1H; Ar—H), 7.74–7.70 (d, 2H; J=14.7 Hz; Ar—H), 7.62–7.54 (q, 1H; Ar—H), 7.48–7.39 (m, 3H; Ar—H), 7.19–7.07 (m, 5H; Ar—H), 6.85–6.79 (m, 2H; Ar—H), 5.59 (s, 1H; OH, D$_2$O ex.), 5.15–5.01 (qd, 1H; —CH.CH$_3$ & triazole-CH$_2$), 4.40–4.35 (d, 1H; J=15.0 Hz; triazole-CH$_2$), 3.43 (s, 8H; piperazine-CH$_2$—) & 1.32–1.30 (d, 3H; J=7.2 Hz; —CH.CH$_3$)ppm.

Compound No. 10:

2-{[1R2S/1S2R]-2-(2,4-Difluorophenyl)-2-hydroxy-1-methyl-3-(1H-1,2,4-triazol-1-yl)propyl}-4-{4-[4-(3-trifluoromethylphenyl)-1-piperazinyl]phenyl}-3-(2H,4H)-1,2,4-trazolone NMR(CDCl$_3$):-δ 8.12 (s, 1H; Ar—H), 7.71 (s, 1H; Ar—H), 7.43–7.32 (m, 3H; Ar—H), 7.15–7.11 (m, 5H; Ar—H), 7.00–6.97 (d, 2H; Ar—H), 6.78–6.66 (m, 2H; Ar—H), 6.06 (s, 1H; OH, D$_2$O ex.), 5.13–5.07 (q, 1H; —CH.CH$_3$), 4.95–4.90 (d, 1H; J=15.0 Hz; triazole-CH$_2$), 4.65–4.61 (d, 1H; J=15.0 Hz; triazole-CH$_2$), 3.39 (s, 8H; piperazine-CH$_2$—) & 1.66–1.64 (d, 3H; J=9.6 Hz; —CH.CH$_3$)ppm.

Compound No. 11:

2-{[1R2R/1S2S]-2-(2,4-Difluorophenyl)-2-hydroxy-1-methyl-3-(1H-1,2,4-triazol-1-yl)propyl}-4-{4-[4-(4-fluorophenyl)-1-piperazinyl]phenyl}-3-(2H,4H)-1,2,4-triazolone NMR(CDCl$_3$):-. 7.96.09 (s, 1H; Ar—H), 7.72 (s, 1H; Ar—H), 7.67 (s, 1H; Ar—H), 7.55–7.57 (m, 1H; Ar—H), 7.41–7.44 (d, 2H; Ar—H), 6.77–7.07 (m, 8H; Ar—H), 5.57 (S, 1H; OH, D$_2$O ex.), 5.10–5.17 (q, 1H; J=7 Hz; —CH), 4.98–5.03 (d, 1H; J=14.7 Hz, —CH), 4.33–4.37 (d, 1H; J=14.7 Hz; triazole-CH$_2$), 3.38–3.40 (m, 4H; 2×—CH$_2$), 3.25–3.29 (m, 4H; 2×CH$_2$—) & 1.28 (d, J=7 Hz; 3H; CH$_3$)ppm.

Compound No. 12:

2-{[1R2S/1S2R]-2-(2,4-Difluorophenyl)-2-hydroxy-1-methyl-3-(1H-1,2,4-triazol-1-yl)propyl}-4-{4-[4-(4-fluorophenyl)-1-piperazinyl]phenyl}-3-(2H,4H)-1,2,4-triazolone NMR(CDCl$_3$):-δ 8.09 (s, 1H; Ar—H), 7.68 (s, 1H; Ar—H), 6.60–7.40 (m, 12H; Ar—H), 6.02 (S, 1H; OH, D$_2$O ex.), 5.04–5.11 (q, 1H; J=7 Hz; —CH), 4.87–4.92 (d, 1H; J=14.7 Hz, —CH), 4.58–4.63 (d, 1H; J=14.7 Hz; triazole-CH$_2$), 3.33–3.44 (m, 4H; 2×—CH$_2$), 3.23–3.25 (m, 4H; 2×CH$_2$—) & 1.28 (d, J=7 Hz; 3H; CH$_3$)ppm.

Compound No. 13:

2-{[1R2R/1S2S]-2-(2,4-Difluorophenyl)-2-hydroxy-1-methyl-3-(1H-1,2,4-triazol-1-yl)propyl}-4-{4-[4-(4- methoxyphenyl)-1-piperazinyl]phenyl}-3-(2H,4H)-1,2,4-triazolone NMR(CDCl$_3$):-δ 7.97 (s, 1H; Ar—H), 7.74 (s, 1H; Ar—H), 7.67 (s, 1H; Ar—H), 7.60–7.51 (m, 1H; Ar—H), 7.44–7.41 (d, 2H; Ar—H), 7.28 (s, 1H; Ar—H), 7.07–7.04 (d, 2H; Ar—H), 6.98–6.95 (m, 2H; Ar—H), 6.89–6.86 (m, 2H; Ar—H), 6.82–6.77 (m, 2H; Ar—H), 5.59 (S, 1H; OH, D$_2$O ex.), 5.10–4.99 (q, 1H; J=7 Hz; —CH), 4.37–4.33 (d, 1H; J=14.7 Hz, —CH), 3.79 (s, 3H; OCH3), 3.41–3.38 (t, 4H; 2×—CH$_2$), 3.25–3.22 (t, 4H; 2×CH$_2$—) & 1.30–1.25 (d, J=7 Hz; 3H; CH$_3$)ppm.

Compound No. 15:
2-{[1R2R/1S2S]-2-(2,4-Difluorophenyl)-2-hydroxy-1-methyl-3-(1H-1,2,4-triazol-1-yl)propyl}-4-{4-[4-(3-chloro-4-fluorophenyl)-1-piperazinyl]phenyl}-3-(2H,4H)-1,2,4-triazolone NMR(CDCl$_3$):- . . . (s, 1H; Ar—H), 7.73–7.69 (d, 2H; Ar—H), 7.62–7.53 (m, 1H; Ar—H), 7.46–7.43 (d, 2H; Ar—H), 7.10–7.05 (t, 3H; Ar—H), 7.00–6.98 (m, 1H; Ar—H), 6.85–6.79 (m, 3H; Ar—H), 5.57 (s, 1H; OH, D$_2$O ex.), 5.14–5.00 (m, 2H; J=7 Hz; —CH), 4.39–4.35 (d, 1H; J=14.7 Hz, —CH), 3.40–3.38 (d, 4H; 2×—CH$_2$), 3.30–3.29 (d, 4H; 2×CH$_2$—) & 1.32–1.30 (d, J=7 Hz; 3H; CH$_3$)ppm.

Compound No. 16:
2-{[1R2S/1S2R]-2-(2,4-Difluorophenyl)-2-hydroxy-1-methyl-3-(1H-1,2,4-triazol-1-yl)propyl}-4-{4-[4-(3-chloro-4-fluorophenyl)-1-piperazinyl]phenyl}-3-(2H,4H)-1,2,4-triazolone NMR(CDCl$_3$):-δ 8.02 (s, 1H; Ar—H), 7.61 (s, 1H; Ar—H), 7.37 (s, 1H; Ar—H), 7.33–7.23 (m, 1H; Ar—H), 7.09–7.06 (d, 2H; Ar—H), 6.98–6.956 (t, 1H; Ar—H), 6.90–6.87 (d, 3H; Ar—H), 6.76–6.57 (m, 3H; Ar—H), 5.96 (s, 1H; OH, D$_2$O ex.), 5.05–4.98 (q, 1H; J=7 Hz; —CH—CH$_3$), 4.87–4.81 (d, 1H; J=14.7 Hz, —CH), 4.57–4.52 (d, 1H; J=7 Hz, —CH), 3.27–3.25 (t, 4H; 2×—CH$_2$), 3.19–3.18 (t, 4H; 2×CH$_2$—) & 1.57–1.55 (d, J=7 Hz; 3H; CH$_3$)

Compound No. 17:
2-{[1R2R/1S2S]-2-(2,4-Difluorophenyl)-2-hydroxy-1-methyl-3-(1H-1,2,4-triazol-1-yl)propyl}-4-{4-[4-(3-chloro-4-methylphenyl)-1-piperazinyl]phenyl}-3-(2H,4H)-1,2,4-triazolone NMR(CDCl$_3$):-. 7.98 (s, 1H; Ar—H), 7.74–7.69 (d, 2H; Ar—H), 7.62–7.53 (q, 1H; Ar—H), 7.46–7.43 (d, 2H; Ar—H), 7.16–7.13 (d, 1H; Ar—H), 7.08–7.05 (d, 2H; Ar—H), 6.98–7.97 (m, 1H; Ar—H), 6.86–7.98 (m, 3H; Ar—H), 5.59 (s, 1H; OH, D$_2$O ex.), 5.14–5.00 (m, 2H; J=7 Hz; —CH), 4.39–4.35 (d, 1H; J=14.7 Hz, —CH), 3.40–3.38 (d, 4H; 2×—CH$_2$), 3.33–3.32 (d, 4H; 2×CH$_2$—), 2.31 (s, 3H; Ar-CH$_3$) & 1.32–1.29 (d, J=7 Hz; 3H; CH$_3$)ppm.

Compound No. 19:
2-{[1R2R/1S2S]-2-(2,4-Difluorophenyl)-2-hydroxy-1-methyl-3-(1H-1,2,4-triazol-1-yl)propyl}-4-{4-[4-(2,4-dimethylphenyl)-1-piperazinyl]phenyl}-3-(2H,4H)-1,2,4-triazolone NMR(CDCl$_3$):-δ 7.48 (s, 1H; Ar—H), 7.74 (s, 1H; Ar—H), 7.69 (s, 1H; Ar—H), 7.53–7.61 (m, 1H; Ar—H), 7.42–7.45 (m, 2H; Ar—H), 6.47–7.08 (m, 5H; Ar—H), 6.78–6.85 (m, 2H, Ar—H), 5.60 (s, 1H; OH, D$_2$O ex.), 5.07–5.14 (q, 1H; J=7 Hz; —CH), 5.00–5.05 (d, 1H; J=14 Hz, —CH), 4.34–4.39 (d, 1H; J=14 Hz; triazole-CH$_2$), 3.37–3.40 (m, 4H; 2×—CH$_2$), 3.05–3.09 (m, 4H; 2×CH$_2$—), 2.33 (s, 3H, CH$_3$), 2.30 (s, 3H; CH$_3$) & 1.29–1.32 (d, J=7 Hz; 3H; CH$_3$)ppm.

Compound No. 20:
2-{[1R2S/1S2R]-2-(2,4-Difluorophenyl)-2-hydroxy-1-methyl-3-(1H-1,2,4-triazol-1-yl)propyl}-4-{4-[4-(2,4-dimethylphenyl)-1-piperazinyl]phenyl}-3-(2H,4H)-1,2,4-triazolone NMR(CDCl$_3$):-δ 8.08 (s, 1H; Ar—H), 7.67 (s, 1H; Ar—H), 7.31–7.39 (m, 2H; Ar—H), 6.94–7.14 (m, 7H; Ar—H), 6.63–6.76 (m, 2H; Ar—H), 6.06 (s, 1H; OH, D$_2$O ex.), 5.04–5.11 (q, 1H; J=7 Hz; —CH), 4.87–4.92 (d, 1H; J=15 Hz, —CH), 4.58–4.63 (d, 1H; J=15 Hz; triazole-CH$_2$), 3.31–3.34 (m, 4H; 2×—CH$_2$), 3.02–3.03 (m, 4H; 2×CH$_2$—), 2.29 (s, 3H, —CH$_3$), 2.28 (s, 3H; CH$_3$) & 1.61–1.63 (d, J=7 Hz; 3H; CH$_3$)ppm.

Compound No. 21:
2-{[1R2R/1S2S]-2-(2,4-Difluorophenyl)-2-hydroxy-1-methyl-3-(1H-1,2,4-triazol-1-yl)propyl}-4-{4-[4-(5-chloro-2-methylphenyl)-1-piperazinyl]phenyl}-3-(2H,4H)-1,2,4-triazolone NMR(CDCl$_3$):-δ 8.03 (s, 1H; Ar—H), 7.78–7.73 (d, 2H; Ar—H), 7.62–7.60 (q, 1H; Ar—H), 7.50–7.47 (d, 2H; Ar—H), 7.19–7.03 (m, 5H; Ar—H), 6.89–6.82 (m, 2H; Ar—H), 5.58 (s, 1H; OH, D$_2$O ex.), 5.16–5.04 (m, 2H; J=7 Hz; —CH), 4.43–4.39 (d, 1H; J=14.7 Hz, —CH), 3.45–3.41 (d, 4H; 2x-CH$_2$), 3.13–3.10 (d, 4H; 2×CH$_2$—), 2.35 (s, 3H; Ar—CH$_3$) & 1.36–1.33 (d, J=7 Hz; 3H; CH$_3$)ppm.

Compound No. 22:
2-{[1R2S/1S2R]-2-(2,4-Difluorophenyl)-2-hydroxy-1-methyl-3-(1H-1,2,4-triazol-1-yl)propyl}-4-{4-[4-(5-chloro-2-methylphenyl)-1-piperazinyl]phenyl}-3-(2H,4H)-1,2,4-triazolone NMR(CDCl$_3$):-δ 8.15 (s, 1H; Ar—H), 7.74 (s, 1H; Ar—H), 7.46–7.39 (m, 1H; Ar—H), 7.31 (s, 1H; Ar—H), 7.21–7.15 (t, 3H; Ar—H), 7.05–6.99 (m, 4H; Ar—H), 6.79–7.72 (m, 2H; Ar—H), 6.12 (s, 1H; OH, D$_2$O ex.), 5.15–5.13 (q, 1H; J=7 Hz; —CH—CH$_3$), 4.98–4.93 (d, 1H; J=14.7 Hz, —CH), 4.69–4.64 (d, 1H; J=14.7 Hz, —CH), 3.40–3.37 (t, 4H; 2×—CH$_2$), 3.10–3.07 (d, 4H; 2×CH$_2$—), 2.33 (s, 3H; Ar—CH$_3$) & 1.69–1.67 (d, J=7 Hz; 3H; CH$_3$)ppm.

Compound No. 35:
2-[2-(2,4-Difluorophenyl)-2-hydroxy-3-(1H-1,2,4-triazol-1-yl)propyl]-4-{4-[4-(2-methoxyphenyl)-1-piperazinyl]phenyl}-3-(2H,4H)-5-methyl-1,2,4-triazolone NMR(CDCl$_3$):-δ 8.16 (s, 1H; Ar—H), 7.81 (s, 1H; Ar—H), 7.60–7.57 (m, 1H; Ar—H), 7.02–6.79 (m, 9H; Ar—H), 6.10 (s, 1H; OH; D$_2$O ex.), 4.70 (s, 2H; triazolone-CH$_2$), 4.55–4.50 (d, 1H; J=14.7 Hz; triazole-CH$_2$), 4.18–4.13 (d, 1H; J=15.0 Hz; triazole-CH$_2$), 3.89 (s, 3H; o-OCH$_3$—), 3.41 (s, 4H; piperazine-CH$_2$—), 3.21 (s, 4H; piperazine-CH$_2$—) & 2.04 (s, 3H; triazolone-CH$_3$)ppm.

Compound No. 36:
2-[2-(2,4-Difluorophenyl)-2-hydroxy-3-(1H-1,2,4-triazol-1-yl)propyl]-4-{4-[4-(4-fluorophenyl)-1-piperazinyl]phenyl}-3-(2H,4H)-5-methyl-1,2,4-triazolone NMR(CDCl$_3$-DMSO-d$_6$):-δ 8.19 (s, 1H; Ar—H), 7.77 (s, 1H; Ar—H), 7.60–7.52 (m, 1H; Ar—H), 7.42 (s, 1H; Ar—H), 7.32–7.30 (d, 1H; J=8.7 Hz; Ar—H), 7.08–7.29 (m, 9H; Ar—H), 6.86–6.79 (m, 2H; Ar—H), 6.09 (s, 1H; OH, D$_2$O ex.), 4.72 (s, 2H; triazolone-CH$_2$), 4.50–4.60 (d, 1H; J=14.7 Hz; triazole-CH$_2$), 4.19–4.15 (d, 1H; J=14.7 Hz; triazole-CH$_2$), 3.39–3.33 (br, 4H; piperazine-CH$_2$—), 3.26 (s, 4H; piperazine-CH$_2$—) & 2.04 (s, 3H; triazolne-CH$_3$) ppm.

Compound No. 37:
2-[2-(2,4-Difluorophenyl)-2-hydroxy-3-(1H-1,2,4-triazol-1-yl)propyl]-4-{4-[4-(3,4-dichlorophenyl)-1-piperazinyl]phenyl}-3-(2H,4H)-1,2,4-triazolone NMR (CDCl$_3$):-δ 8.16 (s, 1H; Ar—H), 7.83 (s, 1H; Ar—H), 7.59–7.56 (m, 1H; Ar—H), 7.49 (s, 1H; Ar—H), 7.32–7.26 (m, 4H; Ar—H), 6.99–6.97 (d, 3H; Ar—H), 6.85–6.76 (m, 3H; Ar—H), 4.70 (s, 2H; triazolone-CH$_2$), 4.63–4.58 (d, 1H; J=14.7 Hz; triazole-CH$_2$), 4.21–4.16 (d, 1H; J=14.7 Hz; triazole-CH$_2$), & 3.33 (s, 8H; piperazine-CH$_2$—)ppm.

Compound No. 38:
2-[2-(2,4-Difluorophenyl)-2-hydroxy-3-(1H-1,2,4-triazol-1-yl)propyl]-4-{4-[4-(2,4-diaminophenyl)-1-piperazinyl]phenyl}-3-(2H,4H)-1,2,4-triazolone NMR (CDCl$_3$):-δ 8.19 (s, 1H; Ar—H), 7.85 (s, 1H; Ar—H), 7.63–7.55 (m, 1H; Ar—H), 7.51 (s, 1H; Ar—H), 7.28–7.25 (d, 3H; Ar—H), 7.01–6.98 (d, 2H; Ar—H), 6.89–6.80 (m, 3H; Ar—H), 6.15–6.10 (m,br, 2H; Ar—H), 4.72 (s, 2H; triazolone-CH$_2$), 4.65–4.60 (d, 1H; J=15.0 Hz; triazole-CH$_2$), 4.23–4.18 (d, 1H; J=15.0 Hz; triazole-CH$_2$), 3.34 (s, br, 4H; piperazine-CH$_2$—), & 3.02–3.00 (d, 4H; piperazine-CH$_2$—)ppm.

Compound No. 39:

2-[2-(2,4-Difluorophenyl)-2-hydroxy-3-(1H-1,2,4-triazol-1-yl)propyl]-4-{4-[4-(4-methylphenyl)-1-piperazinyl]phenyl}-3-(2H,4H)-1,2,4-triazolone NMR (CDCl$_3$):-δ 8.18 (s, 1H; Ar—H), 7.85 (s, 1H; Ar—H), 7.64–7.55 (q, 1H; Ar—H), 7.5 (s, 1H; Ar—H), 7.29–7.27 (t, 3H; Ar—H), 7.14–7.11 (d, 2H; Ar—H), 7.03–6.99 (d, 2H; Ar—H), 6.93–6.80 (m, 4H; Ar—H), 5.95 (s, 1H; OH, D$_2$O ex.), 4.72 (s, 2H; triazolone-CH$_2$), 4.66–4.61 (d, 1H; J=15.0 Hz; triazole-CH$_2$), 4.23–4.17 (d, 1H; J=14.7 Hz; triazole-CH$_2$), 3.38–3.36 (d, 4H; piperazine-CH$_2$—), 3.31–3.29 (d, 4H; piperazine-CH$_2$—) & 2.31 (s, 3H; triazolne-CH$_3$)ppm.

Compound No. 40:

2-[2-(2,4-Difluorophenyl)-2-hydroxy-3-(1H-1,2,4-triazol-1-yl)propyl]-4-{4-[4-(2,4-dinitrophenyl)-1-piperazinyl]phenyl}-3-(2H,4H)-1,2,4-triazolone NMR (CDCl$_3$):-δ 8.74–8.73 (d, 1H; Ar—H), 8.33–8.29 (m, 1H; Ar—H), 8.17 (s, 1H; Ar—H), 7.82 (s, 1H; Ar—H), 7.60–7.53 (m, 2H; Ar—H), 7.32–7.29 (d, 3H; Ar—H), 7.19–7.16 (d, 1H; Ar—H), 6.98–6.95 (d, 2H; Ar—H), 6.85–6.79 (m, 2H; Ar—H), 5.90 (s, 1H; OH, D$_2$O ex.), 4.72 (s, 2H; triazolone-CH$_2$), 4.62–4.57 (d, 1H; J=14.7 Hz; triazole-CH$_2$), 4.22–4.18 (d, 1H; J=14.7 Hz; triazole-CH$_2$), 3.46–3.43 (d, 8H; piperazine-CH$_2$—)ppm.

Compound No. 41:

2-[2-(2,4-Difluorophenyl)-2-hydroxy-3-(1H-1,2,4-triazol-1-yl)propyl]-4-{4-[4-(4-methoxyphenyl)-1-piperazinyl]phenyl}-3-(2H,4H)-1,2,4-triazolone NMR (CDCl$_3$):-δ 8.19 (s, 1H; Ar—H), 7.86 (s, 1H; Ar—H), 7.65–7.57 (q, 1H; Ar—H), 7.51 (s, 1H; Ar—H), 7.31–7.28 (m, 2H; Ar—H), 7.04–6.81 (m, 8H; Ar—H), 5.96 (s, 1H; OH, D$_2$O ex.), 4.73 (s, 2H; triazolone-CH$_2$), 4.66–4.61 (d, 1H; J=15.0 Hz; triazole-CH$_2$), 4.24–4.19 (d, 1H; J=15.0 Hz; triazole-CH$_2$), 3.81 (s, 3H, —OCH$_3$), 3.40–3.37 (d, 4H; J piperazine-CH$_2$—), & 3.26–3.23 (d, 4H; piperazine-CH$_2$—) ppm.

Compound No. 42:

2-[2-(2,4-Difluorophenyl)-2-hydroxy-3-(1H-1,2,4-triazol-1-yl)propyl]-4-{4-[4-(2-methoxyphenyl)-1-piperazinyl]phenyl}-3-(2H,4H)-1,2,4-triazolone NMR (CDCl$_3$):-δ 8.19 (s, 1H; Ar—H), 7.85 (s, 1H; Ar—H), 7.64–7.55 (q, 1H; Ar—H), 7.50 (s, 1H; Ar—H), 7.29–7.26 (t, 2H, Ar—H), 7.09–6.80 (m, 8H; Ar—H), 4.72 (s, 2H; triazolone-CH$_2$), 4.66–4.61 (d, 1H; J=15.0 Hz; triazole-CH$_2$), 4.23–4.18 (d, 1H; J=14.7 Hz; triazole-CH$_2$), 3.91 (s, 3H, —OCH$_3$), 3.43–3.39 (t, 4H; piperazine-CH$_2$—), & 3.25–3.22 (t, 4H; piperazine-CH$_2$—)ppm.

Compound No. 43:

2-[2-(2,4-Difluorophenyl)-2-hydroxy-3-(1H-1,2,4-triazol-1-yl)propyl]-4-{4-[4-(4-fluorophenyl)-1-piperazinyl]phenyl}-3-(2H,4H)-1,2,4-triazolone NMR (CDCl$_3$):-δ 8.17 (s, 1H; Ar—H), 7.84 (s, 1H; Ar—H), 7.59–7.57 (q, 1H; Ar—H), 7.49 (s, 1H; Ar—H), 7.29–7.26 (t, 2H; Ar—H), 7.03–6.79 (m, 8H; Ar—H), 5.93 (s, 1H; OH, D$_2$O ex.), 4.71 (s, 2H; triazolone-CH$_2$), 4.64–4.59 (d, 1H; J=14.7 Hz; triazole-CH$_2$), 4.21–4.17 (d, 1H; J=14.7 Hz; triazole-CH$_2$), 3.38–3.34 (t, 4H; piperazine-CH$_2$—), & 3.27–3.24 (t, 4H; piperazine-CH$_2$—)ppm.

Compound No. 44:

2-[2-(2,4-Difluorophenyl)-2-hydroxy-3-(1H-1,2,4-triazol-1-yl)propyl]-4-{4-[4-(4-hydroxyphenyl)-1-piperazinyl]phenyl}-3-(2H,4H)-1,2,4-triazolone NMR (CDCl$_3$):-δ 8.86 (s, 1H; Ar—H), 8.32–8.27 (d, 2H; Ar—H), 7.72 (s, 1H; Ar—H), 7.44–7.41 (d, 2H; Ar—H), 7.33–7.30 (q, 1H; Ar—H), 7.18–7.14 (t, 1H; Ar—H), 7.10–7.07 (d, 2H; Ar—H), 6.94–6.84 (m, 3H; Ar—H), 6.69–6.66 (d, 2H; Ar—H), 6.19 (s, 1H; OH, D$_2$O ex.), 4.83–4.77 (d, 1H; J=14.4 Hz; triazole-CH$_2$), 4.66–4.62 (d, 1H; J=14.4 Hz; triazole-CH$_2$), 4.20 (s, 2H; triazolone-CH$_2$), 3.35–3.32 (merging with DMSO-d$_6$ signal)(s, 4H; piperazine-CH$_2$—), & 3.11–3.09 (d, 4H; piperazine-CH$_2$—)ppm.

Compound No. 45:

2-[2-(2,4-Difluorophenyl)-2-hydroxy-3-(1H-1,2,4-triazol-1-yl)propyl]-4-{4-[1-phenyl-1-piperazinyl]phenyl}-3-(2H,4H)-1,2,4-triazolone NMR(CDCl$_3$):-δ 8.19 (s, 1H; Ar—H), 7.85 (s, 1H; Ar—H), 7.64–7.56 (s, 1H; Ar—H), 7.50 (s, 1H; Ar—H), 7.35–7.27 (m, 5H: Ar—H), 7.03–6.80 (m, 7H; Ar—H), 5.95 (s, 1H; OH, D$_2$O ex.), 4.72 (s, 2H; triazolone-CH$_2$), 4.66–4.61 (d, 1H; J=14.7 Hz; triazole-CH$_2$), 4.23–4.18 (d, 1H; J=14.7 Hz; triazole-CH$_2$), & 3.37 (s, 8H; piperazine-CH$_2$—)ppm.

Compound No. 46:

2-[2-(2,4-Difluorophenyl)-2-hydroxy-3-(1H-1,2,4-triazol-1-yl)propyl]-4-{4-[4-(4-chlorophenyl)-1-piperazinyl]phenyl}-3-(2H,4H)-5-methyl-1,2,4-triazolone NMR(CDCl$_3$):-δ 8.17 (s, 1H; Ar—H), 7.81 (s, 1H; Ar—H), 7.58–7.55 (m, 1H; Ar—H), 7.32–7.26 (m, 2H; Ar—H), 7.06–6.78 (m, 9H; Ar—H), 6.06 (s, 1H; OH, D$_2$O ex.), 4.70 (s, 2H; triazolone-CH$_2$), 4.54–4.49 (d, 1H; J=14.7 Hz; triazole-CH$_2$), 4.19–4.14 (d, 1H; J=14.7 Hz; triazole-CH$_2$), 3.37–3.33 (t, 8H; piperazine-CH$_2$—), & 2.03 (s, 3H; triazolone-CH$_3$)ppm.

Compound No. 47:

2-[2-(2,4-Difluorophenyl)-2-hydroxy-3-(1H-1,2,4-triazol-1-yl)propyl]-4-{4-[4-(4-chlorophenyl)-1-piperazinyl]phenyl}-3-(2H,4H)-1,2,4-triazolone NMR (CDCl$_3$):-δ 8.17 (s, 1H; Ar—H), 7.83 (s, 1H; Ar—H), 7.62–7.54, (m, 1H; Ar—H), 7.50 (s, 1H; Ar—H), 7.29–7.23 (m, 4H; Ar—H), 7.01–6.98 (d, 2H; Ar—H), 6.91–6.79 (m, 8H; Ar—H), 5.96 (s, 1H; OH, D$_2$O ex.), 4.72 (s, 2H; triazolone-CH$_2$), 4.63–4.59 (d, 1H; J=14.7 Hz; triazole-CH$_2$), & 4.22–4.17 (d, 1H; J=14.7 Hz; triazole-CH$_2$), & 3.37–3.30 (q, 8H; piperazine-CH$_2$—)ppm.

Compound No. 48:

2-[2-(2,4-Difluorophenyl)-2-hydroxy-3-(1H-1,2,4-triazol-1-yl)propyl]-4-{4-[4-(5-chloro-2-methylphenyl)-1-piperazinyl]phenyl}-3-(2H,4H)-1,2,4-triazolone NMR (CDCl$_3$):-δ 8.28 (s, 1H; Ar—H), 7.90 (s, 1H; Ar—H), 7.66–7.58 (m, 1H; Ar—H), 7.53 (s, 1H; Ar—H), 7.32–7.29 (t, 2H; Ar—H), 7.29–7.26 (d, 2H; Ar—H), 7.16–7.14 (d, 1H; Ar—H), 7.04–7.02 (d, 4H, Ar—H), 6.89–6.82 (m, 2H, Ar—H), 5.96 (br, 1H; OH, D$_2$O ex.), 4.74 (s, 2H; triazolone-CH$_2$), 4.67–4.62 (d, 1H; J=14.7 Hz; triazole-CH$_2$), & 4.26–4.20 (d, 1H; J=14.7 Hz; triazole-CH$_2$), 3.40–3.33 (m, 4H; piperazine-CH$_2$—), 3.10–3.07 (m, 4H; piperazine-CH$_2$—)ppm.

Compound No. 49:

2-[2-(2,4-Difluorophenyl)-2-hydroxy-3-(1H-1,2,4-triazol-1-yl)propyl]-4-{4-[4-(3-chloro-4-methylphenyl)-1-piperazinyl]phenyl}-3-(2H,4H)-1,2,4-triazolone NMR (CDCl$_3$):-δ 8.20 (s, 1H; Ar—H), 7.87 (s, 1H; Ar—H), 7.65–7.58 (q, 1H; Ar—H), 7.52 (s, 1H; Ar—H), 7.31–7.29 (d, 2H; Ar—H), 7.16–7.14 (d, 2H; Ar—H), 7.04–6.98 (m, 3H; Ar—H), 6.88–6.80 (m, 3H; Ar—H), 5.96 (s, 1H; OH, D$_2$O ex.), 4.74 (s, 2H; triazolone-CH$_2$), 4.67–4.62 (d, 1H; J=14.7 Hz; triazole-CH$_2$), & 4.24–4.17 (d, 1H; J=14.7 Hz; triazole-CH$_2$), & 3.3–3.33 (m, 8H; piperazine-CH$_2$—)ppm.

Compound No. 50:
2-[2-(2,4-Difluorophenyl)-2-hydroxy-3-(1H-1,2,4-triazol-1-yl)propyl]-4-{4-[4-(2,4-dichlorophenyl)-1-piperazinyl]phenyl}-3-(2H,4H)-1,2,4-triazolone NMR (CDCl$_3$):- . . . 8.19 (s, 1H; Ar—H), 7.86 (s, 1H; Ar—H), 7.65–7.56 (m, 1H; Ar—H), 7.51 (s, 1H; Ar—H), 7.43–7.42 (d, 1H; Ar—H), 7.31–7.23 (m, 3H; Ar—H), 7.03–7.01 (d, 3H; Ar—H), 6.88–6.81 (m, 2H; Ar—H), 5.93 (s, 1H; OH, D$_2$O ex.), 4.73 (s, 2H; triazolone-CH$_2$), 4.66–4.61 (d, 1H; J=14.7 Hz; triazole-CH$_2$), & 4.24–4.19 (d, 1H; J=14.7 Hz; triazole-CH$_2$), 3.42–3.39 (m, 4H; piperazine-CH$_2$—), 3.22–3.18 (m, 4H; piperazine-CH$_2$—)ppm.

Compound No. 51:
2-[2-(2,4-Difluorophenyl)-2-hydroxy-3-(1H-1,2,4-triazol-1-yl)propyl]-4-{4-[4-(3-trifluoromethylphenyl)-1-piperazinyl]phenyl}-3-(2H,4H)-1,2,4-triazolone NMR (CDCl$_3$):-δ 8.16 (s, 1H; Ar—H), 7.83 (s, 1H; Ar—H), 7.62–7.57 (q, 1H; Ar—H), 7.49 (s, 1H; Ar—H), 7.40–7.35 (t, 1H; Ar—H), 7.29–7.26 (d, 2H; Ar—H), 7.15–7.09 (m, 3H; Ar—H), 7.01–6.98 (d, 2H; Ar—H), 6.84–6.78 (m, 2H; Ar—H), 5.90 (s, 1H; OH, D$_2$O ex.), 4.70 (s, 2H; triazolone-CH$_2$), 4.63–4.58 (d, 1H; J=14.7 Hz; triazole-CH$_2$), & 4.21–4.16 (d, 1H; J=14.7 Hz; triazole-CH$_2$), & 3.37 (s, 8H; piperazine-CH$_2$—)ppm.

Compound No. 52:
2-[2-(2,4-Difluorophenyl)-2-hydroxy-3-(1H-1,2,4-triazol-1-yl)propyl]-4-{4-[4-(2,4-difluorophenyl)-1-piperazinyl]phenyl}-3-(2H,4H)-1,2,4-triazolone NMR (CDCl$_3$):- . . . 8.16 (s, 1H; Ar—H), 7.83 (s, 1H; Ar—H), 7.62–6.78 (m, 11H; Ar—H), 5.90 (s, 1H, OH), 4.70 (s, 2H; triazolone-CH$_2$), 4.63 (d, 1H; J=14.9 Hz; triazole-CH$_2$—), 4.19 (d, 1H; J=14.9 Hz; triazole-CH$_2$—), 3.35 (bm, 4H; piperazine-CH$_2$), 3.16 (bm, 4H; piperazine —CH$_2$)ppm.

Compound No. 53:
2-[2-(2,4-Difluorophenyl)-2-hydroxy-3-(1H-1,2,4-triazol-1-yl)propyl]-4-{4-[4-(3-chloro-4-fluorophenyl)-1-piperazinyl]phenyl}-3-(2H,4H)-1,2,4-triazolone NMR (CDCl$_3$):- . . . 8.17 (s, 1H; Ar—H), 7.84 (s, 1H; Ar—H), 7.62–7.54 (m, 1H; Ar—H), 7.49 (s, 1H; Ar—H), 7.29–7.26 (m, 2H; Ar—H), 7.08–6.95 (m, 4H; Ar—H), 6.83–6.98 (m, 3H; Ar—H), 5.90 (s, 1H; OH, D$_2$O ex.), 4.71 (s, 2H; triazolone-CH$_2$), 4.63–4.59 (d, 1H; J=14.8 Hz; triazole-CH$_2$), 4.21–4.16 (d, 1H; J=14.8 Hz; triazole-CH$_2$), 3.35–3.34 (d, 4H; 2×piperazine-CH$_2$—) & 3.27–3.26 (d, 4H; 2×piperazine-CH$_2$—)ppm.

Compound No. 54:
2-[2-(2,4-Difluorophenyl)-2-hydroxy-3-(1H-1,2,4-triazol-1-yl)propyl]-4-{4-[4-(2,4-dimethylphenyl)-1-piperazinyl]phenyl}-3-(2H,4H)-1,2,4-triazolone NMR (CDCl$_3$):- . . . 8.16 (s, 1H; Ar—H), 7.82 (s, 1H; Ar—H), 7.59–7.57 (m, 1H; Ar—H), 7.48 (s, 1H; Ar—H), 7.24–7.27 (m, 3H; Ar—H), 7.02–6.78 (m, 7H; Ar—H), 5.93 (s, 1H; OH, D$_2$O ex.), 4.63–4.70 (s, 2H; triazolone-CH$_2$), 4.47–4.58 (d, 1H; J=15 Hz; triazole-CH$_2$), 4.21–4.16 (d, 1H; J=15 Hz; triazole-CH$_2$), 3.35–3.32 (m, 4H; 2×piperazine-CH$_2$—), 3.04–3.01 (m, 4H; 2×piperazine-CH$_2$—) 2.30 (s, 3H; CH$_3$) & 2.28 (s, 3H, CH$_3$)ppm.

Compound No. 57:
2-[2-(2,4-Difluorophenyl)-2-hydroxy-3-(1H-1,2,4-triazol-1-yl)propyl]-4-{4-[4-(3-chlorophenyl)-1-piperazinyl]phenyl}-3-(2H,4H)-1,2,4-triazolone NMR (CDCl$_3$):- . . . 8.16 (s, 1H; Ar—H), 7.83 (s, 1H; Ar—H), 7.59–7.57 (q, 1H; Ar—H), 7.49 (s, 1H; Ar—H), 7.29–7.26 (d, 2H; Ar—H), 7.22–7.17 (t, 1H; Ar—H), 7.00–6.97 (d, 2H; Ar—H), 6.92–6.91 (m, 1H; Ar—H), 6.87–6.78 (m, 4H; Ar—H), 5.90 (s, 1H; OH, D$_2$O ex.), 4.70 (s, 2H; triazolone-CH$_2$), 4.63–4.58 (d, 1H; J=14.7 Hz; triazole-CH$_2$), & 4.21–4.16 (d, 1H; J=14.7 Hz; triazole-CH$_2$), & 3.34 (s, 8H; piperazine-CH$_2$—)ppm.

Compound No. 58:
2-[2-(2,4-Difluorophenyl)-2-hydroxy-3-(1H-1,2,4-triazol-1-yl)propyl]-4-{4-[4-(2-chloro-4-fluorophenyl)-1-piperazinyl]phenyl}-3-(2H,4H)-1,2,4-triazolone NMR (CDCl$_3$):-δ 8.18 (s, 1H; Ar—H), 7.84 (s, 1H; Ar—H), 7.59–7.57 (m, 1H; Ar—H), 7.49 (s, 1H; Ar—H), 7.29–6.79 (m, 9H; Ar—H), 5.92 (s, 1H; OH, D$_2$O ex.), 4.71 (s, 2H; triazolone-CH$_2$), 4.64–4.59 (d, 1H; J=14.8 Hz; triazole-CH$_2$), 4.22–4.17 (d, 1H; J=14.8 Hz; triazole-CH$_2$), 3.38–3.35 (t, 4H; 2×piperazine-CH$_2$—) & 3.23–3.20 (t, 4H; 2×piperazine-CH$_2$—)ppm.

Compound No. 59:
2-[2-(2,4-Difluorophenyl)-2-hydroxy-3-(1H-1,2,4-triazol-1-yl)propyl]-4-{4-[4-(2-methoxy-5-fluorophenyl)-1-piperazinyl]phenyl}-3-(2H,4H)-1,2,4-triazolone NMR (CDCl$_3$):-δ 8.19 (s, 1H; Ar—H), 7.85 (s, 1H; Ar—H), 7.60–7.57 (m, 1H; Ar—H), 7.50 (s, 1H; Ar—H), 7.29–7.26 (m, 3H; Ar—H), 7.02–6.99 (d, 2H; Ar—H), 6.85–6.78 (m, 3H; Ar—H), 6.72–6.68 (m, 2H; Ar—H), 5.95 (s, 1H; OH, D$_2$O ex.), 4.72 (s, 2H; triazolone-CH$_2$), 4.65–4.60 (d, 1H; J=14.8 Hz; triazole-CH$_2$), 4.22–4.17 (d, 1H; J=14.8 Hz; triazole-CH$_2$), 3.87 (s, 3H; OCH$_3$), 3.41–3.38 (d, 4H; 2×piperazine-CH$_2$—) & 3.22–3.21×piperazine-CH$_2$—) ppm.

PHARMACOLOGICAL ACTIVITY

Compounds of the Formulae IA, IB, II and III as shown herein, and their salts are useful in the curative or prophylactic treatment of fungal infections in animals, to including humans. For example, they are useful in treating topical fungal infection in man caused by, among other organisms, species of candida, Trichophyton, Microsporum or Epidermophyton in mucosal infections caused by *C. albicans* (e.g., thrush and vaginal candidiasis). They can also be used in the treatment of systemic fungal infections caused by, for example, species of Candida (e.g., *Candida albicans*), *Cryptococcus neoformans* or *Aspergillus fumigatus*.

The compounds of the present invention have been found to have unexpectedly good activity against clinically important Aspergillus species fungi.

The in vitro evaluation of the antifungal activity of the compounds can be performed by determining the minimum inhibitory concentration (MIC) which is the concentration of the test compound in *Rosewell Park Memorial Institute* (*RPMI*) 1640 liquid medium buffered with (3-[Morpholino] propanesulphonic acid) MOPS to pH7, at which there is significant inhibition of the particular fungi In practice the National Committee for Clinical Laboratory Standard (NCCLS) M27A document for Candida and Cryptococcus and M38P for Aspergillus was used to determine the MIC against yeast and filamentous fungi with suitable modifications for dermatophytes. Two quality control strains were included each time the MIC were determined and readings recorded only when the QC results fell into the acceptable range. After MIC results had been recorded, 100 μl from each of the well showing no growth was spread over Sabouraud Dextrose Agvar (SDA) to determine the minimum fungicidal concentration.

The in vivo evaluation of the compound can be carried out at a series of dose levels by oral or I.V. injection to mice which are inoculated I.V. with the minimum lethal dose of *Candida albicans, Cryptococcus neoformans* or *Aspergillus fumigatus* by the tail vein. Activity is based on the survival of a treated group of mice after the death of an untreated group of mice. For Aspergillus and Cryptococcus infections target organs were cultured after treatment to document the number of mice cured of the infection for further assessment of activity.

For human use, the antifungal compounds of the formula and their salts can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

The solubility of a compound of the Formulae IA, IB, II and IIII in an aqueous medium may be improved by complexation with a hydroxyalkyl derivative of a cyclodextrin in the preparation of an appropriate pharmaceutical composition.

For oral and parenteral administration to human patients, the daily dosage level of the antifungal compounds of the Formulae IA, IB, II and III and their salts will be from 0.01 to 20 mg/kg (in single or divided doses) when administered by either the oral or parenteral routes. Thus tablets or capsules of the compound will contain from 5 mg to 0.5 gm of active compound for administration one, two or more at a time, as appropriate. The physician in any event will determine the actual dosage which will be most suitable for an individual patient and it will vary with age, weight and response of the particular patient. The above dosages are exemplary of the average case, there can, of course, be individual instances, where higher or lower dosage ranges are required and such are within the scope of this invention.

Alternatively, the antifungal compound or Formulae IA, IB, II and III can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin, or they can be incorporated, at a concentration between 1 and 10% into an ointment consisting of a white wax or white soft paraffin base together with such stabilizers and preservatives as may be required.

Cryptococcosis is a leading cause of morbidity and mortality among AIDS patients. In many patients Cryptococcosis is the first indication of AIDS. The incidences of life-threatening cryptococcal infection among patients with AIDS has been estimated to vary from 10–30%. During initial therapy, 10–20% of these patients die and 30–60% patients succumb within 12 months (Powderly WG: Cryptococcus meningitis and AIDS Clin. Infect. Dis. 1993; 17: 837–842).

Amphotericin B has changed disseminated cryptococcosis from uniformly fatal infection to curable infection, but since Amphotericin B penetrates the central nervous system poorly, intraventricular injection may have to be administered for successful management of severe cases of Cryptococcal meningitis. Fluconazole has excellent pharmacokinetics in CSF and performs equally well in patients with Cryptococcal meningitis. However, there is a trend towards earlier deaths and longer period before sterilisation of the CSF (NIAID [National Institute of Allergy and Infection Disease] Mycoses study group and AIDS clinical trials group: comparison 4Z of Amphotericin B and Fluconazole in the treatment of acute AIDS associated Cryptococcus meningitis (N Engl J Med 1992; 326: 83–89).

Invasive aspergillosis has become a leading cause of death, mainly among patients suffering from acute leukaemia or after allogenic bone marrow transfusion and after cytotoxic treatment of these conditions. It also occurs in patients with conditions such as AIDS and chronic granulomatous disease. At present, only Amphotericin B and Itraconazole are available for treatment of aspergillosis. In spite of their activity in vitro, the effect of these drugs in vivo against *Aspergillus fumigatus* remains low and as a consequence mortality from invasive aspergillosis remains high.

In vitro Activity:

Compounds of this invention have potent in vitro activity against a wide range of fungal pathogens tested. They are active against all species of Candida, *Histoplasma capsulatum, Cryptococcus neoformans*, dermatophytes, *Aspergillus fumigatus* and *A. flavus*. The action on many of these strains, especially against Cryptococcus and Aspergillus is fungicidal in vitro.

Table containing the biological evaluation of these compounds

| Compound | Candida albicans | | | C. krusei | | C. parapsilosis | Candida tropicalis | C. glabrata | H. | C. neoformans | | A. fumigatus |
|---|---|---|---|---|---|---|---|---|---|---|---|---|
| No. | A 26 | 1.549 | Y-01-19 | 766-1 | Q. C | Q. C. | ATCC | 90030 | capsulatum | I | M 106 | 1008 |
| 1 | <0.03 | 0.12 | 0.12 | 0.25 | 0.12 | <0.03 | <0.03 | 0.25 | 0.06 | <0.03 | <0.03 | 0.12 |
| 2 | <0.03 | 1.00 | 0.25 | 2.00 | 1.00 | <0.03 | <0.03 | 0.50 | <0.03 | <0.03 | <0.03 | >16 |
| 3 | <0.03 | 0.12 | 0.50 | 1.00 | 0.50 | <0.03 | <0.03 | 0.25 | <0.03 | <0.03 | <0.03 | 0.25 |
| 4 | <0.03 | 4.00 | >16 | >16 | >16 | 0.25 | <0.03 | 2.00 | 0.50 | 0.25 | 1.00 | >16 |
| 5 | <0.03 | 2.00 | 0.12 | 0.50 | 0.12 | <0.03 | <0.03 | 1.00 | <0.03 | <0.03 | <0.03 | 0.50 |
| 6 | <0.03 | 2.00 | 8.00 | >16 | 16.0 | 0.125 | <0.03 | >16 | 0.12 | 0.25 | 2.00 | >16 |
| 7 | <0.03 | 0.25 | 0.12 | 0.25 | 0.12 | <0.03 | <0.03 | 0.12 | 0.12 | <0.03 | <0.03 | 0.25 |
| 8 | <0.03 | >16 | >16 | >16 | >16 | 1.00 | >16 | >16 | 2.00 | 16.00 | 16.00 | >16 |
| 9 | <0.03 | 0.25 | 0.25 | 0.50 | 0.12 | <0.03 | <0.03 | 0.25 | 0.06 | <0.03 | <0.03 | 0.50 |
| 10 | <0.03 | 0.50 | 1.00 | >16 | 1.00 | <0.03 | <0.03 | 0.50 | 0.06 | 0.06 | <0.03 | >16 |

-continued

Table containing the biological evaluation of these compounds

| Compound No. | Candida albicans A 26 | Candida albicans 1.549 | Candida albicans Y-01-19 | C. krusei 766-1 | C. krusei Q. C | C. parapsilosis Q. C. | Candida tropicalis ATCC | C. glabrata 90030 | H. capsulatum | C. neoformans I | C. neoformans M 106 | A. fumigatus 1008 |
|---|---|---|---|---|---|---|---|---|---|---|---|---|
| 11 | <0.03 | 0.06 | 0.12 | 0.25 | 0.12 | <0.03 | <0.03 | 0.25 | <0.03 | <0.03 | <0.03 | 0.25 |
| 12 | <0.03 | 4.00 | 8.00 | >16 | 8.00 | 0.06 | <0.03 | 4.00 | <0.03 | 0.12 | 0.25 | >16 |
| 13 | <0.03 | 0.12 | 0.25 | 0.50 | 0.12 | <0.03 | <0.03 | 0.50 | 0.06 | <0.03 | <0.03 | 0.25 |
| 14 | <0.03 | 2.00 | 2.00 | >16 | 16.0 | 0.06 | <0.03 | 2.00 | 0.12 | 0.50 | <0.03 | >16 |
| 15 | <0.03 | 1.00 | 0.25 | 0.50 | 0.25 | <0.03 | <0.03 | 0.50 | 0.12 | <0.03 | <0.03 | 0.50 |
| 16 | <0.03 | 4.00 | 1.00 | >16 | 1.00 | 0.06 | <0.03 | 0.50 | 0.50 | 0.12 | 0.12 | >16 |
| 17 | <0.03 | 0.25 | 0.25 | 0.50 | 0.50 | <0.03 | <0.03 | 0.50 | 0.25 | <0.03 | <0.03 | 0.25 |
| 18 | <0.03 | 2.00 | 1.00 | >16 | 2.00 | 0.25 | <0.03 | 1.00 | 0.25 | 0.12 | 0.25 | >16 |
| 19 | <0.03 | 1.00 | 1.00 | >16 | 0.50 | 0.06 | <0.03 | >16 | 0.50 | <0.03 | <0.03 | >16 |
| 20 | <0.03 | 8.00 | 2.00 | >16 | 2.00 | 0.12 | <0.03 | 2.00 | 0.50 | 0.25 | 0.25 | >16 |
| 21 | <0.03 | 0.25 | 0.25 | 0.50 | 0.25 | 0.06 | <0.03 | 0.50 | 0.12 | <0.03 | <0.03 | 1.00 |
| 22 | <0.03 | 2.00 | 1.00 | 8.00 | 1.00 | 0.25 | <0.03 | 1.00 | >16 | 0.12 | 0.06 | >16 |
| 23 | <0.03 | 0.25 | 0.50 | 0.50 | 0.25 | <0.03 | <0.03 | 0.50 | 0.06 | <0.03 | <0.03 | 1.00 |
| 24 | <0.03 | 2.00 | 16.00 | >16 | 16.0 | 0.25 | <0.03 | 2.00 | 0.25 | 0.50 | 1.00 | >16 |
| 25 | <0.03 | 0.06 | 0.12 | 0.12 | 0.06 | <0.03 | <0.03 | 0.12 | 0.06 | <0.03 | <0.03 | 0.50 |
| 26 | <0.03 | 0.25 | 1.00 | 2.00 | 0.50 | <0.03 | <0.03 | 1.00 | 0.12 | <0.03 | <0.03 | 8.00 |
| 27 | <0.03 | 1.00 | 0.50 | 2.00 | 0.50 | <0.03 | <0.03 | 1.00 | <0.03 | <0.03 | <0.03 | >16 |
| 28 | <0.03 | 8.00 | 4.00 | >16 | 16.0 | 0.25 | <0.03 | 4.00 | 2.00 | 0.25 | 1.00 | >16 |
| 29 | <0.03 | 0.25 | 0.25 | 0.50 | 0.25 | <0.03 | <0.03 | 0.50 | 0.25 | <0.03 | <0.03 | 0.50 |
| 30 | <0.03 | 0.50 | 1.00 | 8.00 | 1.00 | 0.12 | <0.03 | 1.00 | 0.50 | 0.12 | 0.25 | >16 |
| 31 | <0.03 | >16 | 0.12 | 0.50 | 0.12 | <0.03 | <0.03 | 0.50 | 0.06 | <0.03 | <0.03 | 1.00 |
| 32 | <0.03 | >16 | 4.00 | >16 | 4.00 | 0.50 | <0.03 | 2.00 | 0.25 | 0.50 | 0.50 | >16 |
| 33 | <0.03 | 0.13 | 0.13 | 0.25 | 0.06 | <0.03 | <0.03 | 0.25 | 0.12 | <0.03 | <0.03 | 0.50 |
| 34 | <0.03 | 1.00 | 1.00 | 2.00 | 1.00 | 0.25 | <0.03 | 0.50 | 0.12 | 0.25 | <0.03 | >1679 |
| 35 | <0.02 | 1.56 | 3.12 | 12.50 | 3.12 | 0.20 | <0.02 | 12.50 | 0.20 | 0.80 | 3.12 | >12.5 |
| 36 | <0.02 | 0.20 | 0.40 | 3.12 | 1.56 | <0.02 | <0.02 | 3.12 | <0.02 | 0.20 | 0.40 | >12.5 |
| 37 | <0.03 | 0.06 | 0.06 | 0.25 | 0.06 | <0.03 | <0.03 | 0.12 | <0.03 | <0.03 | <0.03 | >16 |
| 38 | >16 | >16 | >16 | >16 | >16 | >16 | >16 | >16 | >16 | >16 | >16 | >16 |
| 39 | <0.02 | 0.10 | 0.02 | 0.80 | 0.10 | <0.02 | 6.25 | 0.10 | 0.05 | <0.02 | 0.05 | 6.25 |
| 40 | <0.02 | 0.40 | 0.40 | 6.25 | 1.56 | 0.05 | 1.56 | 0.80 | 0.05 | 0.05 | 0.20 | 1.56 |
| 41 | <0.02 | 0.05 | 0.10 | 1.56 | 0.40 | <0.02 | 3.12 | 0.80 | <0.02 | 0.10 | 0.40 | 6.25 |
| 42 | 0.05 | 0.40 | 12.50 | 3.12 | 1.56 | <0.02 | 12.50 | 1.56 | 0.05 | 0.20 | 0.80 | >12.5 |
| 43 | <0.02 | <0.02 | 0.05 | 1.56 | 0.20 | <0.02 | 12.50 | 0.40 | <0.02 | 0.05 | 0.05 | >12.5 |
| 44 | >12.5 | >12.5 | 1.56 | >12.5 | 6.25 | 0.20 | 6.25 | 6.25 | 1.56 | 1.56 | 3.12 | >12.5 |
| 45 | <0.02 | 0.05 | 0.05 | 0.80 | 0.10 | <0.02 | 3.12 | 0.10 | 3.12 | <0.02 | 0.10 | >12.5 |
| 46 | <0.02 | 0.40 | 0.40 | 3.12 | 0.80 | <0.02 | 0.05 | 6.25 | 0.10 | 0.05 | 0.40 | >12.5 |
| 47 | <0.02 | 0.20 | 0.20 | 1.56 | 1.56 | <0.02 | <0.02 | 3.12 | 0.05 | <0.02 | 0.40 | 3.12 |
| 48 | <0.03 | 0.50 | 0.50 | 1.00 | 0.50 | 0.12 | <0.03 | 1.00 | 0.25 | <0.03 | 0.06 | >16 |
| 49 | <0.03 | <0.03 | <0.03 | 0.25 | 0.06 | <0.03 | <0.03 | 0.25 | <0.03 | <0.03 | <0.03 | 4.00 |
| 50 | <0.03 | 0.12 | 0.12 | 0.50 | 0.25 | <0.03 | <0.03 | 0.50 | <0.03 | <0.03 | <0.03 | 2.00 |
| 51 | <0.03 | 0.25 | 0.25 | 1.00 | 0.25 | 0.06 | <0.03 | 1.00 | <0.03 | <0.03 | <0.03 | >16 |
| 52 | <0.03 | 0.06 | 0.12 | 4.00 | 0.50 | <0.03 | <0.03 | 1.00 | <0.03 | <0.03 | <0.03 | >16 |
| 53 | <0.03 | 0.06 | <0.03 | 0.50 | 0.12 | <0.03 | <0.03 | 0.50 | <0.03 | <0.03 | <0.03 | 4.00 |
| 54 | <0.03 | 8.00 | 0.12 | 0.50 | 0.12 | <0.03 | <0.03 | 1.00 | 0.06 | <0.03 | <0.03 | 2.00 |
| 55 | <0.03 | 0.03 | 0.03 | 1.00 | 0.12 | <0.03 | <0.03 | 0.25 | 0.004 | <0.03 | 0.02 | >16 |
| 56 | <0.03 | 0.06 | 0.03 | 1.00 | 0.25 | <0.03 | <0.03 | 0.25 | 0.004 | <0.03 | 0.03 | >16 |
| 57 | <0.03 | 0.25 | 0.12 | 0.50 | 0.25 | <0.03 | <0.03 | 0.25 | 0.06 | <0.03 | <0.03 | >16 |
| 58 | <0.03 | 0.03 | 0.03 | 1.00 | 0.25 | <0.03 | <0.03 | 0.25 | 0.004 | <0.03 | <0.03 | 2.00 |
| 59 | <0.03 | 1.00 | 0.50 | 4.00 | 1.00 | <0.03 | <0.03 | 1.00 | <0.03 | <0.03 | 0.12 | >16 |
| 60 | <0.03 | >16 | 0.25 | 1.00 | 0.25 | <0.03 | <0.03 | 0.50 | <0.03 | <0.03 | <0.03 | >16 |
| 61 | <0.03 | 0.25 | 0.12 | 0.50 | 0.25 | <0.03 | <0.03 | 0.50 | <0.03 | <0.03 | <0.03 | >16 |
| 62 | <0.03 | 4.00 | 0.50 | 2.00 | 0.50 | <0.03 | <0.03 | 1.00 | <0.03 | <0.03 | 0.12 | 16.00 |
| 63 | <0.03 | 0.06 | 0.12 | 8.00 | 0.25 | <0.03 | <0.03 | 0.50 | <0.03 | <0.03 | <0.03 | >16 |

In Vivo Activity:

Compounds of this invention have enhanced antifungal activity against the important fungal pathogens of men and animals.

a) Anti Candida Activity:

A single oral dose of 12.5 mg/kg bw. (0.25 mg per mouse) is adequate to offer significant protection to mice infected via the tail vein by lethal dose of *C. albicans* A-26.

Summary of Single Dose Studies with Azoles in Systemic Infection with *Candida albicans* A-26

| Example | Mean survival days |
|---|---|
| 1(βcd) | 12.1 |
| 1 | 10.5 |
| Sham treated | 3.5 | b) Anti Cryptococcal Activity:

The compounds of this invention cross the blood brain barrier to excert their potent anti cryptococcal activity in the brain. In an animal model where lethal infection (1 million cells of *C. neoformans*) were injected into the cranium of the animal, oral dosing with 25 mg/kg bw. BID for 8 days reduced the count by 4 logs, causing 99.99% reduction in the fungal load.

c) Anti Aspergillus Activity:

Doses as low as 6.25 mg/kg bw. significantly increased the survival of mice infected via the tail vein with lethal dose of *Aspergillus fumigatus* conidia.

d) Anti Dermatophyte Activity:

Single local application of the drug had significant effect on *Trichophyton mentagrophyte* infection of guinea pig skin.

We claim:

1. A compound of Formula IA

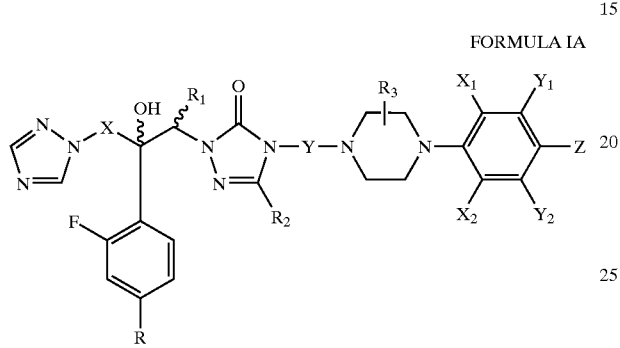

FORMULA IA and its pharmaceutically acceptable salts, enantiomers, diastereomers, N-oxides, wherein X is selected from the group consisting of $CH_2$, CO, CS, $SO_2$ and —N=N—, R is selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino (2) $C_1$–$C_4$ alkoxy, (3) halogen (4) formyl (5) carboxyl (6) $C_1$–$C_4$ acyloxy (7) phenyl or substituted phenyl (8) hydroxy (9) nitro (10) amino (11) furyl (12) triazolyl (13) thienyl (14) piperazinyl (15) morpholinyl (16) thiomorpholinyl (17) imidazolyl (18) oxazolyl and (19) triazolone-yl;

$R_1$ and $R_2$ are each independently selected from the group consisting of (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino (3) nitro (4) amino (5) cyano (6) carboxyl (7) $SO_2R'$ wherein R' is hydrogen, alkyl or aryl and (8) $C_1$–$C_4$ alkoxy;

Y is a phenyl group which is unsubstituted or substituted with substituents each independently selected from the group consisting of (1) halogen (2) nitro (3) amino (4) cyano (5) carboxyl (6) hydroxy (7) $C_1$–$C_4$ alkoxy and (8) $SO_2R'$ wherein R' is hydrogen, alkyl or aryl;

$R_3$ is selected from the group consisting of hydrogen, $C_1$–$C_4$ alkyl group, halogen, hydroxy, $C_1$–$C_4$ alkoxy, nitro, amino, cyano, carboxyl and $SO_2R'$ wherein R' is hydrogen, alkyl or aryl;

$X_1$, $X_2$, $Y_1$, $Y_2$ and Z are independently selected from the group consisting of hydrogen, halogen, nitro, cyano, amino, sulphonyl, aryl or substituted aryl, $C_1$–$C_4$ alkyl, $C_1$–$C_4$ alkoxy, and carboxyl, with the proviso that when $X_1$, $X_2$, $Y_1$, and $Y_2$ are all hydrogen, Z is not $C_1$–$C_4$ alkoxy.

2. A compound of Formula IB

FORMULA IB and its pharmaceutically acceptable salts, enantiomers, diastereomers, N-oxides, wherein X is selected from the group consisting of $CH_2$, CO, CS, $SO_2$ and —N=N—, R is selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino (2) $C_1$–$C_4$ alkoxy, (3) halogen (4) formyl (5) carboxyl (6) $C_1$–$C_4$ acyloxy (7) phenyl or substituted phenyl (8) hydroxy (9) nitro (10) amino (11) furyl (12) triazolyl (13) thienyl (14) piperazinyl (15) morpholinyl (16) thiomorpholinyl (17) imidazolyl (18) oxazolyl and (19) triazolone-yl;

$R_1$ and $R_2$ are each independently selected from the group consisting of (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino (3) nitro (4) amino (5) cyano (6) carboxyl (7) $SO_2R'$ wherein R' is hydrogen, alkyl or aryl and (8) $C_1$–$C_4$ alkoxy;

Y is a phenyl group which is unsubstituted or substituted with substituents each independently selected from the group consisting of (1) halogen (2) nitro (3) amino (4) cyano (5) carboxyl (6) hydroxy (7) $C_1$–$C_4$ alkoxy and (8) $SO_2R'$ wherein R' is hydrogen, alkyl or aryl;

$R_3$ is selected from the group consisting of hydrogen, $C_1$–$C_4$ alkyl group, halogen, hydroxy, $C_1$–$C_4$ alkoxy, nitro, amino, cyano, carboxyl and $SO_2R'$ wherein R' is hydrogen, alkyl or aryl;

$R_4$ is selected from the group consisting of hydrogen, $C_1$–$C_4$ alkyl group which is unsubstituted or substituted;

B is selected from oxygen and sulphur atoms; and $R_5$ is selected from the group (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino, (3) phenyl which is unsubstituted or substituted with 1–3 substituents each independently selected from the group consisting of (a) $C_1$–$C_4$ alkyl which is unsubstituted or substituted with 1–3 substituents each independently selected from the group consisting of halogen, hydroxy, $C_1$–$C_4$ alkoxy and amino (b) $C_1$–$C_4$ alkoxy, (c) halogen, (d) formyl (e) carboxyl (f) $C_1$–$C_4$ acyloxy (g) $C_1$–$C_4$ alkoxycarbonyl amino (h) phenyloxy or naphthyloxy carbonylamino (i) semicarbazido (j) formamido (k) thioformamido (l) hydroxy (m) nitro (n) amino (o) furyl (p) triazolyl (q) thienyl (r)

oxazolyl (s) imidazolyl (t) $CF_2$ and (u) $OCF_3$ (4) naphthyl or naphthyl ($C_1$–$C_4$ alkyl) which may be substituted with 1–6 substituents selected from (a) $C_1$–$C_5$ alkyl which is unsubstituted or substituted with 1–3 substituents each independently selected from the group consisting of halogen, hydroxy, $C_1$–$C_4$ alkoxy and amino, (b) halogen (c) ($C_1$–$C_4$ alkyl) halo, (d) $C_1$–$C_4$ alkoxy (e)hydroxy (f) amino (g) carboxyl (h) trifluoromethoxyl (i) trifluoromethyl (j) tetrafluoroethyl (k) tetrafluoroethoxyl (l) tetrafluoropropyl and (m) tetrafluoropropoxyl.

3. A compound of Formula II

FORMULA II

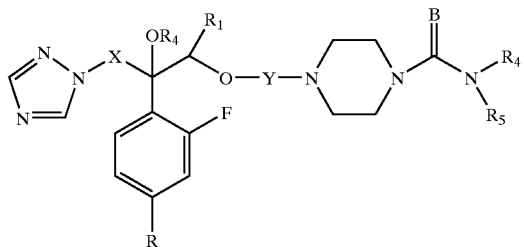

and its pharmaceutically acceptable salts, enantiomers, diastereomers, N-oxides, wherein X is selected from the group consisting of $CH_2$, CO, CS, $SO_2$ and —N═N—, R is selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino (2) $C_1$–$C_4$ alkoxy, (3) halogen (4) formyl (5) carboxyl (6) $C_1$–$C_4$ acyloxy (7) phenyl or substituted phenyl (8) hydroxy (9) nitro (10) amino (11) furyl (12) triazolyl (13) thienyl (14) piperazinyl (15) morpholinyl (16) thiomorpholinyl (17) imidazolyl (18) oxazolyl and (19) triazolone-yl;

$R_1$ is selected from the group consisting of (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino (3) nitro (4) amino (5) cyano (6) carboxyl (7) $SO_2R'$ wherein R' is hydrogen, alkyl or aryl and (8) $C_1$–$C_4$ alkoxy;

$R_4$ is selected from the group consisting of hydrogen, $C_1$–$C_4$ alkyl group which is unsubstituted or substituted; and $R_5$ is selected from the group (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino, (3) phenyl which is unsubstituted or substituted with 1–3 substituents each independently selected from the group consisting of (a) $C_1$–$C_4$ alkyl which is unsubstituted or substituted with 1–3 substituents each independently selected from the group consisting of halogen, hydroxy, $C_1$–$C_4$ alkoxy and amino (b) $C_1$–$C_4$ alkoxy, (c) halogen, (d) formyl (e) carboxyl (f) $C_1$–$C_4$ acyloxy (g) $C_1$–$C_4$ alkoxycarbonyl amino (h) phenyloxy or naphthyloxy carbonylamino (i) semicarbazido (j) formamido (k) thioformamido (l) hydroxy (m) nitro (n) amino (o) furyl (p) triazolyl (q) thienyl (r) oxazolyl (s) imidazolyl (t) $CF_2$ and (u) $OCF_3$ (4) naphthyl or naphthyl ($C_1$–$C_4$ alkyl) which may be substituted with 1–6 substituents selected from (a) $C_1$–$C_5$ alkyl which is unsubstituted or substituted with 1–3 substituents each independently selected from the group consisting of halogen, hydroxy, $C_1$–$C_4$ alkoxy and amino, (b) halogen (c) ($C_1$–$C_4$ alkyl) halo, (d) $C_1$–$C_4$ alkoxy (e)hydroxy (f) amino (g) carboxyl (h) trifluoromethoxyl (i) trifluoromethyl (j) tetrafluoroethyl (k) tetrafluoroethoxyl (l) tetrafluoropropyl and (m) tetrafluoropropoxyl;

B is selected from oxygen and sulphur atoms; and

Y is a phenyl group which is unsubstituted or substituted with substituents each independently selected from the group consisting of (1) halogen (2) nitro (3) amino (4) cyano (5) carboxyl (6) hydroxy (7) $C_1$–$C_4$ alkoxy and (8) $SO_2R'$ wherein R' is hydrogen, alkyl or aryl.

4. A compound is selected from the group consisting of:

2-{[1R2R/1S2S]-2-(2,4-Difluorophenyl)-2-hydroxy-1-methyl-3-(1H-1,2,4-triazol-1-yl)propyl}-4-{4-[4-(4-chlorophenyl)-1-piperazinyl]phenyl}-3-(2H,4H)-1,2,4-triazolone (Compound No. 1)

2-{[1R2S/1S2R]-2-(2,4-Difluorophenyl)-2-hydroxy-1-methyl-3-(1H-1,2,4-triazol-1-yl)propyl}-4-{4-[4-(4-chlorophenyl)-1-piperazinyl]phenyl}-3-(2H,4H)-1,2,4-triazolone (Compound No. 2)

2-{[1R2R/1S2S]-2-(2,4-Difluorophenyl)-2-hydroxy-1-methyl-3-(1H-1,2,4-triazol-1-yl)propyl}-4-{4-[4-(2,4-dinitrophenyl)-1-piperazinyl]phenyl}-3-(2H,4H)-1,2,4-triazolone (Compound No. 3)

2-{[1R2S/1S2R]-2-(2,4-Difluorophenyl)-2-hydroxy-1-methyl-3-(1H-1,2,4-triazol-1-yl)propyl}-4-{4-[4-(2,4-dinitrophenyl)-1-piperazinyl]phenyl}-3-(2H,4H)-1,2,4-triazolone (Compound No. 4)

2-{[1R2R/1S2S]-2-(2,4-Difluorophenyl)-2-hydroxy-1-methyl-3-(1H-1,2,4-triazol-1-yl)propyl}-4-[4-(1-phenylpiperazinyl)phenyl]3-(2H,4H)-1,2,4-triazolone (Compound No. 5)

2-{[1R2S/1S2R]-2-(2,4-Difluorophenyl)-2-hydroxy-1-methyl-3-(1H-1,2,4-triazol-1-yl)propyl}-4-[4-(1-phenylpiperazinyl)phenyl]3-(2H,4H)-1,2,4-triazolone (Compound No. 6)

2-{[1R2R/1S2S]-2-(2,4-Difluorophenyl)-2-hydroxy-1-methyl-3-(1H-1,2,4-triazol-1-yl)propyl}-4-{4-[4-(3,4-dichlorophenyl)-1-piperazinyl]phenyl}-3-(2H,4H)-1,2,4-triazolone (Compound No. 7)

2-{[1R2S/1S2R]-2-(2,4-Difluorophenyl)-2-hydroxy-1-methyl-3-(1H-1,2,4-triazol-1-yl)propyl}-4-{4-[4-(3,4-dichlorophenyl)-1-piperazinyl]phenyl}-3-(2H,4H)-1,2,4-triazolone (Compound No. 8)

2-{[1R2R/1S2S]-2-(2,4-Difluorophenyl)-2-hydroxy-1-methyl-3-(1H-1,2,4-triazol-1-yl)propyl}-4-{4-[4-(3-trifluoromentholphenyl)-1-piperazinyl]phenyl}-3-(2H, 4H)-1,2,4-triazolone (Compound No. 9)

2-{[1R2S/1S2R]-2-(2,4-Difluorophenyl)-2-hydroxy-1-methyl-3-(1H-1,2,4-triazol-1-yl)propyl}-4-{4-[4-(3-trifluoromentholphenyl)-1-piperazinyl]phenyl}-3-(2H, 4H)-1,2,4-triazolone (Compound No. 10)

2-{[1R2R/1S2S]-2-(2,4-Difluorophenyl)-2-hydroxy-1-methyl-3-(1H-1,2,4-triazol-1-yl)propyl}-4-{4-[4-(4-fluorophenyl)-1-piperazinyl]phenyl}-3-(2H,4H)-1,2,4-triazolone (Compound No. 11)

2-{[1R2S/1S2R]-2-(2,4-Difluorophenyl)-2-hydroxy-1-methyl-3-(1H-1,2,4-triazol-1-yl)propyl}-4-{4-[4-(4-fluorophenyl)-1-piperazinyl]phenyl}-3-(2H,4H)-1,2,4-triazolone (Compound No. 12)

2-{[1R2R/1S2S]-2-(2,4-Difluorophenyl)-2-hydroxy-1-methyl-3-(1H-1,2,4-triazol-1-yl)propyl}-4-{4-[4-(3- chloro-4-fluorophenyl)-1-piperazinyl]phenyl}-3-(2H,4H)-1,2,4-triazolone (Compound No. 15)

2-{[1R2S/1S2R]-2-(2,4-Difluorophenyl)-2-hydroxy-1-methyl-3-(1H-1,2,4-triazol-1-yl)propyl}-4-{4-[4-(3-chloro-4-fluorophenyl)-1-piperazinyl]phenyl}-3-(2H,4H)-1,2,4-triazolone (Compound No. 16)

2-{[1R2R/1S2S]-2-(2,4-Difluorophenyl)-2-hydroxy-1-methyl-3-(1H-1,2,4-triazol-1-yl)propyl}-4-{4-[4-(3-chloro-4-methylphenyl)-1-piperazinyl]phenyl}-3-(2H,4H)-1,2,4-triazolone (Compound No. 17)

2-{[1R2S/1S2R]-2-(2,4-Difluorophenyl)-2-hydroxy-1-methyl-3-(1H-1,2,4-triazol-1-yl)propyl}-4-{4-[4-(3-chloro-4-methylphenyl)-1-piperazinyl]phenyl}-3-(2H,4H)-1,2,4-triazolone (Compound No. 18)

2-{[1R2R/1S2S]-2-(2,4-Difluorophenyl)-2-hydroxy-1-methyl-3-(1H-1,2,4-triazol-1-yl)propyl}-4-{4-[4-(2,4-dimethylphenyl)-1-piperazinyl]phenyl}-3-(2H,4H)-1,2,4-triazolone (Compound No. 19)

2-{[1R2S/1S2R]-2-(2,4-Difluorophenyl)-2-hydroxy-1-methyl-3-(1H-1,2,4-triazol-1-yl)propyl}-4-{4-[4-(2,4-dimethylphenyl)-1-piperazinyl]phenyl}-3-(2H,4H)-1,2,4-triazolone (Compound No. 20)

2-{[1R2R/1S2S]-2-(2,4-Difluorophenyl)-2-hydroxy-1-methyl-3-(1H-1,2,4-triazol-1-yl)propyl}-4-{4-[4-(5-chloro-2-methylphenyl)-1-piperazinyl]phenyl}-3-(2H,4H)-1,2,4-triazolone (Compound No. 21)

2-{[1R2S/1S2R]-2-(2,4-Difluorophenyl)-2-hydroxy-1-methyl-3-(1H-1,2,4-triazol-1-yl)propyl}-4-{4-[4-(5-chloro-2-methylphenyl)-1-piperazinyl]phenyl}-3-(2H,4H)-1,2,4-triazolone (Compound No. 22)

2-{[1R2R/1S2S]-2-(2,4-Difluorophenyl)-2-hydroxy-1-methyl-3-(1H-1,2,4-triazol-1-yl)propyl}-4-{4-[4-(3,4-dimethylphenyl)-1-piperazinyl]phenyl}-3-(2H,4H)-5-methyl-1,2,4-triazolone (Compound No. 23)

2-{[1R2S/1S2R]-2-(2,4-Difluorophenyl)-2-hydroxy-1-methyl-3-(1H-1,2,4-triazol-1-yl)propyl}-4-{4-[4-(3,4-dimethylphenyl)-1-piperazinyl]phenyl}-3-(2H,4H)-5-methyl-1,2,4-triazolone (Compound No. 24)

2-{[1R2R/1S2S]-2-(2,4-Difluorophenyl)-2-hydroxy-1-methyl-3-(1H-1,2,4-triazol-1-yl)propyl}-4-{4-[4-(2-fluorophenyl)-1-piperazinyl]phenyl}-3-(2H,4H)-5-methyl-1,2,4-triazolone (Compound No. 25)

2-{[1R2S/1S2R]-2-(2,4-Difluorophenyl)-2-hydroxy-1-methyl-3-(1H-1,2,4-triazol-1-yl)propyl}-4-{4-[4-(2-fluorophenyl)-1-piperazinyl]phenyl}-3-(2H,4H)-5-methyl-1,2,4-triazolone (Compound No. 26)

2-{[1R2R/1S2S]-2-(2,4-Difluorophenyl)-2-hydroxy-1-methyl-3-(1H-1,2,4-triazol-1-yl)propyl}-4-{4-[4-(2-methoxy-5-fluorophenyl)-1-piperazinyl]phenyl}-3-(2H,4H)-5-methyl-1,2,4-triazolone (Compound No. 27)

2-{[1R2S/1S2R]-2-(2,4-Difluorophenyl)-2-hydroxy-1-methyl-3-(1H-1,2,4-triazol-1-yl)propyl}-4-{4-[4-(2-methoxy-5-fluorophenyl)-1-piperazinyl]phenyl}-3-(2H,4H)-5-methyl-1,2,4-triazolone (Compound No. 28)

2-{[1R2R/1S2S]-2-(2,4-Difluorophenyl)-2-hydroxy-1-methyl-3-(1H-1,2,4-triazol-1-yl)propyl}-4-{4-[4-(3,5-dichlorophenyl)-1-piperazinyl]phenyl}-3-(2H,4H)-5-methyl-1,2,4-triazolone (Compound No. 29)

2-{[1R2S/1S2R]-2-(2,4-Difluorophenyl)-2-hydroxy-1-methyl-3-(1H-1,2,4-triazol-1-yl)propyl}-4-{4-[4-(3,5-dichlorophenyl)-1-piperazinyl]phenyl}-3-(2H,4H)-5-methyl-1,2,4-triazolone (Compound No. 30)

2-{[1R2R/1S2S]-2-(2,4-Difluorophenyl)-2-hydroxy-1-methyl-3-(1H-1,2,4-triazol-1-yl)propyl}-4-{4-[4-(2-ethylphenyl)-1-piperazinyl]phenyl}-3-(2H,4H)-5-methyl-1,2,4-triazolone (Compound No. 31)

2-{[1R2S/1S2R]-2-(2,4-Difluorophenyl)-2-hydroxy-1-methyl-3-(1H-1,2,4-triazol-1-yl)propyl}-4-{4-[4-(2-ethylphenyl)-1-piperazinyl]phenyl}-3-(2H,4H)-5-methyl-1,2,4-triazolone (Compound No. 32)

2-{[1R2R/1S2S]-2-(2,4-Difluorophenyl)-2-hydroxy-1-methyl-3-(1H-1,2,4-triazol-1-yl)propyl}-4-{4-[4-(2,4-dichlorophenyl)-1-piperazinyl]phenyl}-3-(2H,4H)-5-methyl-1,2,4-triazolone (Compound No. 33)

2-{[1R2S/1S2R]-2-(2,4-Difluorophenyl)-2-hydroxy-1-methyl-3-(1H-1,2,4-triazol-1-yl)propyl}-4-{4-[4-(2,4-dichlorophenyl)-1-piperazinyl]phenyl}-3-(2H,4H)-5-methyl-1,2,4-triazolone (Compound No. 34)

2-[2-(2,4-Difluorophenyl)-2-hydroxy-3-(1H-1,2,4-triazol-1-yl)propyl]-4-{4-[4-(2-methoxyphenyl)-1-piperazinyl]phenyl}-3-(2H,4H)-5-methyl-1,2,4-triazolone (Compound No. 35)

2-[2-(2,4-Difluorophenyl)-2-hydroxy-3-(1H-1,2,4-triazol-1-yl)propyl]-4-{4-[4-(4-fluorophenyl)-1-piperazinyl]phenyl}-3-(2H,4H)-5-methyl-1,2,4-triazolone (Compound No. 36)

2-[2-(2,4-Difluorophenyl)-2-hydroxy-3-(1H-1,2,4-triazol-1-yl)propyl]-4-{4-[4-(3,4-dichlorophenyl)-1-piperazinyl]phenyl}-3-(2H,4H)-1,2,4-triazolone (Compound No. 37)

2-[2-(2,4-Difluorophenyl)-2-hydroxy-3-(1H-1,2,4-triazol-1-yl)propyl]-4-{4-[4-(2,4-diaminophenyl)-1-piperazinyl]phenyl}-3-(2H,4H)-1,2,4-triazolone (Compound No. 38)

2-[2-(2,4-Difluorophenyl)-2-hydroxy-3-(1H-1,2,4-triazol-1-yl)propyl]-4-{4-[4-(4-methylphenyl)-1-piperazinyl]phenyl}-3-(2H,4H)-1,2,4-triazolone (Compound No. 39)

2-[2-(2,4-Difluorophenyl)-2-hydroxy-3-(1H-1,2,4-triazol-1-yl)propyl]-4-{4-[4-(2,4-dimitrophenyl)-1-piperazinyl]phenyl}-3-(2H,4H)-1,2,4-triazolone (Compound No. 40)

2-[2-(2,4-Difluorophenyl)-2-hydroxy-3-(1H-1,2,4-triazol-1-yl)propyl]-4-{4-[4-(4-methoxyphenyl)-1-piperazinyl]phenyl}-3-(2H,4H)-1,2,4-triazolone (Compound No. 41)

2-[2-(2,4-Difluorophenyl)-2-hydroxy-3-(1H-1,2,4-triazol-1-yl)propyl]-4-{4-[4-(2-methoxyphenyl)-1-piperazinyl]phenyl}-3-(2H,4H)-1,2,4-triazolone (Compound No. 42)

2-[2-(2,4-Difluorophenyl)-2-hydroxy-3-(1H-1,2,4-triazol-1-yl)propyl]-4-{4-[4-(4-fluorophenyl)-1-piperazinyl]phenyl}-3-(2H,4H)-1,2,4-triazolone (Compound No. 43)

2-[2-(2,4-Difluorophenyl)-2-hydroxy-3-(1H-1,2,4-triazol-1-yl)propyl]-4-{4-[4-(4-hyroxphenyl)-1-piperazinyl]phenyl}-3-(2H,4H)-1,2,4-triazolone (Compound No. 44)

2-[2-(2,4-Difluorophenyl)-2-hydroxy-3-(1H-1,2,4-triazol-1-yl)propyl]-4-{4-[1-phenyl)-1-piperazinyl]phenyl}-3-(2H,4H)-1,2,4-triazolone (Compound No. 45)

2-[2-(2,4-Difluorophenyl)-2-hydroxy-3-(1H-1,2,4-triazol-1-yl)propyl]-4-{4-[4-(4-chlorophenyl)-1-piperazinyl]phenyl}-3-(2H,4H)-5-methyl-1,2,4-triazolone (Compound No. 46)

2-[2-(2,4-Difluorophenyl)-2-hydroxy-3-(1H-1,2,4-triazol-1-yl)propyl]-4-{4-[4-(4-chlorophenyl)-1-piperazinyl]phenyl}-3-(2H,4H)-1,2,4-triazolone (Compound No. 47)

2-[2-(2,4-Difluorophenyl)-2-hydroxy-3-(1H-1,2,4-triazol-1-yl)propyl]-4-{4-[4-(5-chloro-2-methylphenyl)-1-piperazinyl]phenyl}-3-(2H,4H)-1,2,4-triazolone (Compound No. 48)

2-[2-(2,4-Difluorophenyl)-2-hydroxy-3-(1H-1,2,4-triazol-1-yl)propyl]-4-{4-[4-(3-chloro-4-methylphenyl)-1-piperazinyl]phenyl}-3-(2H,4H)-1,2,4-triazolone (Compound No. 49)

2-[2-(2,4-Difluorophenyl)-2-hydroxy-3-(1H-1,2,4-triazol-1-yl)propyl]-4-{4-[4-(2,4-dichlorophenyl)-1-piperazinyl]phenyl}-3-(2H,4H)-1,2,4-triazolone (Compound No. 50)

2-[2-(2,4-Difluorophenyl)-2-hydroxy-3-(1H-1,2,4-triazol-1-yl)propyl]-4-{4-[4-(3-trifluoromethylphenyl)-1-piperazinyl]phenyl}-3-(2H,4H)-1,2,4-triazolone (Compound No. 51)

2-[2-(2,4-Difluorophenyl)-2-hydroxy-3-(1H-1,2,4-triazol-1-yl)propyl]-4-{4-[4-(2,4-difluorophenyl)-1-piperazinyl]phenyl}-3-(2H,4H)-1,2,4-triazolone (Compound No. 52)

2-[2-(2,4-Difluorophenyl)-2-hydroxy-3-(1H-1,2,4-triazol-1-yl)propyl]-4-{4-[4-(3-chloro-4-fluorophenyl)-1-piperazinyl]phenyl}-3-(2H,4H)-1,2,4-triazolone (Compound No. 53)

2-[2-(2,4-Difluorophenyl)-2-hydroxy-3-(1H-1,2,4-triazol-1-yl)propyl]-4-{4-[4-(2,4-dimethylphenyl)-1-piperazinyl]phenyl}-3-(2H,4H)-1,2,4-triazolone (Compound No. 54)

2-[2-(2,4-Difluorophenyl)-2-hydroxy-3-(1H-1,2,4-triazol-1-yl)propyl]-4-{4-[4-(3,4-difluorophenyl)-1-piperazinyl]phenyl}-3-(2H,4H)-1,2,4-triazolone (Compound No. 55)

2-[2-(2,4-Difluorophenyl)-2-hydroxy-3-(1H-1,2,4-triazol-1-yl)propyl]-4-{4-[4-(3,4-dimethylphenyl)-1-piperazinyl]phenyl}-3-(2H,4H)-1,2,4-triazolone (Compound No. 56)

2-[2-(2,4-Difluorophenyl)-2-hydroxy-3-(1H-1,2,4-triazol-1-yl)propyl]-4-{4-[4-(3-chlorophenyl)-1-piperazinyl]phenyl}-3-(2H,4H)-1,2,4-triazolone (Compound No. 57)

2-[2-(2,4-Difluorophenyl)-2-hydroxy-3-(1H-1,2,4-triazol-1-yl)propyl]-4-{4-[4-(2-chloro-4-fluorophenyl)-1-piperazinyl]phenyl}-3-(2H,4H)-1,2,4-triazolone (Compound No. 58)

2-[2-(2,4-Difluorophenyl)-2-hydroxy-3-(1H-1,2,4-triazol-1-yl)propyl]-4-{4-[4-(2-methoxy-5-fluorophenyl)-1-piperazinyl]phenyl}-3-(2H,4H)-1,2,4-triazolone (Compound No. 59)

2-[2-(2,4-Difluorophenyl)-2-hydroxy-3-(1H-1,2,4-triazol-1-yl)propyl]-4-{4-[4-(2-ethylphenyl)-1-piperazinyl]phenyl}-3-(2H,4H)-1,2,4-triazolone (Compound No. 60)

2-[2-(2,4-Difluorophenyl)-2-hydroxy-3-(1H-1,2,4-triazol-1-yl)propyl]-4-{4-[4-(3,5-dichlorophenyl)-1-piperazinyl]phenyl}-3-(2H,4H)-1,2,4-triazolone (Compound No. 61)

2-[2-(2,4-Difluorophenyl)-2-hydroxy-3-(1H-1,2,4-triazol-1-yl)propyl]-4-{4-[4-(2-fluorophenyl)-1-piperazinyl]phenyl}-3-(2H,4H)-1,2,4-triazolone (Compound No. 62)

2-[2-(2,4-Difluorophenyl)-2-hydroxy-3-(1H-1,2,4-triazol-1-yl)propyl]-4-{4-[4-(1,2,3-trifluorophenyl)-1-piperazinyl]phenyl}-3-(2H,4H)-1,2,4-triazolone (Compound No. 63)

3-{4-[4-(p-tolylaminothiocarbonylamino)piperazinyl]phenoxy}-2-(2,4-difluorophenyl)-1-(1H-1,2,4-triazol-1-yl)-propan-2-ol. (Compound No. 64)

3-{4-[4-(isopropylaminothiocarbonylamino)piperazinyl]phenoxy}-2-(2,4-difluorophenyl)-1-(1H-1,2,4-triazol-1-yl)-propan-2-ol. (Compound No. 65)

3-{4-[4-(4-chlorophenylureido)piperazinyl]phenoxy}-2-(2,4-difluorophenyl)-1-(1H-1,2,4-triazol-1-yl)-propan-2-ol (Compound No. 66)

3-{4-[4-(4-chlorophenylureido)piperazinyl]phenoxy}-2-(2,4-difluorophenyl)-1-(1H-1,2,4-triazol-1-yl)-propan-2-ol. (Compound No. 67)

3-{4-[4-(1-napthylthioureido)piperazinyl]phenoxy}-2-(2,4-difluorophenyl)-1-(1H-1,2,4-triazol-1-yl)-propan-2-ol. (Compound No. 68)

3-{4-[4-(1-hapthylthioureido)piperazinyl]phenoxy}-2-(2,4-difluorophenyl)-1-(1H-1,2,4-triazol-1-yl)-propan-2-ol. (Compound No. 69)

3-{4-[4-(4-trifluoromethylphenylthioureido)piperazinyl]phenoxy}-2-(2,4-difluorophenyl)-1-(1H-1,2,4-triazol-1-yl)-propan-2-ol. (Compound No. 70)

3-{4-[4-(4-methoxyphenylureido)piperazinyl]phenoxy}-2-(2,4-difluorophenyl)-1-(1H-1,2,4-triazol-1-yl)-propan-2-ol. (Compound No. 71)

3-{4-[4-(2,4-dichlorophenylureido)piperazinyl]phenoxy}-2-(2,4-difluorophenyl)-1-(1H-1,2,4-triazol-1-yl)-propan-2-ol (Compound No. 72)

3-{4-[4-(4-chlorophenyl-N-ethylureido)-piperazinyl]-phenoxy}-2-(2,4-difluorophenyl)-1-(1H-1,2,4-triazolyl)-propan-3-amino-2-ol (Compound No. 73)

3-{4-[4-(4-chlorophenyl-N-ethylureido)-piperazinyl]-phenoxy}-2-(2,4-difluorophenyl)-1-(1H-1,2,4-triazolyl)-2-ethoxy-3-propylamine (Compound No. 74)

3-{4-[4-N-(4-Chlorophenyl)-N-(methylureido)-piperazinyl]-phenoxy}-2-(2,4-difluorophenyl)-1-(1H-1,2,4-triazolyl)-2-methoxypropane (Compound No. 75)

3-{4-[4-(4-aminophenylureido)piperazinyl]phenoxy}-2-(2,4-difluorophenyl)-1-(1H-1,2,4-triazol-1-yl)-propan-2-ol. (Compound No. 76)

[1R2R/1S2S]1-{4-[4-(4-chlorophenylureido)-piperazinyl]-phenoxy}-2-(2,4-difluorophenyl)-1-methyl-3-(1H-1,2,4-triazolyl)-propan-2-ol (Compound No. 77)

[1R2S/1S2R]1-{4-[4-(4-chlorophenylureido)-piperazinyl]-phenoxy}2-(2,4-difluorophenyl)-1-methyl-3-(1H-1,2,4-triazolyl)-propan-2-ol (Compound No. 78)

1-{4-[4-(4-Trifluoromethylphenylureido)piperazinyl]phenoxy}-2-(2,4-difluorophenyl)-1-methyl-3-(1H-1,2,4-triazol-1-yl)-propan-2-ol (Compound No. 79)

3-{4-[4-(Phenylureido)-piperazinyl]-phenoxy}-2-(2,4-difluorophenyl)-1-(1H-1,2,4-triazol-1-yl)-propan-2-ol (Compound No. 80)

2-(2,4-Difluorophenyl)-3-{4-(thioureidophenyl)N-methyl-N-phenyl}-1-(1H-1,2,4-triazolyl)-propan-3-amino-2-ol (Compound No. 81)

2-(2,4-Difluorophenyl)-3-{4-(isopropylthioureido)N-methyl-N-phenyl}-1-(1H-1,2,4-triazolyl)-propan-3-amino-2-ol (Compound No. 82)

3-{N-[4-(p-Tolylthioureido)-phenyl]-N-methyl}-2-(2,4-difluorophenyl)-1-(1H-1,2,4-triazolyl)-propan-3-amino-2-ol (Compound No. 83)

3-{N-[4-(p-Fluorophenylureido)-phenyl]-N-methyl}-2-(2,4-difluorophenyl)-1-(1H-1,2,4-triazolyl)-propan-3-amino-2-ol (Compound No. 84)

33-{N-[4-(p-nitrophenylureido)-phenyl]-N-methyl}-2-(2,4-difluorophenyl)-1-(1H-1,2,4-triazolyl)-propan-3-amino-2-ol (Compound No. 85)

3-{N-[4-(p-Chlorophenylureido)-phenyl]-N-methyl}-2-(2,4-difluorophenyl)-1-(1H-1,2,4-triazolyl)-propan-3-amino-2-ol (Compound No. 86)

3-{N-[4-(Carboxymethyl)-phenylureido)-phenyl]-N-methyl}-2-(2,4-difluorophenyl)-1-(1H-1,2,4-triazolyl)-propan-3-amino-2-ol (Compound No. 87)

3-{N-[4-(2-Methoxy-2-oxoethyl)-phenylureido)-phenyl]-N-methyl}-2-(2,4-difluorophenyl)-1-(1H-1,2,4-triazolyl)-propan-3-amino-2-ol (Compound No. 88)

3-{N-[4-(p-Chlorophenylthioureido)-phenylureido)-phenyl]-N-methyl}-2-(2,4-difluorophenyl)-1-(1H-1,2,4-triazolyl)-propan-3-amino-2-ol (Compound No. 89)

2-[2-(2,4-Difluorophenyl)-2-hydroxy-3-(1H-1,2,4-triazol-1-yl)propyl]-4-{4-[4-(isopropylthiouredio)-1-piperazinyl]phenyl}-3-(2H,4H)-1,2,4-triazolone (Compound No. 90)

2-[2-(2,4-Difluorophenyl)-2-hydroxy-3-(1H-1,2,4-triazol-1-yl)propyl]-4-{4-[4-(4-chlorophenyluredio)-1-piperazinyl]phenyl}-3-(2H,4H)-1,2,4-triazolone (Compound No. 91)

2-[2-(2,4-Difluorophenyl)-2-hydroxy-3-(1H-1,2,4-triazol-1-yl)propyl]-4-{4-[4-(4-chlorophenylthiouredio)-1-piperazinyl]phenyl}-3-(2H,4H)-1,2,4-triazolone (Compound No. 92)

2-[2-(2,4-Difluorophenyl)-2-hydroxy-3-(1H-1,2,4-triazol-1-yl)propyl]-4-{4-[4-(4-(2-methoxy-2-oxoethyl)phenyl)-1-piperazinyl]phenyl}-3-(2H,4H)-1,2,4-triazolone (Compound No. 93)

2-[2-(2,4-Difluorophenyl)-2-hydroxy-3-(1H-1,2,4-triazol-1-yl)propyl]-4-{4-[4-(4-(carboxyethyl)-phenyl)-1-piperazinyl]phenyl}-3-(2H,4H)-1,2,4-triazolone (Compound No. 94)

2-[2-(2,4-Difluorophenyl)-2-hydroxy-3-(1H-1,2,4-triazol-1-yl)propyl]-4-{4-[4-(4-(2-hydroxyethyl)phenyl)-1-piperazinyl]phenyl}-3-(2H,4H)-1,2,4-triazolone(Compound No. 95).

5. A pharmaceutical composition comprising a compound of claim 1 to 5 and a pharmaceutical acceptable carrier.

6. A method of treating fungal infection in mammals comprising administering to said animal a compound of Formula IA

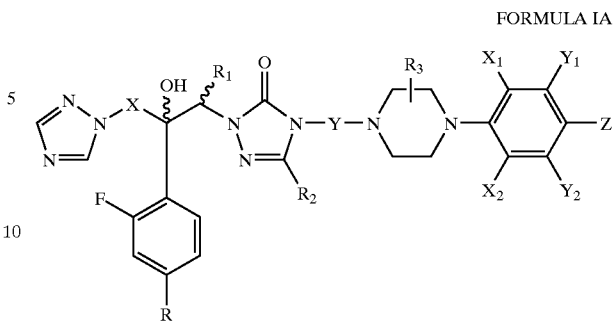

FORMULA IA and its pharmaceutically acceptable salts, enantiomers, diastereomers, N-oxides, wherein X is selected from the group consisting of $CH_2$, CO, CS, $SO_2$ and —N=N—, R is selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino (2) $C_1$–$C_4$ alkoxy, (3) halogen (4) formyl (5) carboxyl (6) $C_1$–$C_4$ acyloxy (7) phenyl or substituted phenyl (8) hydroxy (9) nitro (10) amino (11) furyl (12) triazolyl (13) thienyl (14) piperazinyl (15) morpholinyl (16) thiomorpholinyl (17) imidazolyl (18) oxazolyl and (19) triazolone-yl;

$R_1$ and $R_2$ are each independently selected from the group consisting of (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino (3) nitro (4) amino (5) cyano (6) carboxyl (7) $SO_2R'$ wherein R' is hydrogen, alkyl or aryl and (8) $C_1$–$C_4$ alkoxy;

Y is a phenyl group which is unsubstituted or substituted with substituents each independently selected from the group consisting of (1) halogen (2) nitro (3) amino (4) cyano (5) carboxyl (6) hydroxy (7) $C_1$–$C_4$ alkoxy and (8) $SO_2R'$ wherein R' is hydrogen, alkyl or aryl;

$R_3$ is selected from the group consisting of hydrogen, $C_1$–$C_4$ alkyl group, halogen, hydroxy, $C_1$–$C_4$ alkoxy, nitro, amino, cyano, carboxyl and $SO_2R'$ wherein R' is hydrogen, alkyl or aryl; and $X_1$, $X_2$, $Y_1$, $Y_2$ and Z are independently selected from the group consisting of hydrogen, halogen, nitro, cyano, amino, sulphonyl, aryl or substituted aryl, $C_1$–$C_4$ alkyl, $C_1$–$C_4$ alkoxy, and carboxyl, with the proviso that when $X_1$, $X_2$, and $Y_1$ and $Y_2$ are all hydrogen, Z is not $C_1C_4$ alkoxy.

7. A method of treating fungal infection in an animal comprising administering to said animal a compound of Formula IB

FORMULA IB

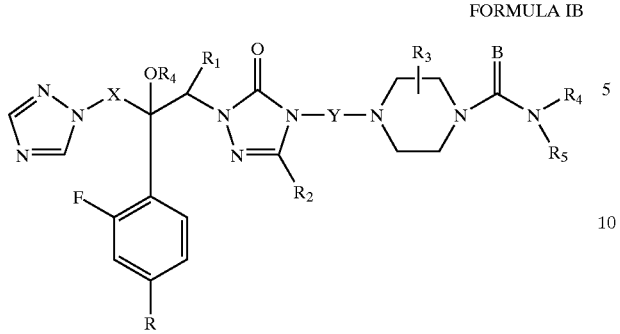

and its pharmaceutically acceptable salts, enantiomers, diastereomers, N-oxides, wherein X is selected from the group consisting of $CH_2$, CO, CS, $SO_2$ and —N=N—;

R is selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino (2) $C_1$–$C_4$ alkoxy, (3) halogen (4) formyl (5) carboxyl (6) $C_1$–$C_4$ acyloxy (7) phenyl or substituted phenyl (8) hydroxy (9) nitro (10) amino (11) furyl (12) triazolyl (13) thienyl (14) piperazinyl (15) morpholinyl (16) thiomorpholinyl (17) imidazolyl (18) oxazolyl and (19) triazolone-yl;

$R_1$ and $R_2$ are each independently selected from the group consisting of (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino (3) nitro (4) amino (5) cyano (6) carboxyl (7) $SO_2R'$ wherein R' is hydrogen, alkyl or aryl and (8) $C_1$–$C_4$ alkoxy;

Y is a phenyl group which is unsubstituted or substituted with substituents each independently selected from the group consisting of (1) halogen (2) nitro (3) amino (4) cyano (5) carboxyl (6) hydroxy (7) $C_1$–$C_4$ alkoxy and (8) $SO_2R'$ wherein R' is hydrogen, alkyl or aryl;

$R_3$ is selected from the group consisting of hydrogen, $C_1$–$C_4$ alkyl group, halogen, hydroxy, $C_1$–$C_4$ alkoxy, nitro, amino, cyano, carboxyl and $SO_2R'$ wherein R' is hydrogen, alkyl or aryl;

$R_4$ is selected from the group consisting of hydrogen, $C_1$–$C_4$ alkyl group which is unsubstituted or substituted;

B is selected from oxygen and sulphur atoms; and $R_5$ is selected from the group (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino, (3) phenyl which is unsubstituted or substituted with 1–3 substituents each independently selected from the group consisting of (a) $C_1$–$C_4$ alkyl which is unsubstituted or substituted with 1–3 substituents each independently selected from the group consisting of halogen, hydroxy, $C_1$–$C_4$ alkoxy and amino (b) $C_1$–$C_4$ alkoxy, (c) halogen, (d) formyl (e) carboxyl (f) $C_1$–$C_4$ acyloxy (g) $C_1$–$C_4$ alkoxycarbonyl amino (h) phenyloxy or naphthyloxy carbonylamino (i) semicarbazido (j) formamido (k) thioformamido (l) hydroxy (m) nitro (n) amino (o) furyl (p) triazolyl (q) thienyl (r) oxazolyl (s) imidazolyl (t) $CF_2$ and (u) $OCF_3$ (4) naphthyl or naphthyl ($C_1$–$C_4$ alkyl) which may be substituted with 1–6 substituents selected from (a) $C_1$–$C_5$ alkyl which is unsubstituted or substituted with 1–3 substituents each independently selected from the group consisting of halogen, hydroxy, $C_1$–$C_4$ alkoxy and amino, (b) halogen (c) ($C_1$–$C_4$ alkyl) halo, (d) $C_1$–$C_4$ alkoxy (e) hydroxy (f) amino (g) carboxyl (h) trifluoromethoxyl (i) trifluoromethyl (j) tetrafluoroethyl (k) tetrafluoroethoxyl (l) tetrafluoropropyl and (m) tetrafluoropropoxyl.

8. A method of treating fungal infection in an animal comprising administering to said animal a compound of Formula II

FORMULA II

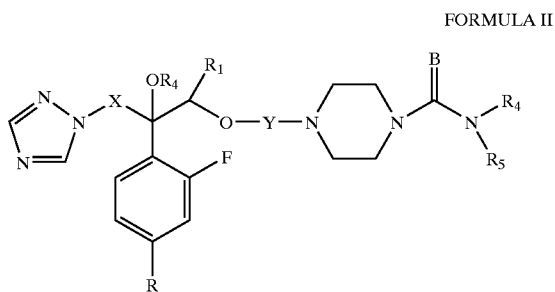

and its pharmaceutically acceptable salts, enantiomers, diastereomers, N-oxides, wherein X is selected from the group consisting of $CH_2$, CO, CS, $SO_2$ and —N=N—;

R is selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino (2) $C_1$–$C_4$ alkoxy, (3) halogen (4) formyl (5) carboxyl (6) $C_1$–$C_4$ acyloxy (7) phenyl or substituted phenyl (8) hydroxy (9) nitro (10) amino (11) furyl (12) triazolyl (13) thienyl (14) piperazinyl (15) morpholinyl (16) thiomorpholinyl (17) imidazolyl (18) oxazolyl and (19) triazolone-yl;

$R_1$ is selected from the group consisting of (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino (3) nitro (4) amino (5) cyano (6) carboxyl (7) $SO_2R'$ wherein R' is hydrogen, alkyl or aryl and (8) $C_1$–$C_4$ alkoxy;

$R_4$ is selected from the group consisting of hydrogen, $C_1$–$C_4$ alkyl group which is unsubstituted or substituted;

$R_5$ is selected from the group (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino, (3) phenyl which is unsubstituted or substituted with 1–3 substituents each independently selected from the group consisting of (a) $C_1$–$C_4$ alkyl which is unsubstituted or substituted with 1–3 substituents each independently selected from the group consisting of halogen, hydroxy, $C_1$–$C_4$ alkoxy and amino (b) $C_1$–$C_4$ alkoxy, (c) halogen, (d) formyl (e) carboxyl (f) $C_1$–$C_4$ acyloxy (g) $C_1$–$C_4$ alkoxycarbonyl amino (h) phenyloxy or naphthyloxy carbonylamino (i) semicarbazido (j) formamido (k) thioformamido (l) hydroxy (m) nitro (n) amino (o) furyl (p) triazolyl (q) thienyl (r) oxazolyl (s) imidazolyl (t) $CF_2$ and (u) $OCF_3$ (4) naphthyl or naphthyl ($C_1$–$C_4$ alkyl) which may be substituted with 1–6 substituents selected from (a) $C_1$–$C_5$ alkyl which is unsubstituted or substituted with 1–3 substituents each independently selected from the group consisting of halogen, hydroxy, $C_1$–$C_4$ alkoxy and amino, (b) halogen (c) ($C_1$–$C_4$ alkyl) halo, (d) $C_1$–$C_4$ alkoxy (e) hydroxy (f) amino (g) carboxyl (h) trifluoromethoxyl (i) trifluoromethyl (j) tetrafluoroethyl (k) tetrafluoroethoxyl (l) tetrafluoropropyl and (m) tetrafluoropropoxyl;

B is selected from oxygen and sulphur atoms; and

Y is a phenyl group which is unsubstituted or substituted with substituents each independently selected from the group consisting of (1) halogen (2) nitro (3) amino (4) cyano (5) carboxyl (6) hydroxy (7) $C_1$–$C_4$ alkoxy and (8) $SO_2R'$ wherein R' is hydrogen, alkyl or aryl.

9. A method of treating fungal infection in an animal comprising the step of administering to said animal the pharmaceutical composition according to claim 6.

10. A process for preparing a compound of Formula IA

FORMULA IA

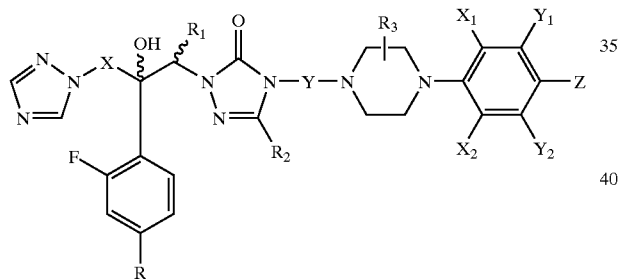

wherein X is selected from the group consisting of $CH_2$, CO, CS, $SO_2$ and —N=N—;

R is selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino (2) $C_1$–$C_4$ alkoxy, (3) halogen (4) formyl (5) carboxyl (6) $C_1$–$C_4$ acyloxy (7) phenyl or substituted phenyl (8) hydroxy (9) nitro (10) amino (11) furyl (12) triazolyl (13) thienyl (14) piperazinyl (15) morpholinyl (16) thiomorpholinyl (17) imidazolyl (18) oxazolyl and (19) triazolone-yl;

$R_1$ and $R_2$ are each independently selected from the group consisting of (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino (3) nitro (4) amino (5) cyano (6) carboxyl (7) $SO_2R'$ wherein R' is hydrogen, alkyl or aryl and (8) $C_1$–$C_4$ alkoxy;

Y is a phenyl group which is unsubstituted or substituted with substituents each independently selected from the group consisting of (1) halogen (2) nitro (3) amino (4) cyano (5) carboxyl (6) hydroxy (7) $C_1$–$C_4$ alkoxy and (8) $SO_2R'$ wherein R' is hydrogen, alkyl or aryl;

$R_3$ is selected from the group consisting of hydrogen, $C_1$–$C_4$ alkyl group, halogen, hydroxy, $C_1$–$C_4$ alkoxy, nitro, amino, cyano, carboxyl and $SO_2R'$ wherein R' is hydrogen, alkyl or aryl; and $X_1$, $X_2$, $Y_1$, $Y_2$ and Z are independently selected from the group consisting of hydrogen, halogen, nitro, cyano, amino, sulphonyl, aryl or substituted aryl, $C_1$–$C_4$ alkyl, $C_1$–$C_4$ alkoxy, and carboxyl, with the proviso that when $X_1$, $X_2$, $Y_1$ and $Y_2$ are all hydrogen, Z is not $C_1$–$C_4$ alkoxy, which comprises reacting 1-[2-(2,4-disubstituted phenyl)-2,3-epoxy derivative of 1,2,4-triazole of Formula IV

FORMULA IV

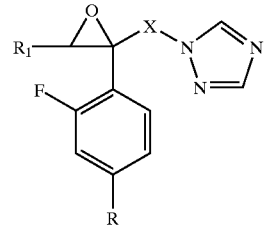

wherein X, R and $R_1$ are the same as defined above with triazol-3-one derivatives of Formula V

FORMULA V

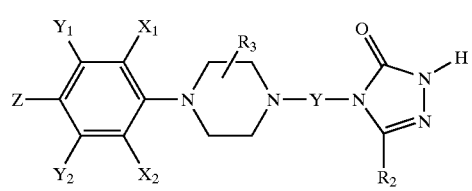

wherein $R_2$, $R_3$, $X_1$, $X_2$, Y, $Y_1$, $Y_2$ and Z have the same meanings as defined above, in the presence of sodium hydride to afford the desired compound of Formula IA.

11. A process for preparing a compound of Formula IB,

FORMULA IB

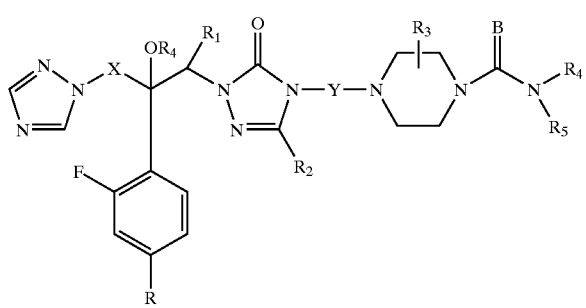

wherein X is selected from the group consisting of $CH_2$, CO, CS, $SO_2$ and —N=N—;

R is selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino (2) $C_1$–$C_4$ alkoxy, (3) halogen (4) formyl (5) carboxyl (6) $C_1$–$C_4$ acyloxy (7) phenyl or substituted phenyl (8) hydroxy (9) nitro (10) amino (11) furyl (12) triazolyl (13) thienyl (14) piperazinyl (15) morpholinyl (16) thiomorpholinyl (17) imidazolyl (18) oxazolyl and (19) triazolone-yl;

$R_1$ and $R_2$ are each independently selected from the group consisting of (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino (3) nitro (4) amino (5) cyano (6) carboxyl (7) $SO_2R'$ wherein R' is hydrogen, alkyl or aryl and (8) $C_1$–$C_4$ alkoxy;

Y is a phenyl group which is unsubstituted or substituted with substituents each independently selected from the group consisting of (1) halogen (2) nitro (3) amino (4) cyano (5) carboxyl (6) hydroxy (7) $C_1$–$C_4$ alkoxy and (8) $SO_2R'$ wherein R' is hydrogen, alkyl or aryl;

$R_3$ is selected from the group consisting of hydrogen, $C_1$–$C_4$ alkyl group, halogen, hydroxy, $C_1$–$C_4$ alkoxy, nitro, amino, cyano, carboxyl and $SO_2R'$ wherein R' is hydrogen, alkyl or aryl;

$R_4$ is selected from the group consisting of hydrogen, $C_1$–$C_4$ alkyl group which is unsubstituted or substituted;

B is selected from oxygen and sulphur atoms; and $R_5$ is selected from the group (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino, (3) phenyl which is unsubstituted or substituted with 1–3 substituents each independently selected from the group consisting of (a) $C_1$–$C_4$ alkyl which is unsubstituted or substituted with 1–3 substituents each independently selected from the group consisting of halogen, hydroxy, $C_1$–$C_4$ alkoxy and amino (b) $C_1$–$C_4$ alkoxy, (c) halogen, (d) formyl (e) carboxyl (f) $C_1$–$C_4$ acyloxy (g) $C_1$–$C_4$ alkoxycarbonyl amino (h) phenyloxy or naphthyloxy carbonylamino (i) semicarbazido (j) formamido (k) thioformamido (l) hydroxy (m) nitro (n) amino (o) furyl (p) triazolyl (q) thienyl (r) oxazolyl (s) imidazolyl (t) $CF_2$ and (u) $OCF_3$ (4) naphthyl or naphthyl ($C_1$–$C_4$ alkyl) which may be substituted with 1–6 substituents selected from (a) $C_1$–$C_5$ alkyl which is unsubstituted or substituted with 1–3 substituents each independently selected from the group consisting of halogen, hydroxy, $C_1$–$C_4$ alkoxy and amino, (b) halogen (c) ($C_1$–$C_4$ alkyl) halo, (d) $C_1$–$C_4$ alkoxy (e)hydroxy (f) amino (g) carboxyl (h) trifluoromethoxyl (i) trifluoromethyl (j) tetrafluoroethyl (k) tetrafluoroethoxyl (l) tetrafluoropropyl and (m) tetrafluoropropoxyl, which comprises reacting a compound of Formula ID

FORMULA ID

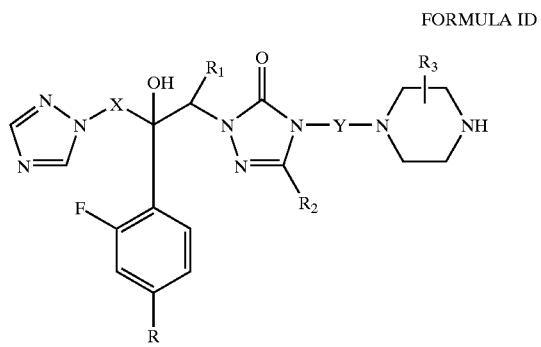

wherein X, R, $R_1$, $R_2$, $R_3$ and Y have the same meanings as defined above, with a compound of Formula $R_5$—N=C=B wherein $R_5$ and B are the same as defined above to give a compound of Formula IC

FORMULA IC

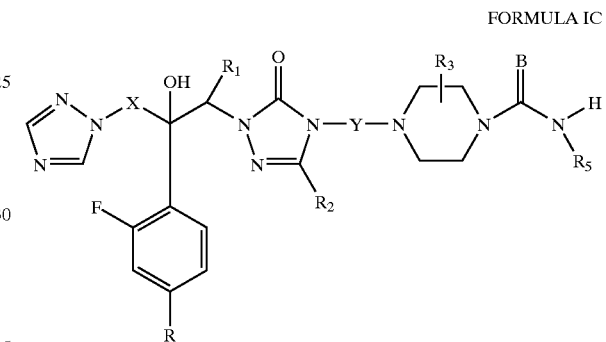

which on reaction with $R_4Z$, gives a compound of Formula IB wherein X, R, $R_1$, $R_2$, $R_3$, $R_4$, $R_5$, Y and B have the same meanings as defined above and Z is any halogen atom.

12. A process for preparing a compound of Formula II

FORMULA II

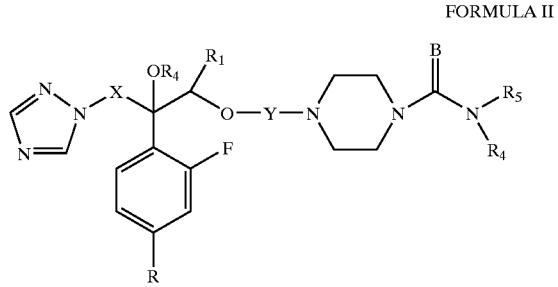

wherein X is selected from the group consisting of $CH_2$, CO, CS, $SO_2$ and —N=N—;

R is selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino (2) $C_1$–$C_4$ alkoxy, (3) halogen (4) formyl (5) carboxyl (6) $C_1$–$C_4$ acyloxy (7) phenyl or substituted phenyl (8) hydroxy (9) nitro (10) amino (11) furyl (12) triazolyl (13) thienyl (14) piperazinyl (15) morpholinyl (16) thiomorpholinyl (17) imidazolyl (18) oxazolyl and (19) triazolone-yl;

$R_1$ is selected from the group consisting of (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino (3) nitro (4) amino (5) cyano (6) carboxyl (7) $SO_2R'$ wherein R' is hydrogen, alkyl or aryl and (8) $C_1$–$C_4$ alkoxy;

$R_4$ is selected from the group consisting of hydrogen, $C_1$–$C_4$ alkyl group which is unsubstituted or substituted;

$R_5$ is selected from the group (1) hydrogen, (2) $C_1$–$C_4$ alkyl group which is unsubstituted or substituted with 1–3 substituents each independently selected from the group consisting of halogen, hydroxy, $C_1$–$C_4$ alkoxy and amino, (3) phenyl which is unsubstituted or substituted with 1–3 substituents each independently selected from the group consisting of (a) $C_1$–$C_4$ alkyl which is unsubstituted or substituted with 1–3 substituents each independently selected from the group consisting of halogen, hydroxy, $C_1$–$C_4$ alkoxy and amino (b) $C_1$–$C_4$ alkoxy, (c) halogen, (d) formyl (e) carboxyl (f) $C_1$–$C_4$ acyloxy (g) $C_1$–$C_4$ alkoxycarbonyl amino (h) phenyloxy or naphthyloxy carbonylamino (i) semicarbazido (j) formamido (k) thioformamido (l) hydroxy (m) nitro (n) amino (o) furyl (p) triazolyl (q) thienyl (r) oxazolyl (s) imidazolyl (t) $CF_2$ and (u) $OCF_3$ (4) naphthyl or naphthyl ($C_1$–$C_4$ alkyl) which may be substituted with 1–6 substituents selected from (a) $C_1$–$C_5$ alkyl which is unsubstituted or substituted with 1–3 substituents each independently selected from the group consisting of halogen, hydroxy, $C_1$–$C_4$ alkoxy and amino, (b) halogen (c) ($C_1$–$C_4$ alkyl) halo, (d) $C_1$–$C_4$ alkoxy (e)hydroxy (f) amino (g) carboxyl (h) trifluoromethoxyl (i) trifluoromethyl (j) tetrafluoroethyl (k) tetrafluoroethoxyl (l) tetrafluoropropyl and (m) tetrafluoropropoxyl;

Y is a phenyl group which is unsubstituted or substituted with substituents each independently selected from the group consisting of (1) halogen (2) nitro (3) amino (4) cyano (5) carboxyl (6) hydroxy (7) $C_1$–$C_4$ alkoxy and (8) $SO_2R'$ wherein R' is hydrogen, alkyl or aryl; and, B is selected from oxygen and sulphur atoms;

which comprises reacting a compound of Formula VII

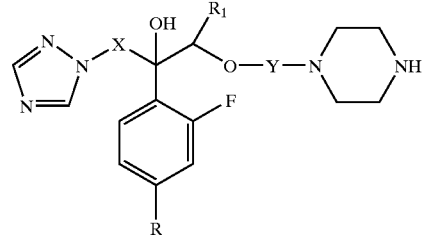

FORMULA VII with a compound $R_5$—N=B=B, wherein R, $R_1$, $R_5$, X and Y have the same meanings as defined above, to give a compound of Formula VIII

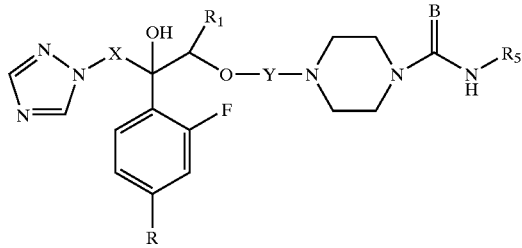

FORMULA VIII and which further comprises reacting the compound of Formula VIII with $R_4Z$, wherein $R_4$ is selected from the group consisting of hydrogen, $C_1$–$C_4$ alkyl group which is unsubstituted or substituted and Z is any halogen atom, to obtain a compound of Formula II.

* * * * *